United States Patent [19]

Wong et al.

[11] 4,414,981
[45] Nov. 15, 1983

[54] ELECTROCARDIOGRAPH COMPUTER DISPLAY SYSTEM

[75] Inventors: Alan S. Wong, Escondido; Mitchell S. Karwan, Santa Ana; Keith L. Germane, Costa Mesa, all of Calif.

[73] Assignee: Del Mar Avionics, Irvine, Calif.

[21] Appl. No.: 370,332

[22] Filed: Apr. 21, 1982

Related U.S. Application Data

[63] Continuation of Ser. No. 192,600, Sep. 30, 1980, abandoned.

[51] Int. Cl.³ ............................................... A61B 5/04
[52] U.S. Cl. .................................................. 128/712
[58] Field of Search ........................ 128/696, 702–704, 128/710–712

[56] References Cited

U.S. PATENT DOCUMENTS

| | | | |
|---|---|---|---|
| 3,215,136 | 2/1965 | Holter et al. | 128/712 |
| 3,853,119 | 12/1974 | Peterson et al. | 128/712 |
| 3,874,370 | 4/1975 | Harris et al. | 128/712 |
| 4,006,737 | 2/1977 | Cherry | 128/710 |
| 4,098,267 | 7/1978 | Stein et al. | 128/712 |
| 4,119,090 | 10/1978 | Dehnert | 128/712 |

*Primary Examiner*—William E. Kamm
*Attorney, Agent, or Firm*—Beehler, Pavitt, Siegemund, Jagger, & Martella

[57] ABSTRACT

A computer controlled method and apparatus for displaying an electrocardiograph utilizes a computer to store and display multiple channels of an ECG signal and to develop an AVSEP and arrhythmic display. A video ECG signal is stored in memory and the R waves of the ECG complexes are detected to form an R wave pulse train. Intervals of ECG memory are displayed from adresses representing a few cycles of the ECG signal. The display of the ECG signal is triggered by a corresponding R pulse train which is stored in an address which is offset sufficiently from the address of the ECG signal so that the entire ECG complex is displayed. The method and apparatus has the option wherein the display may be switched from a time moving scan display mode to a time stationary display mode over a fixed or variable interval of scanned ECG signals.

30 Claims, 97 Drawing Figures

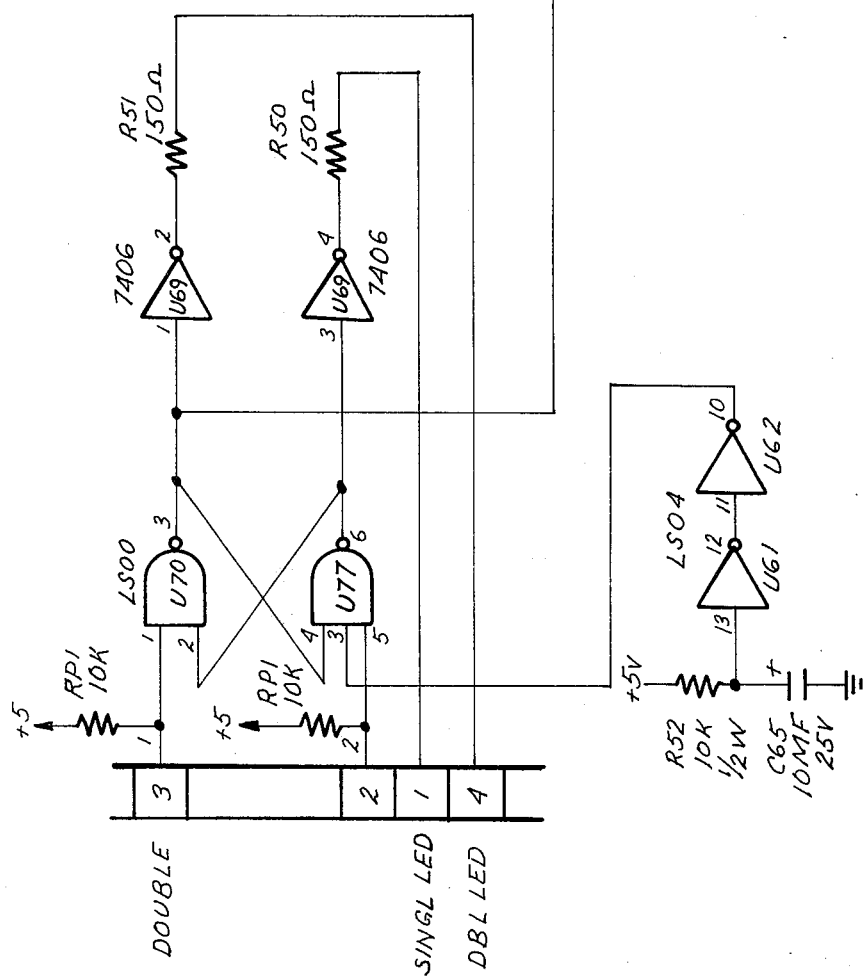

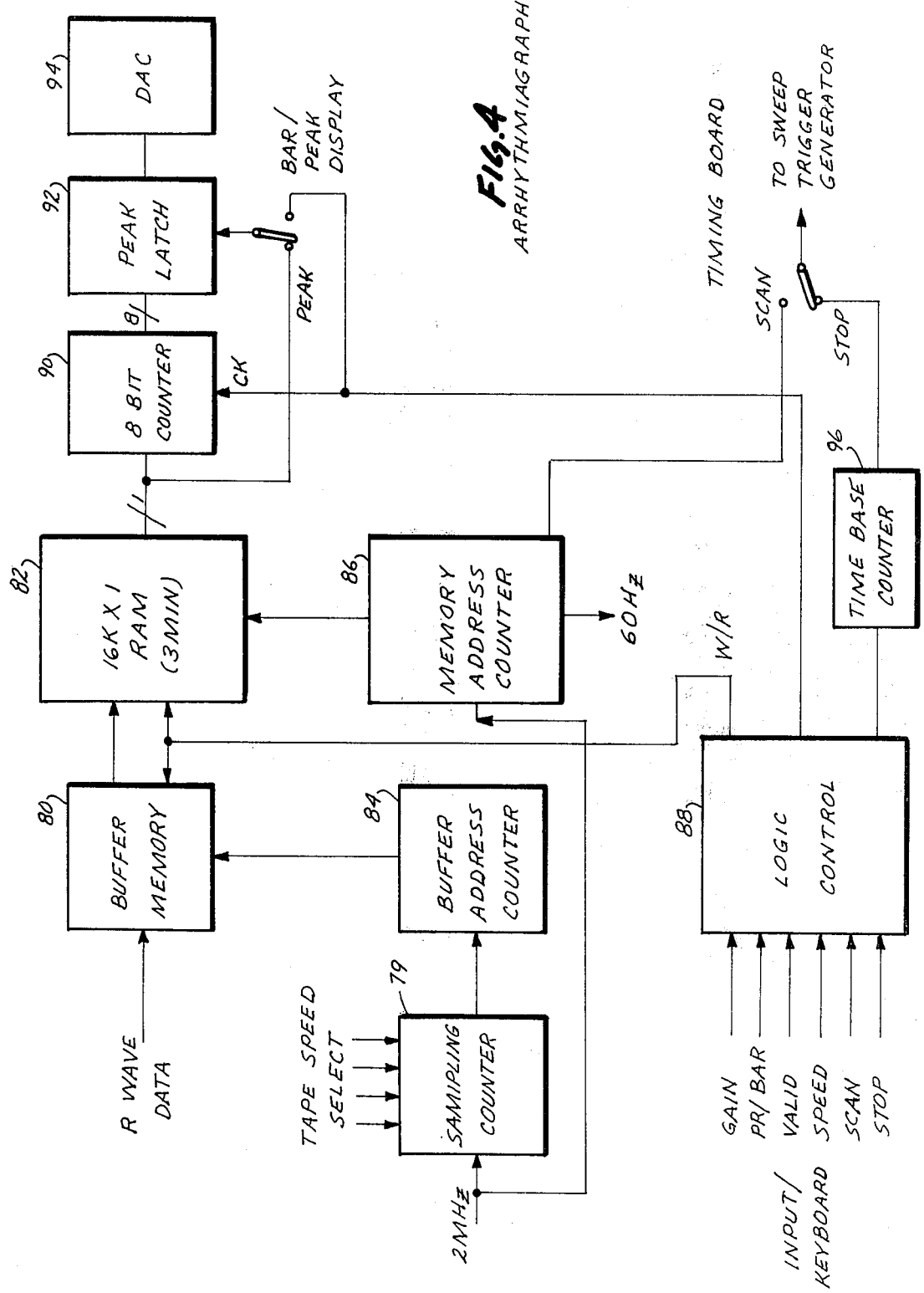

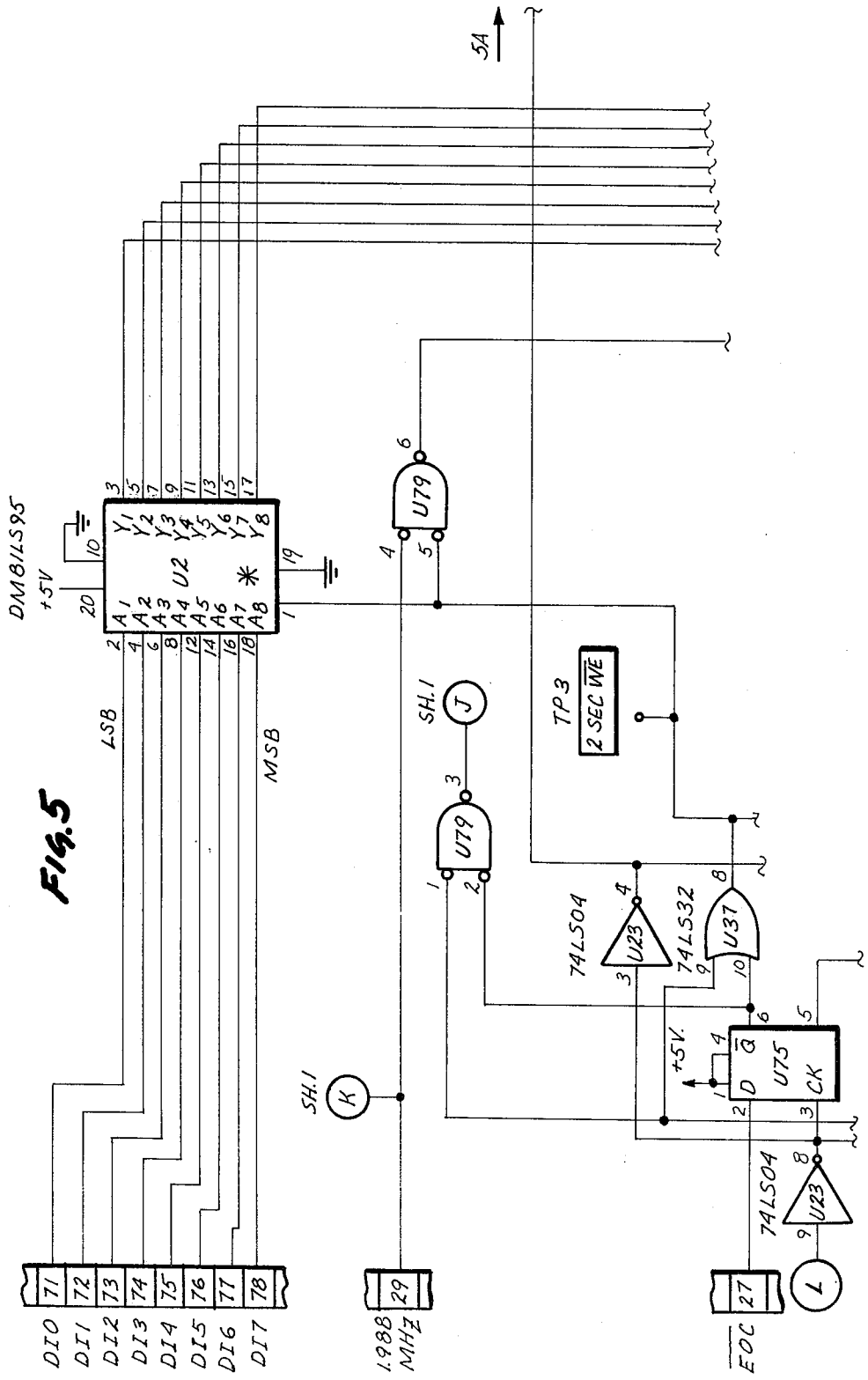

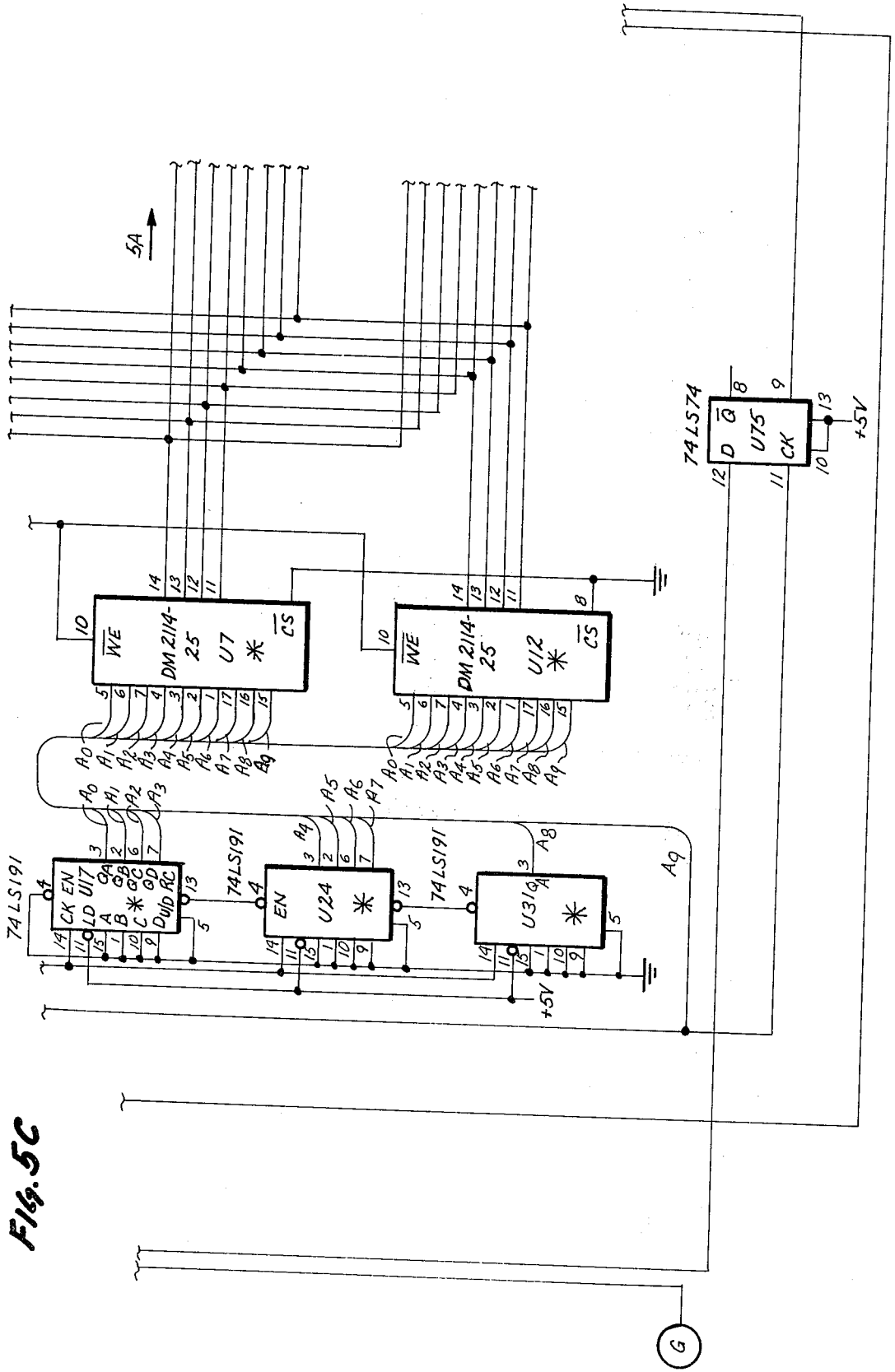

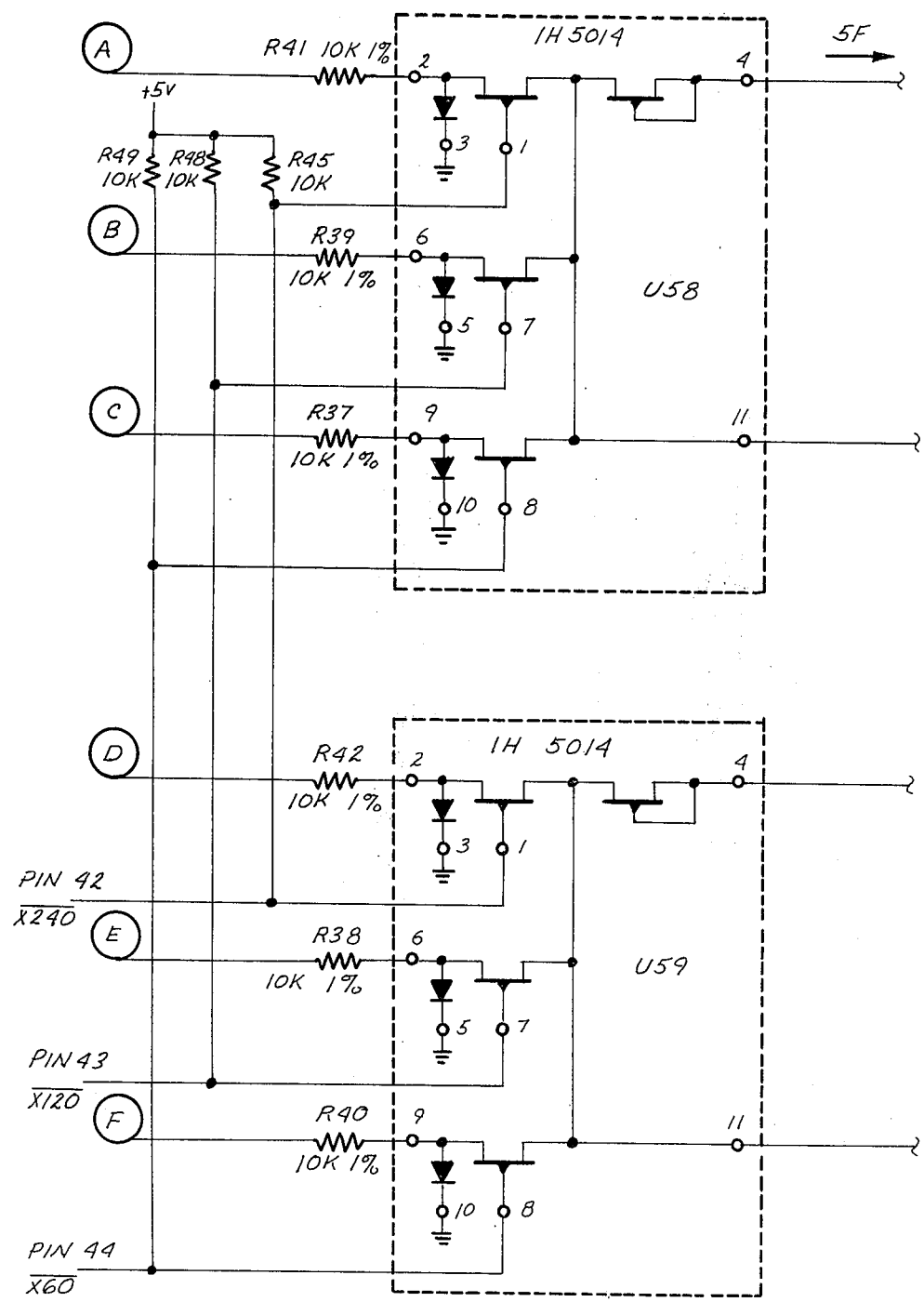

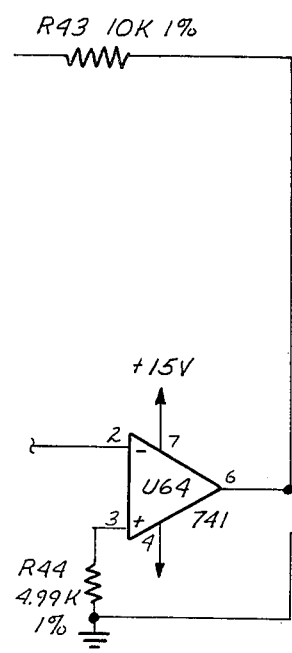
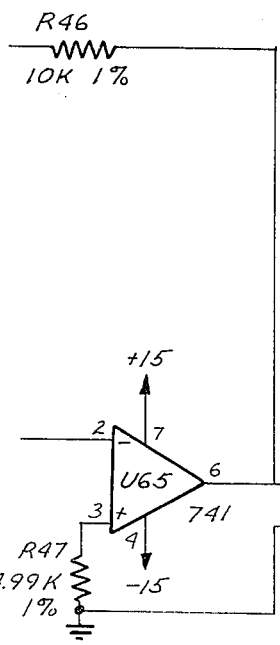
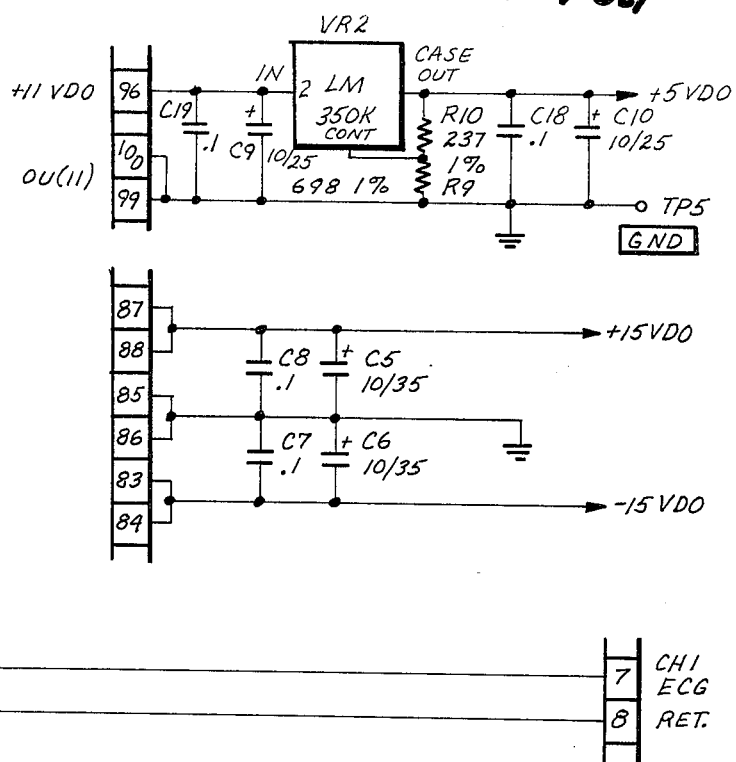

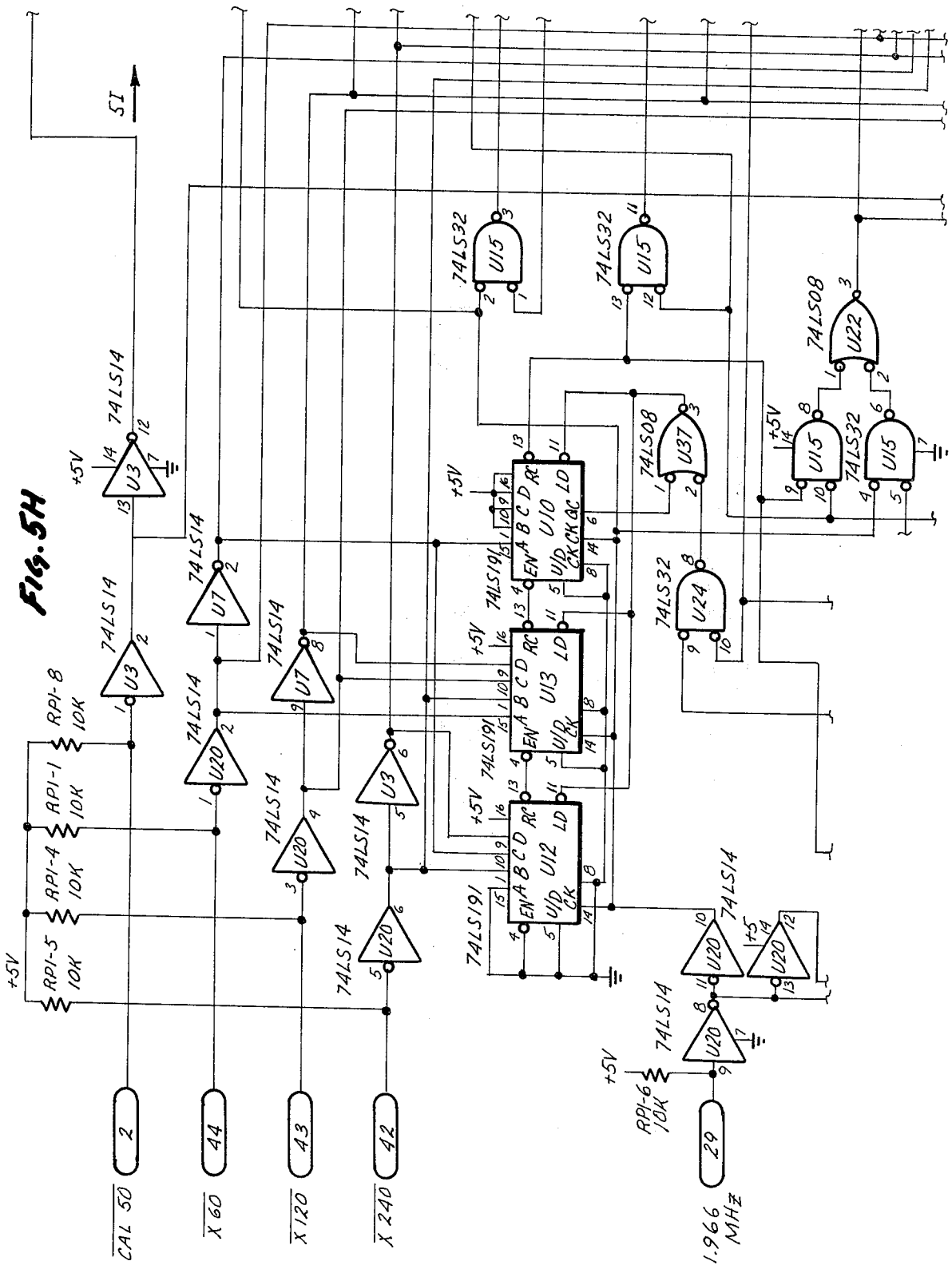

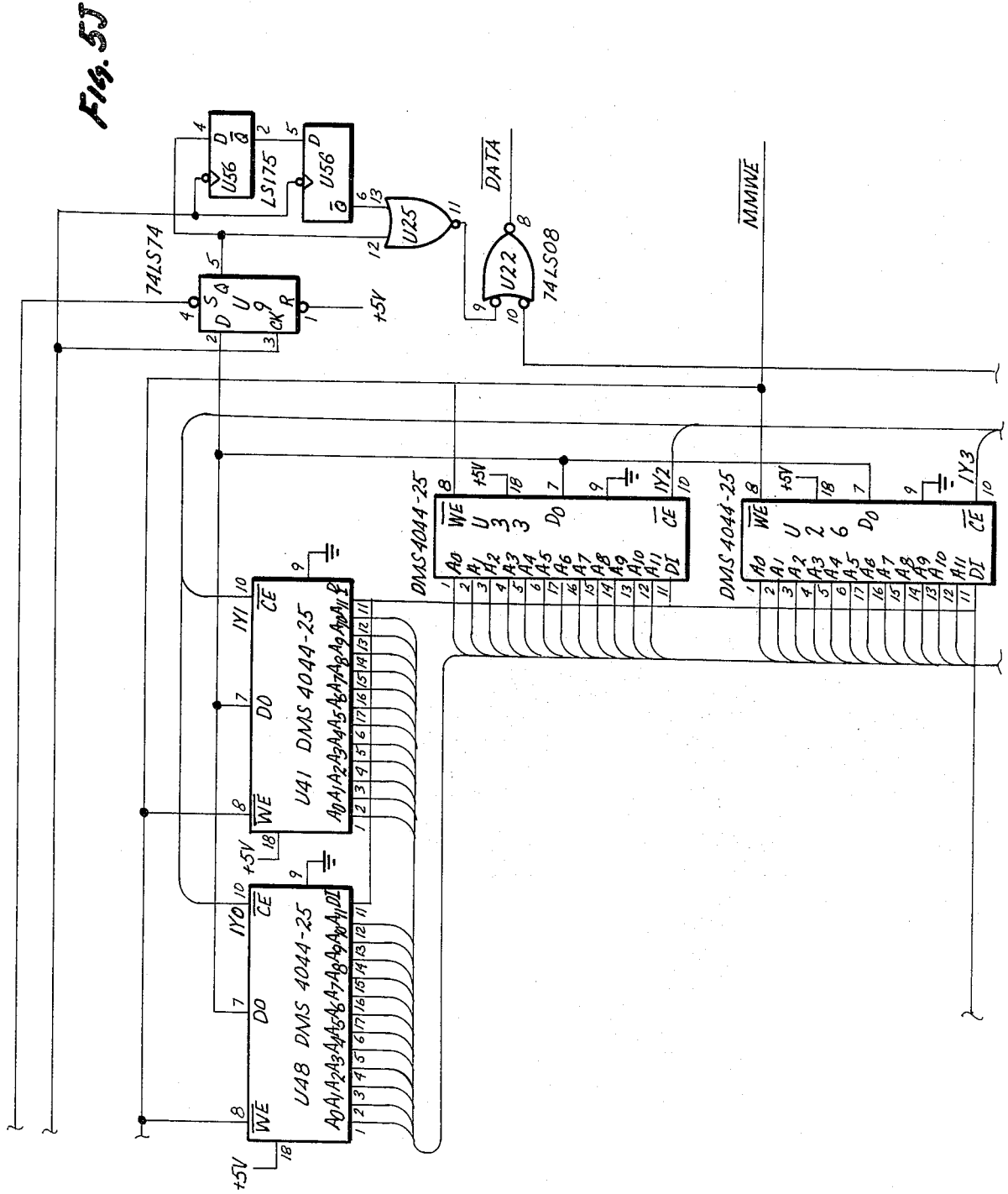

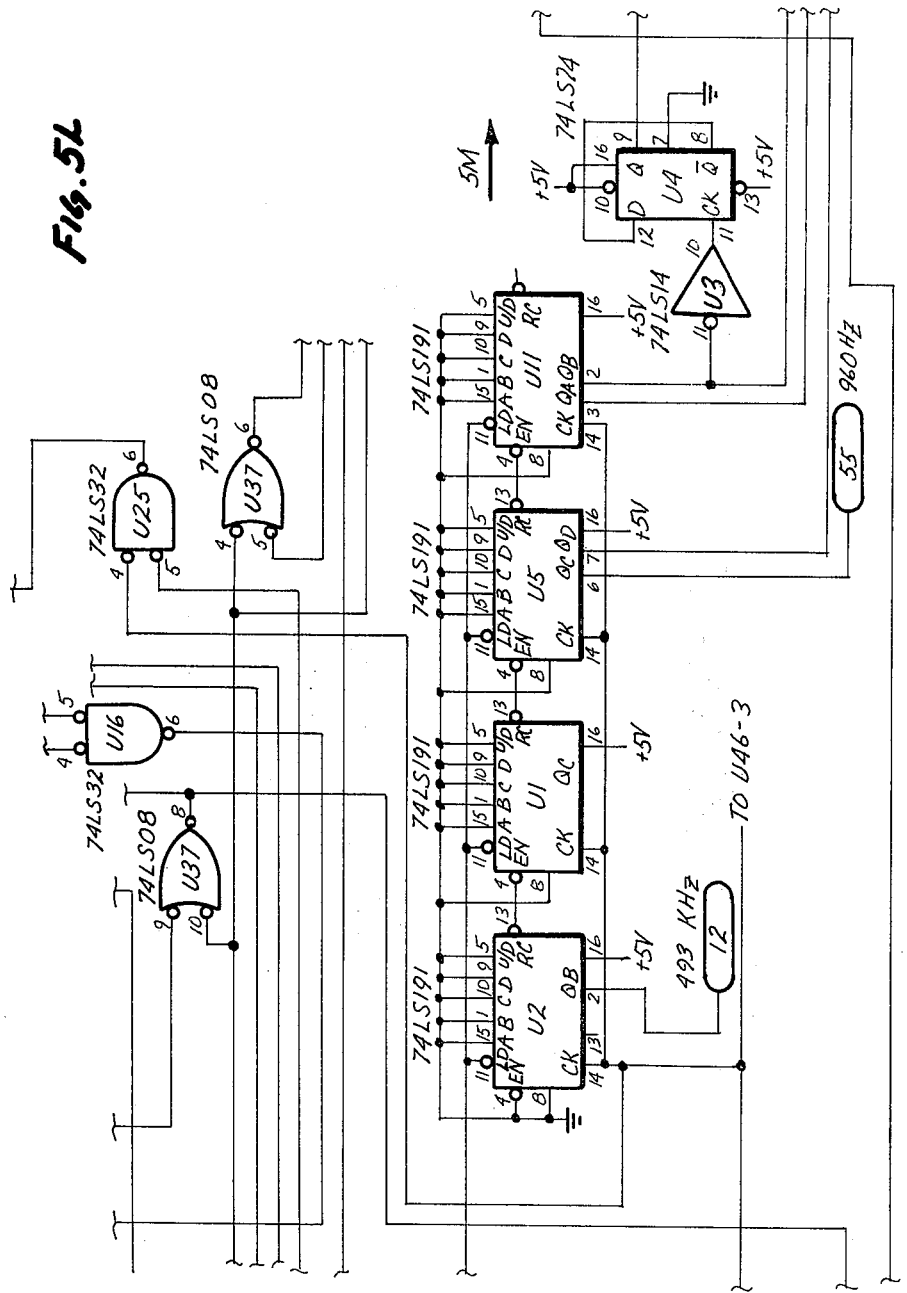

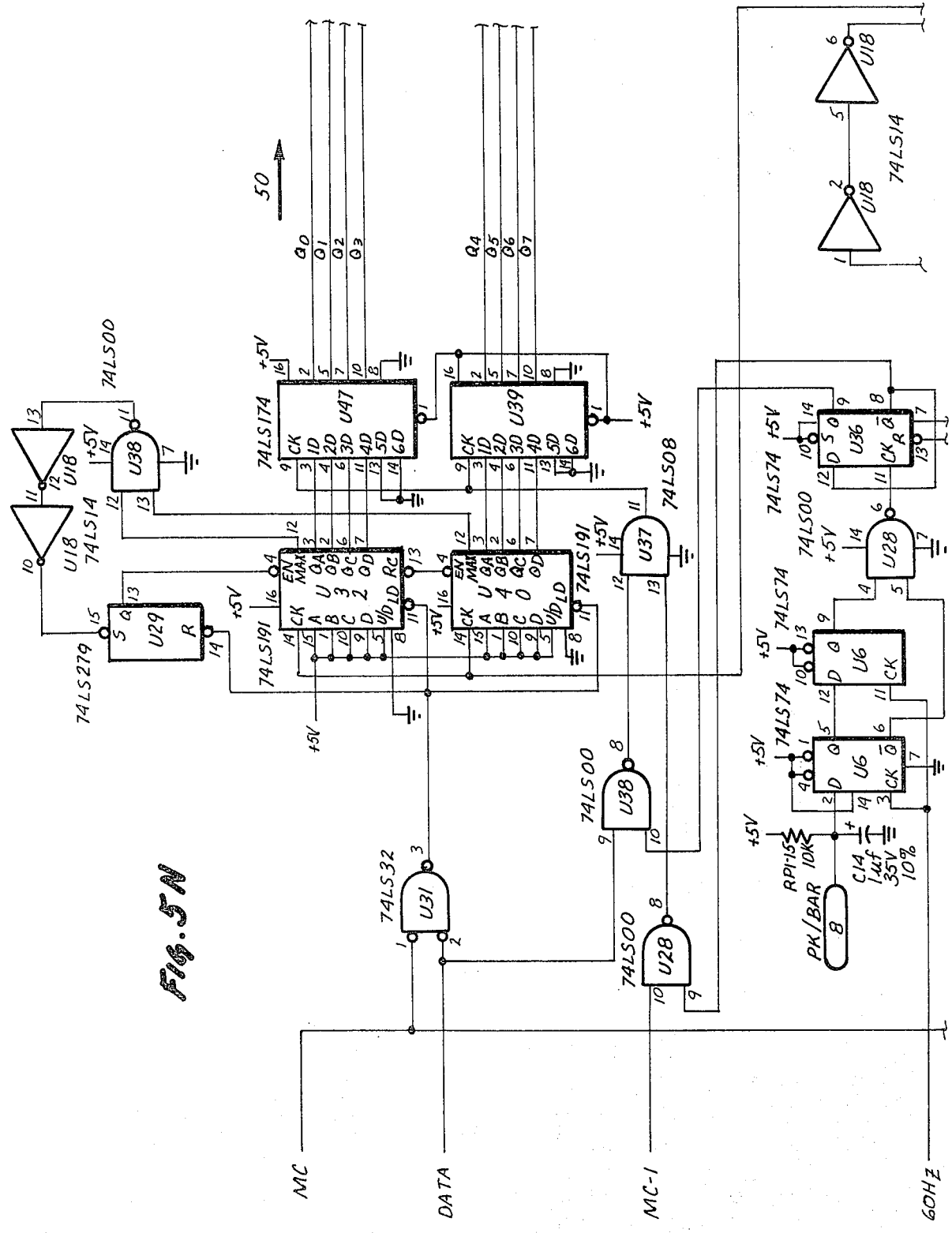

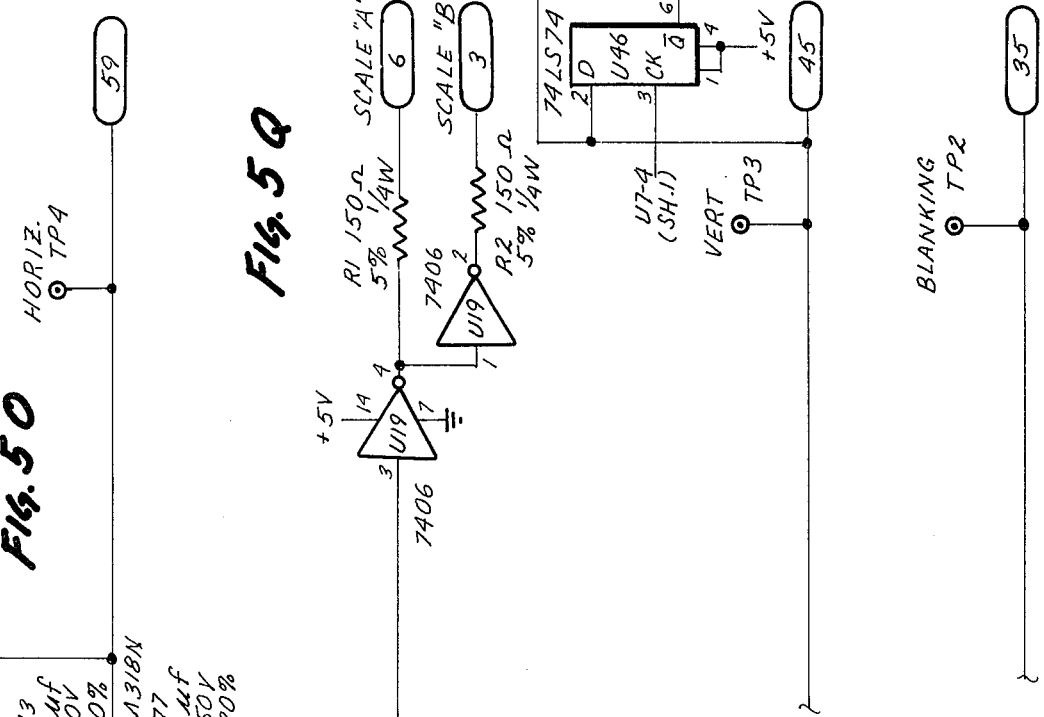
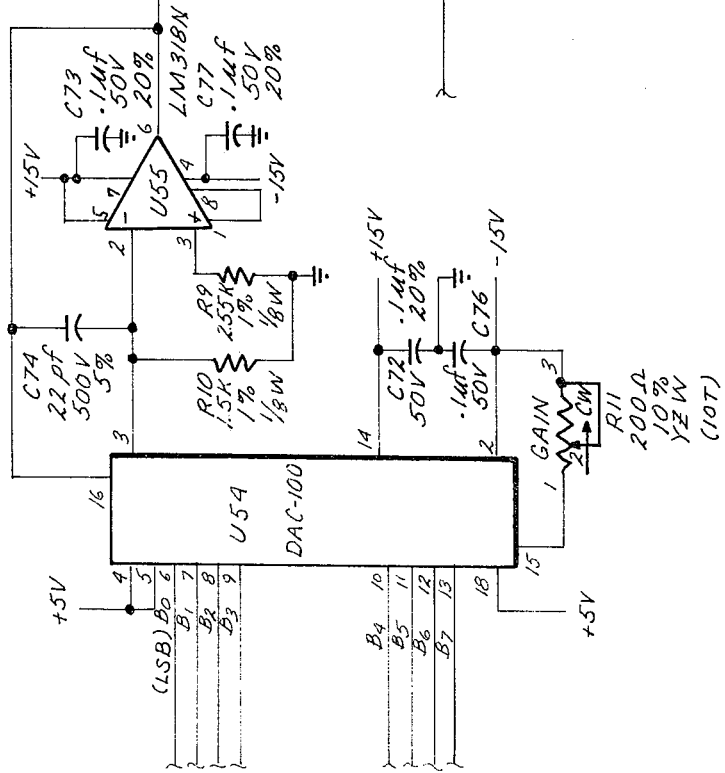
FIG. 5O
FIG. 5Q

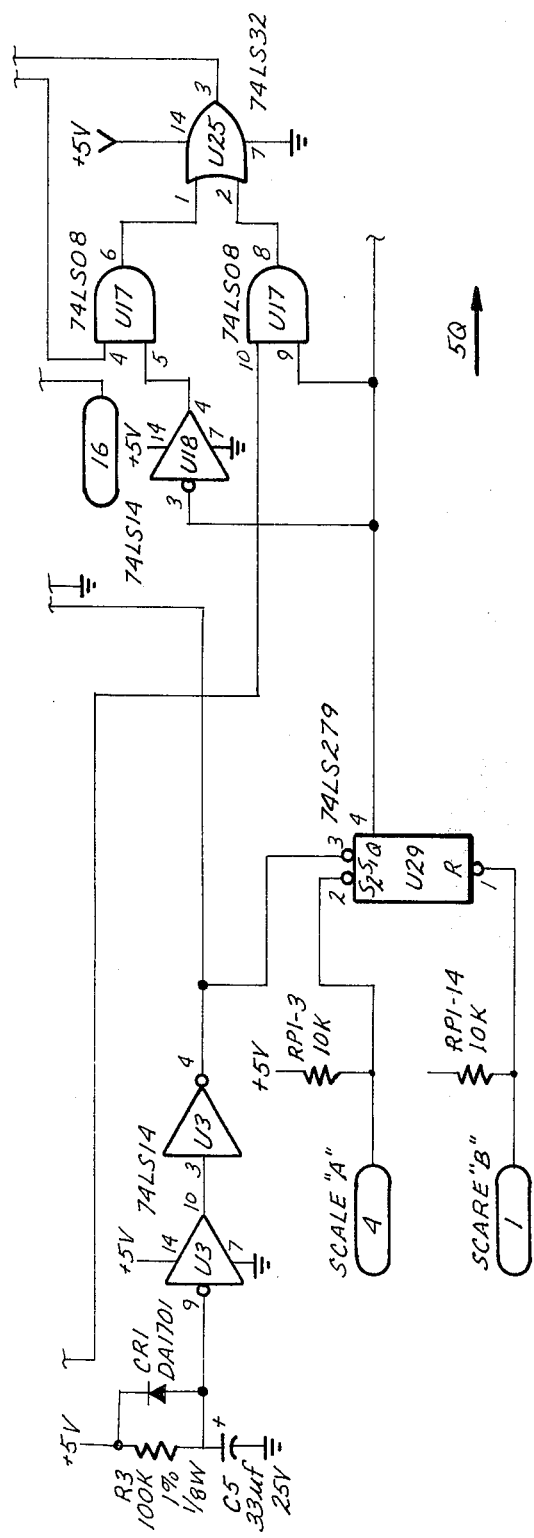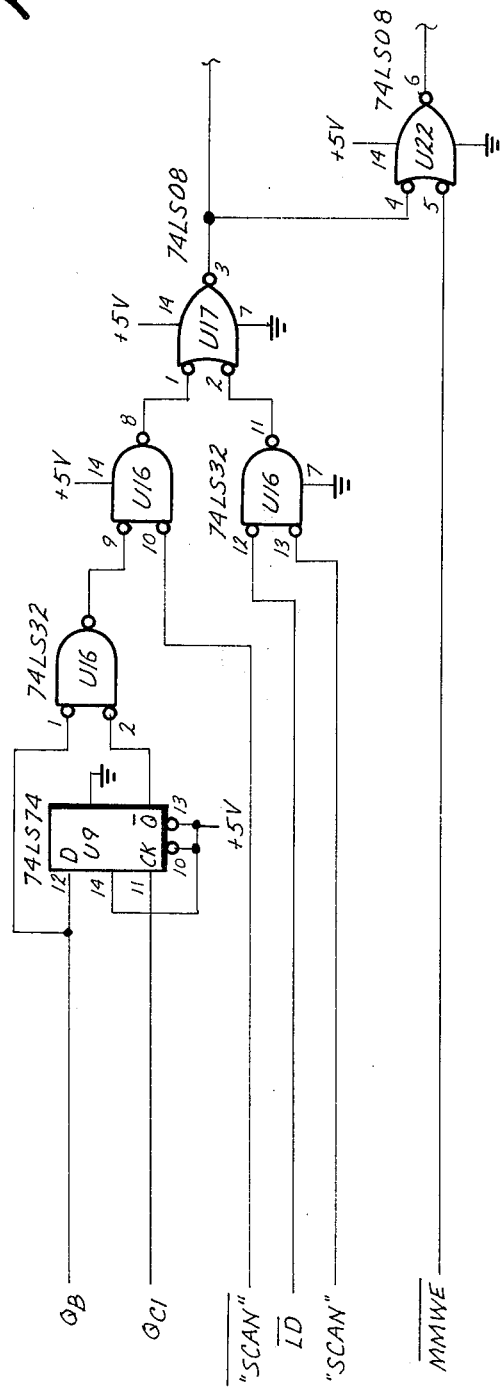
FIG. 5P

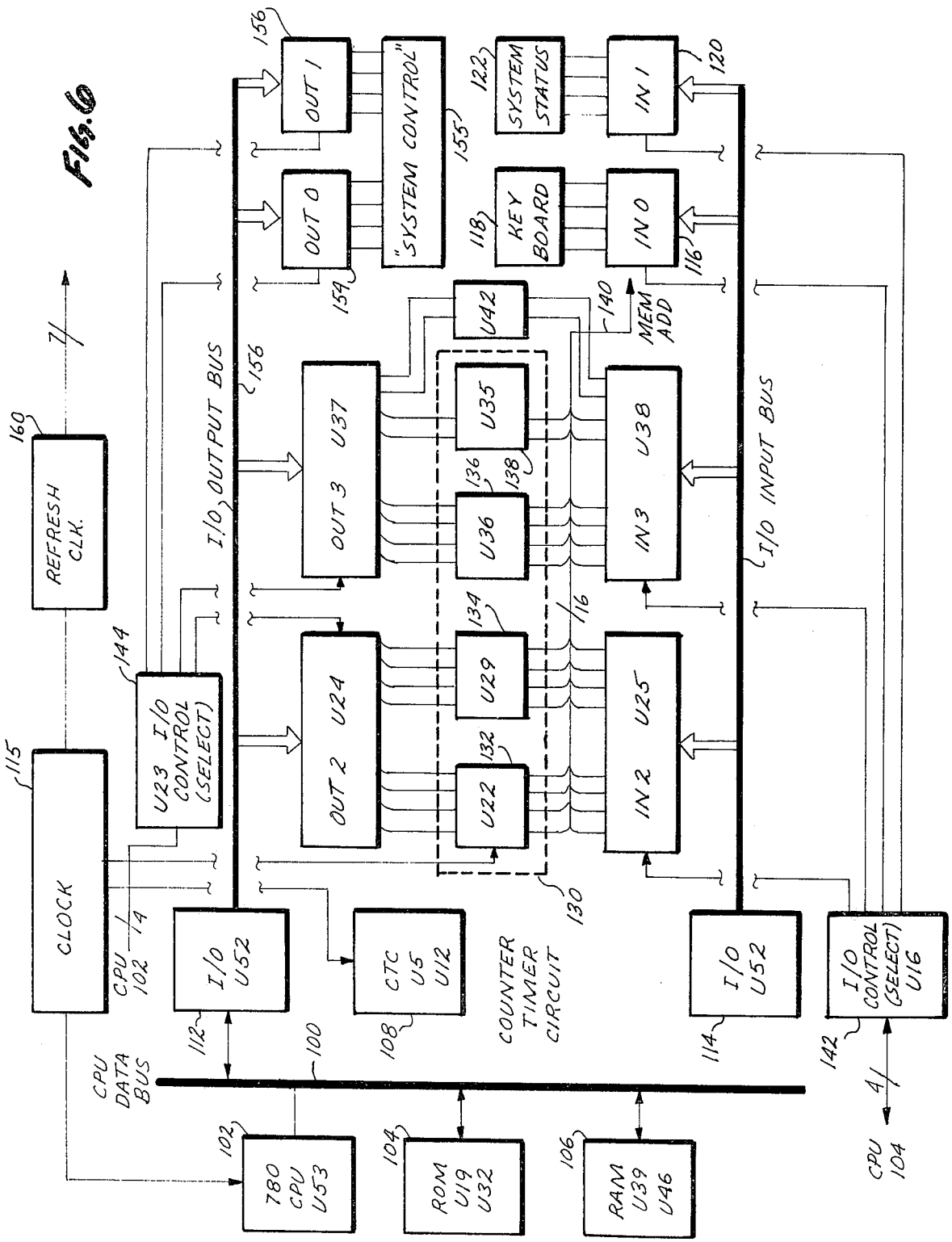

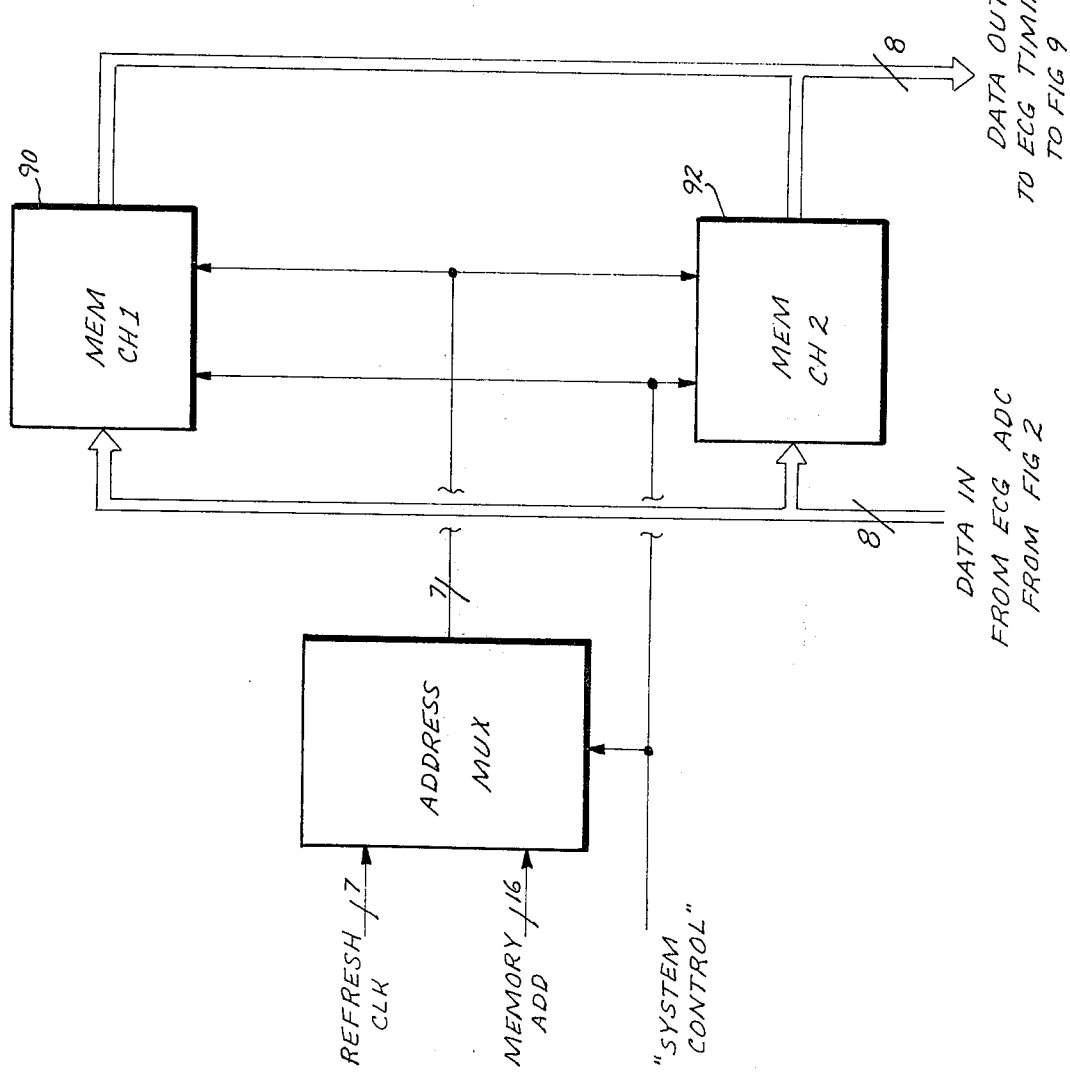

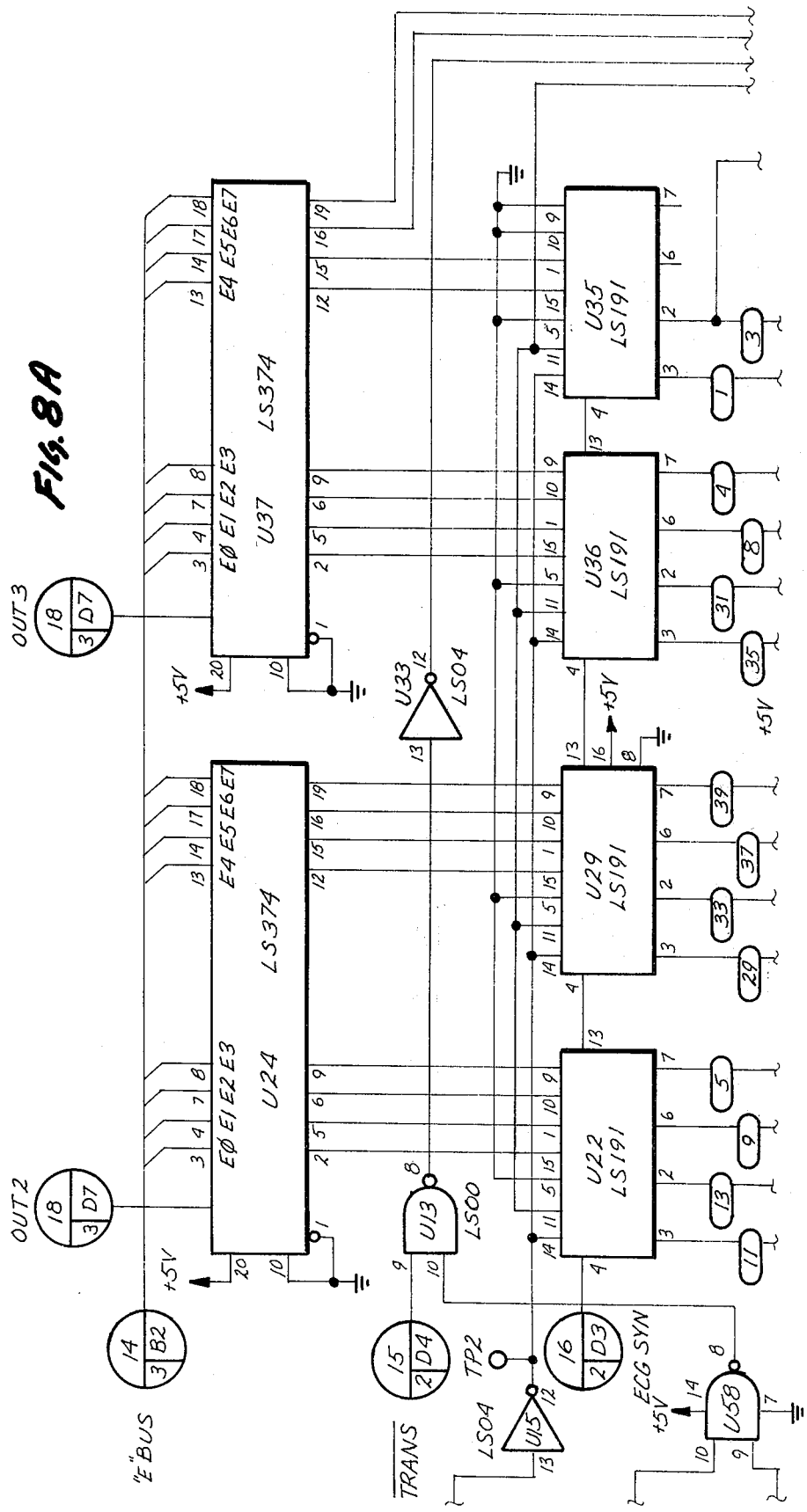

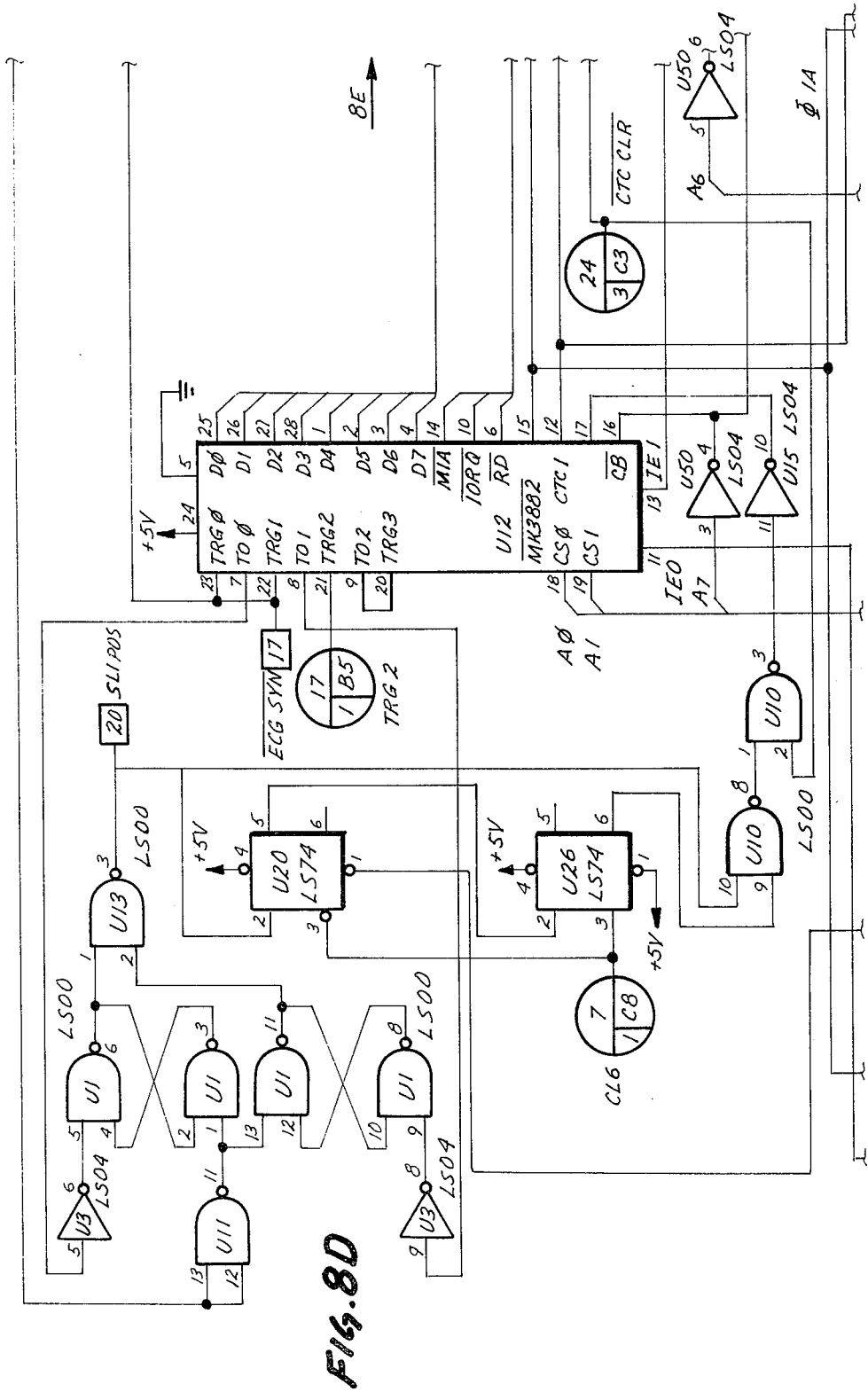

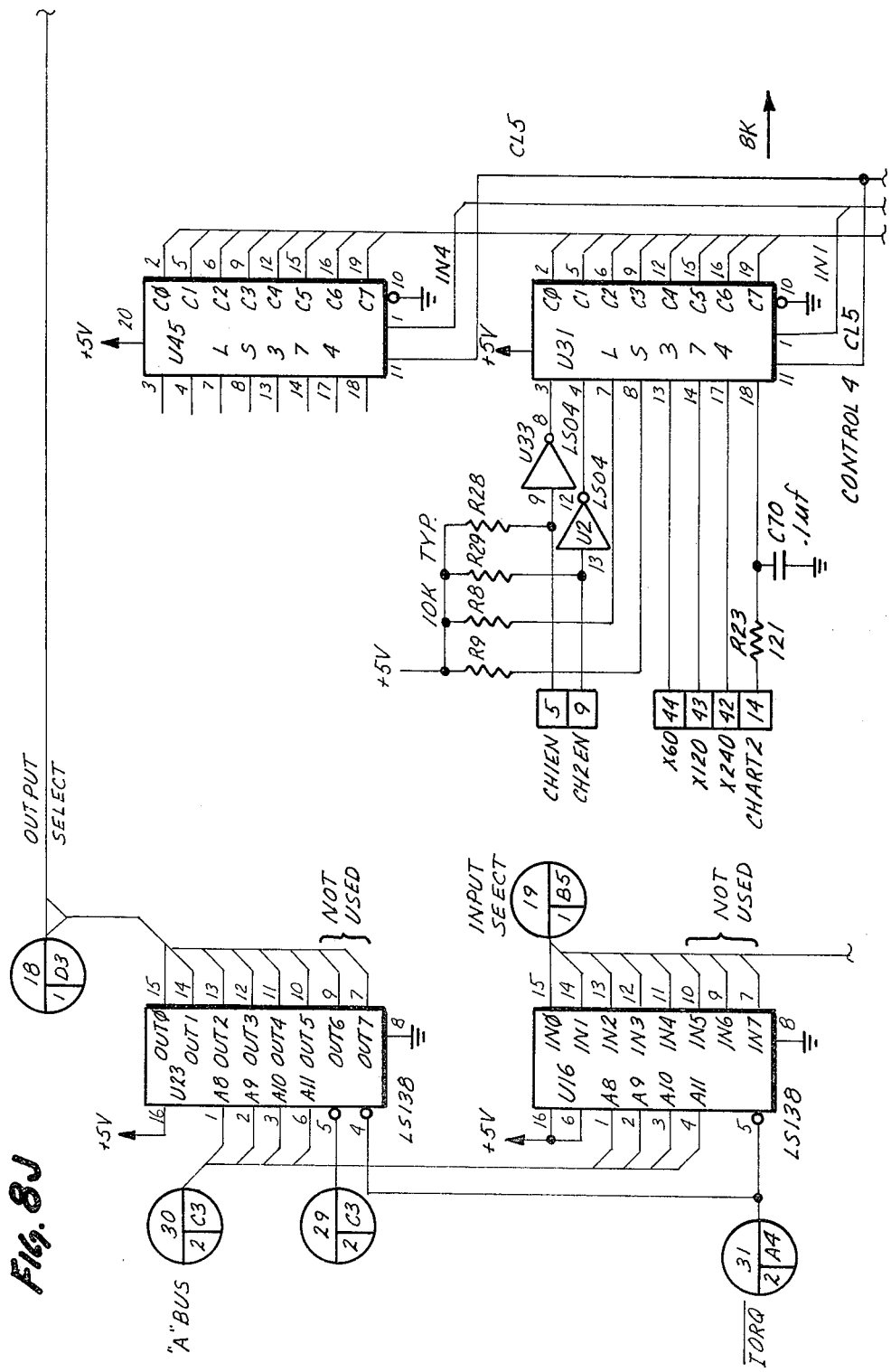

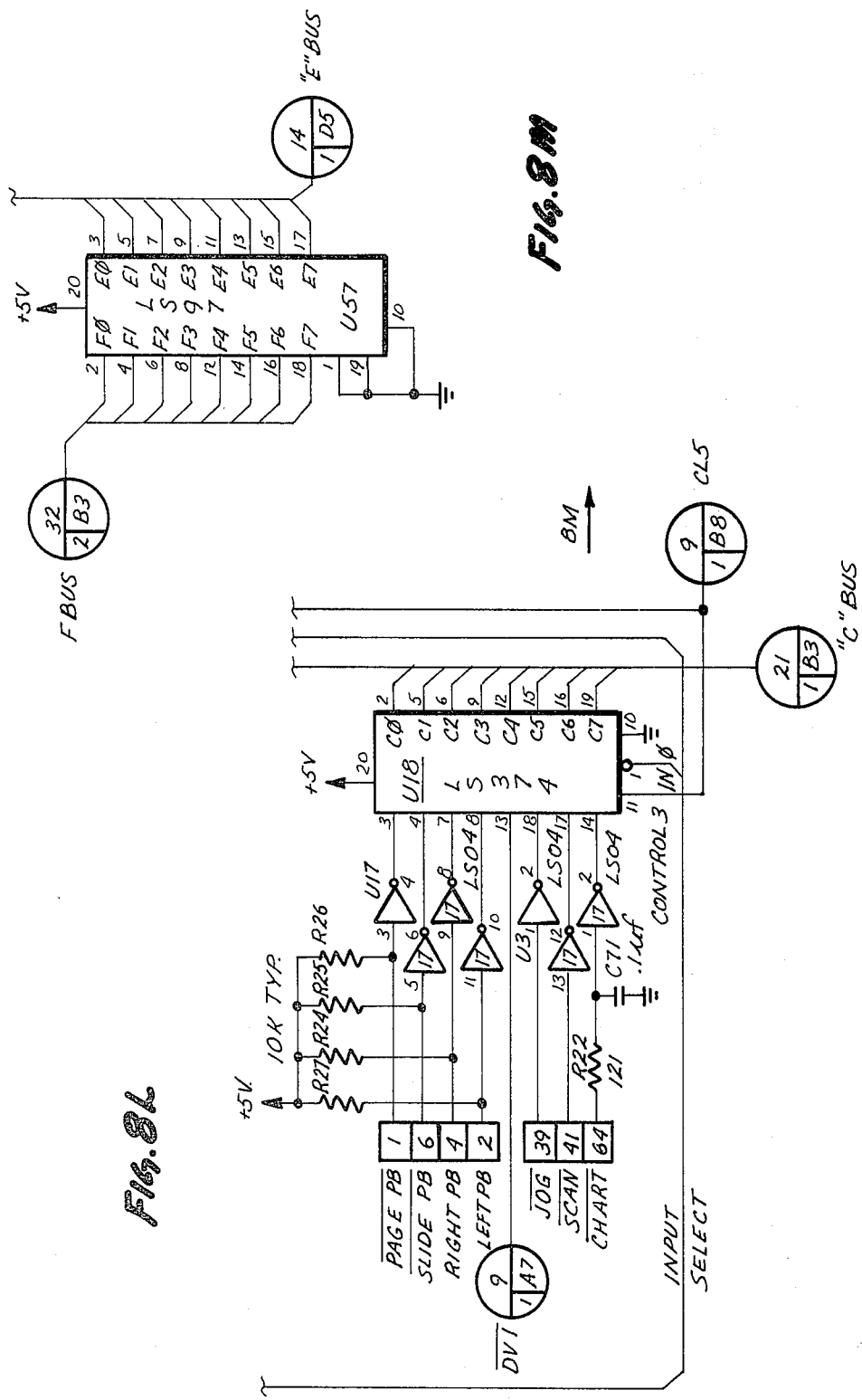

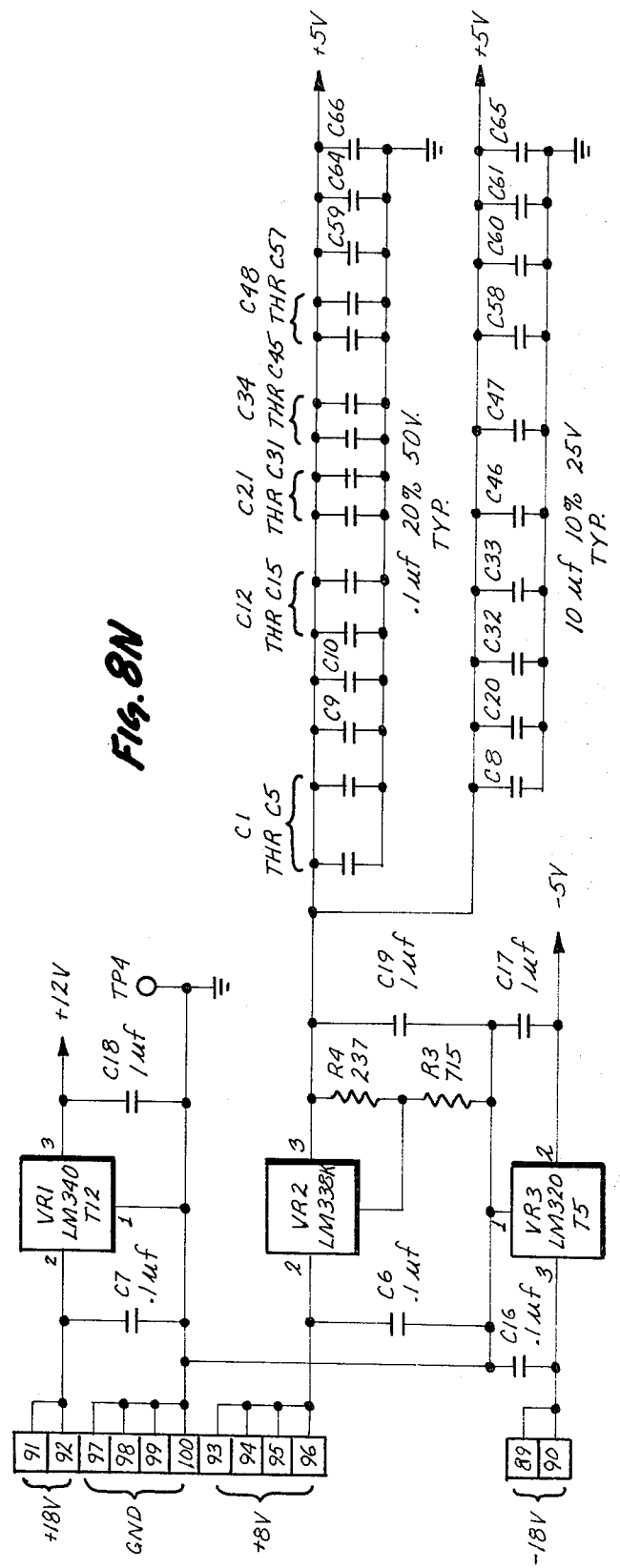

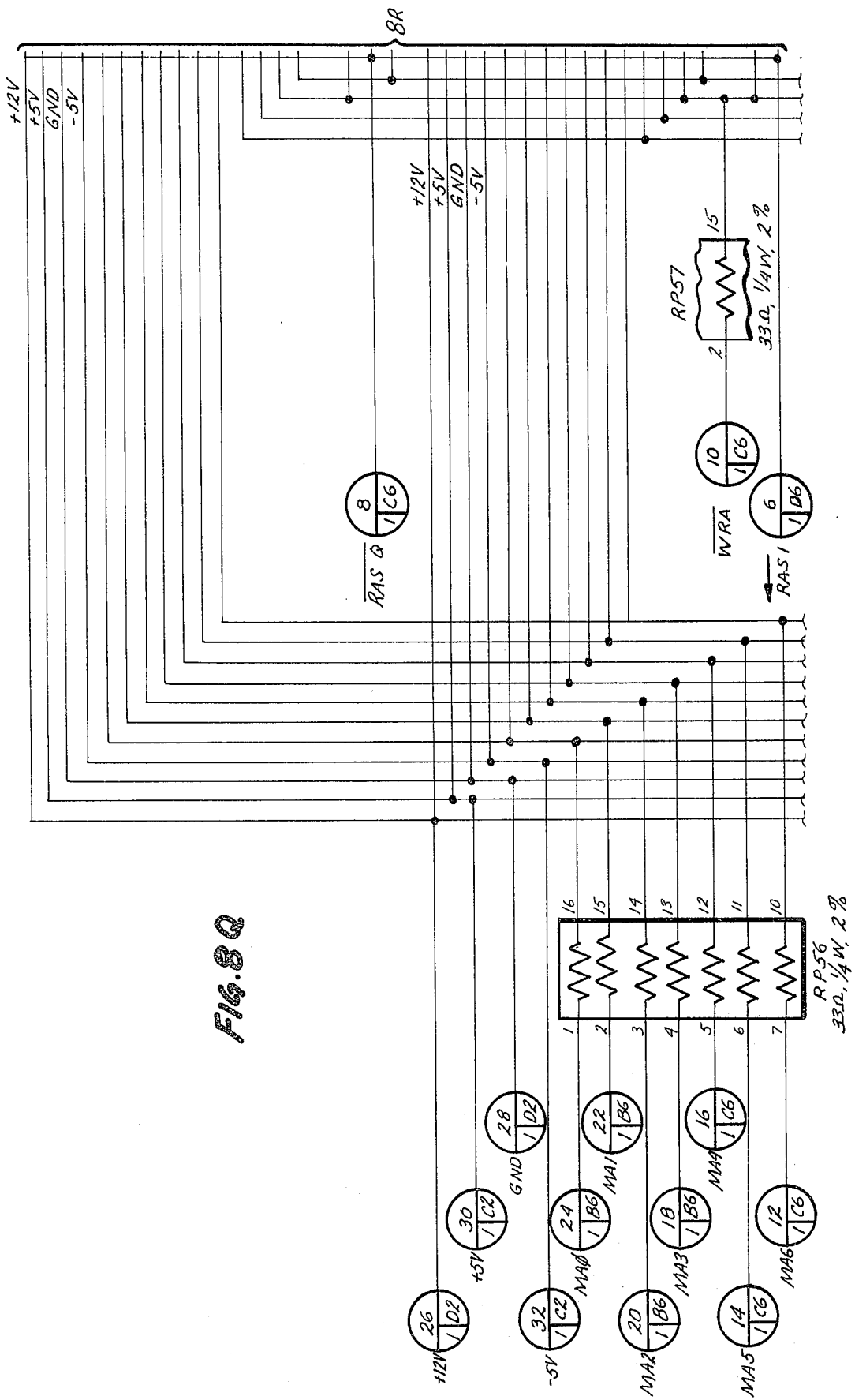

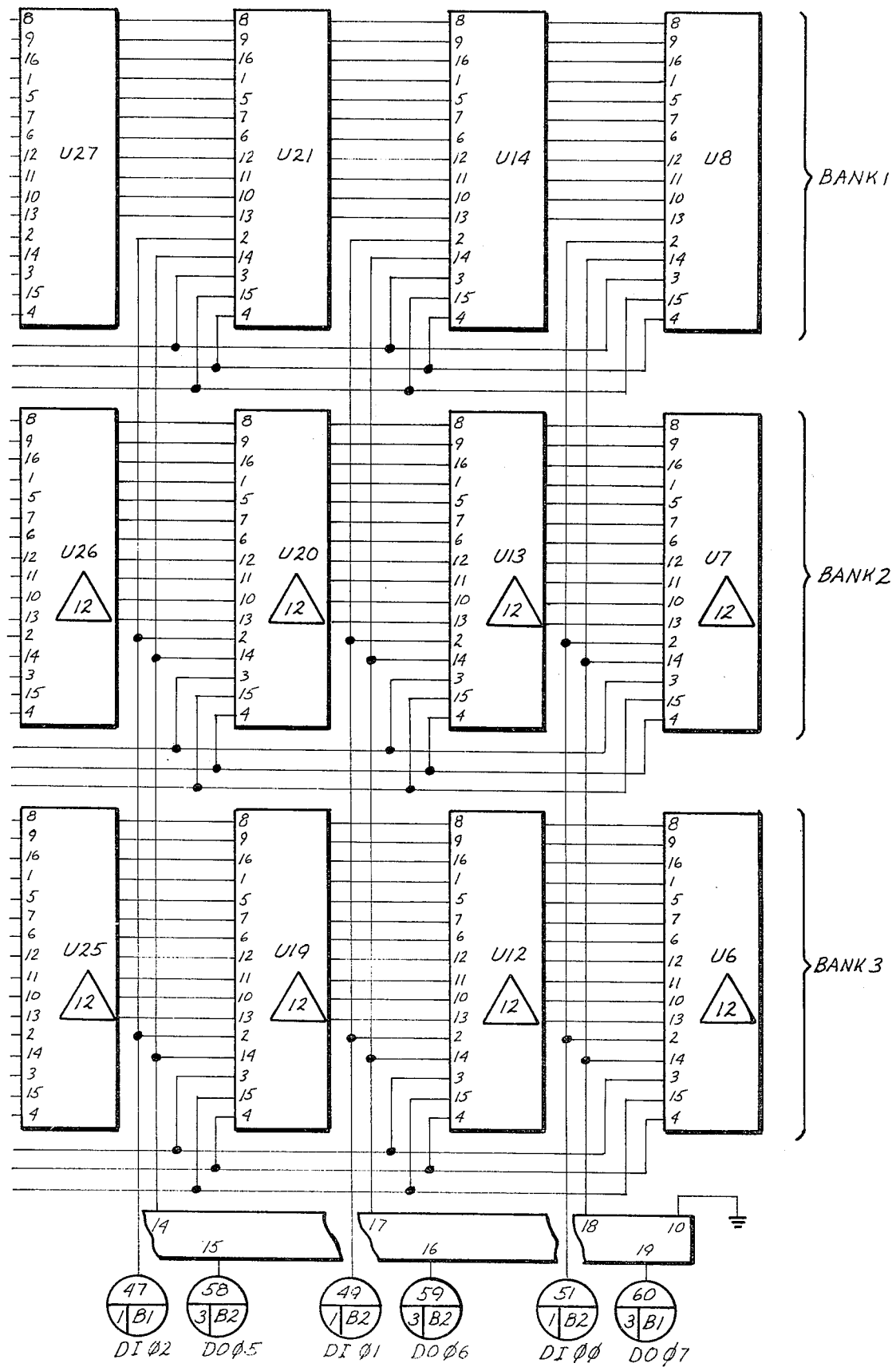

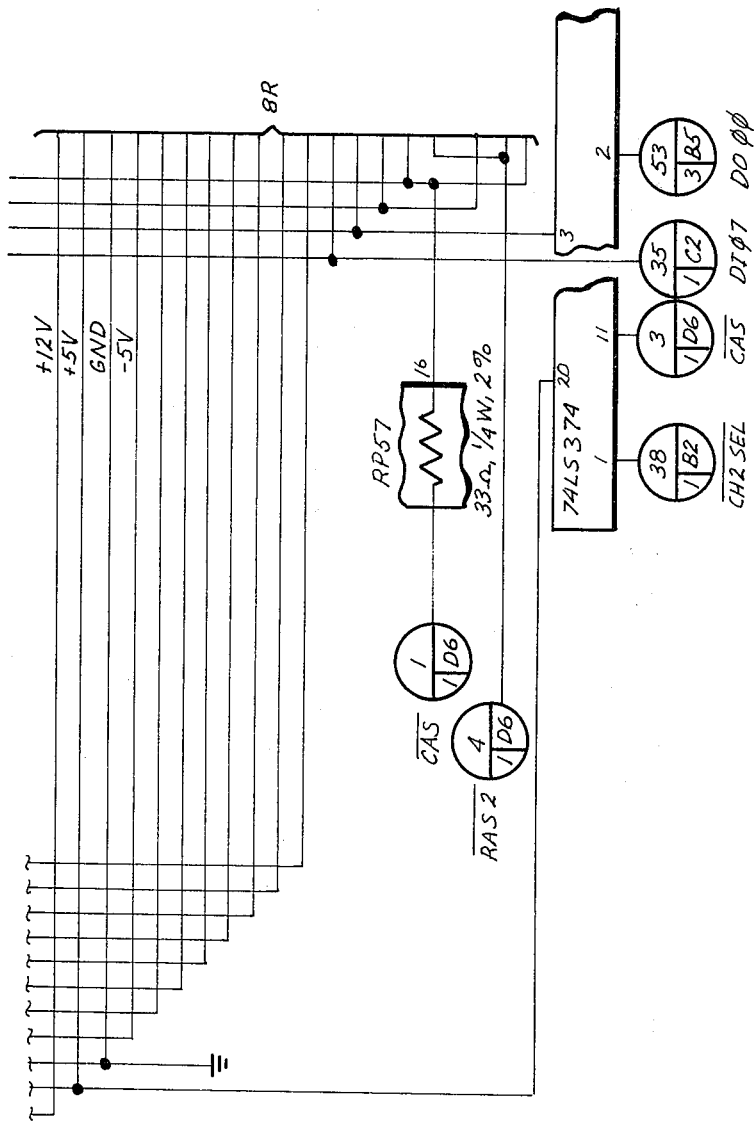

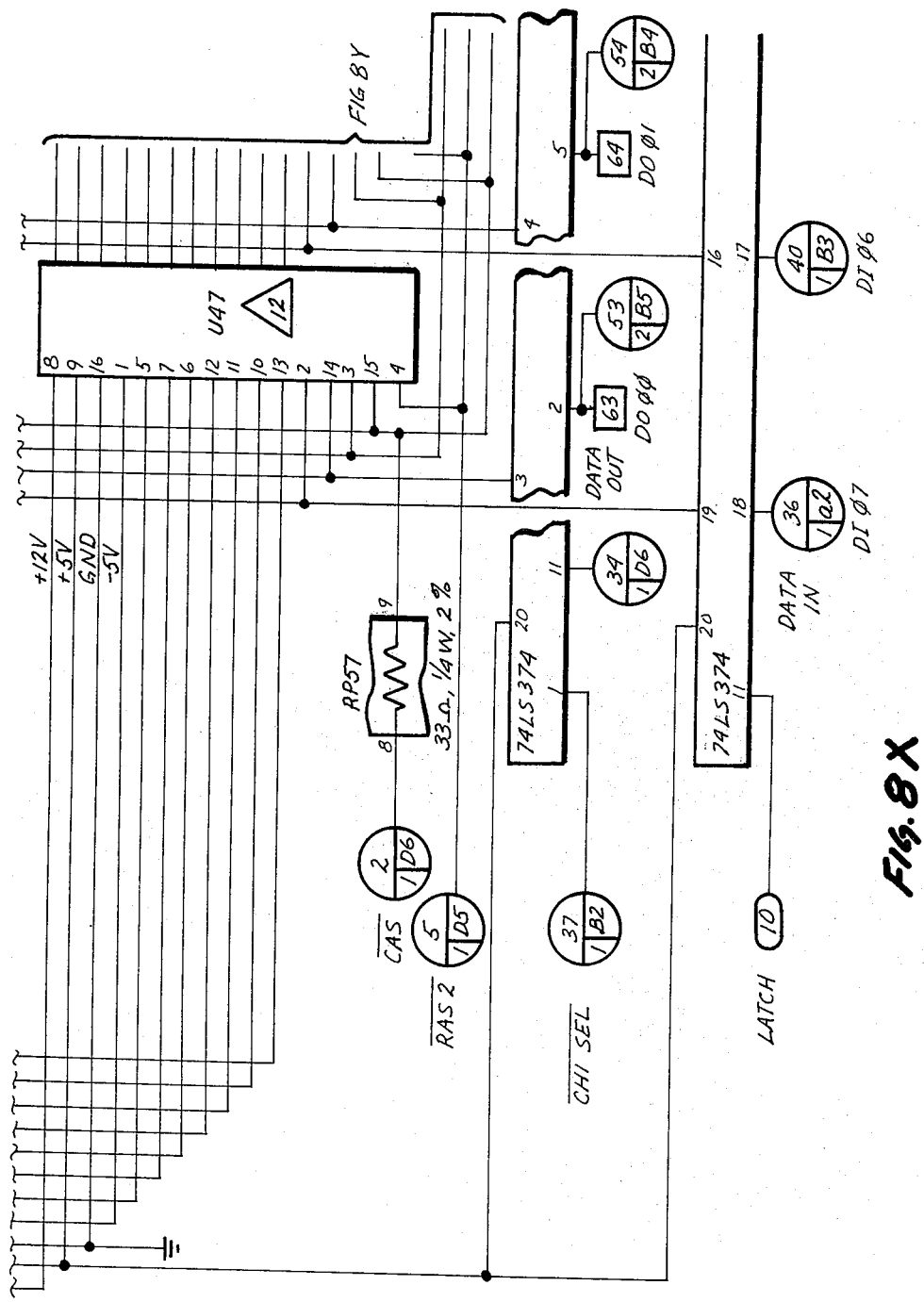

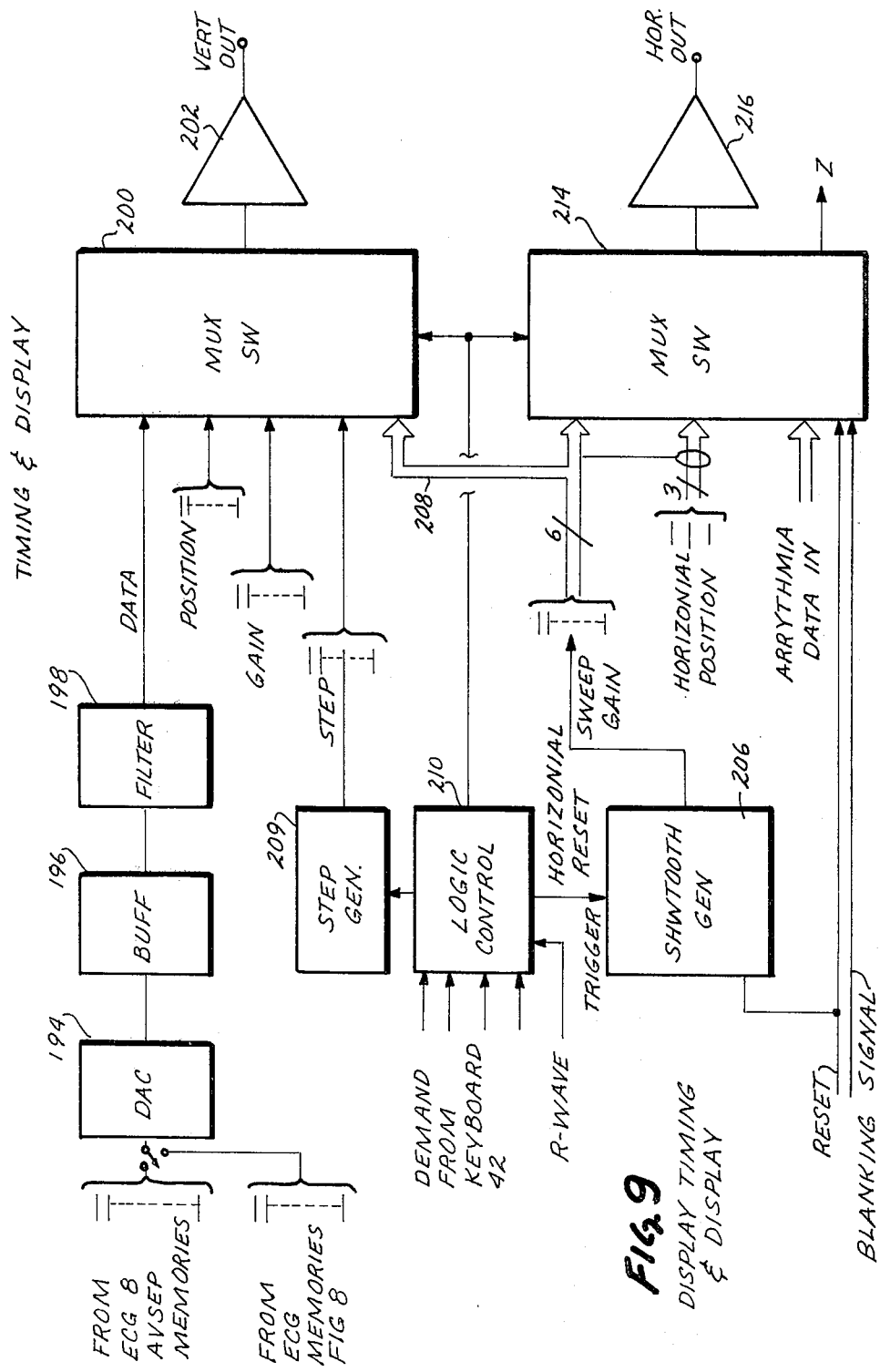

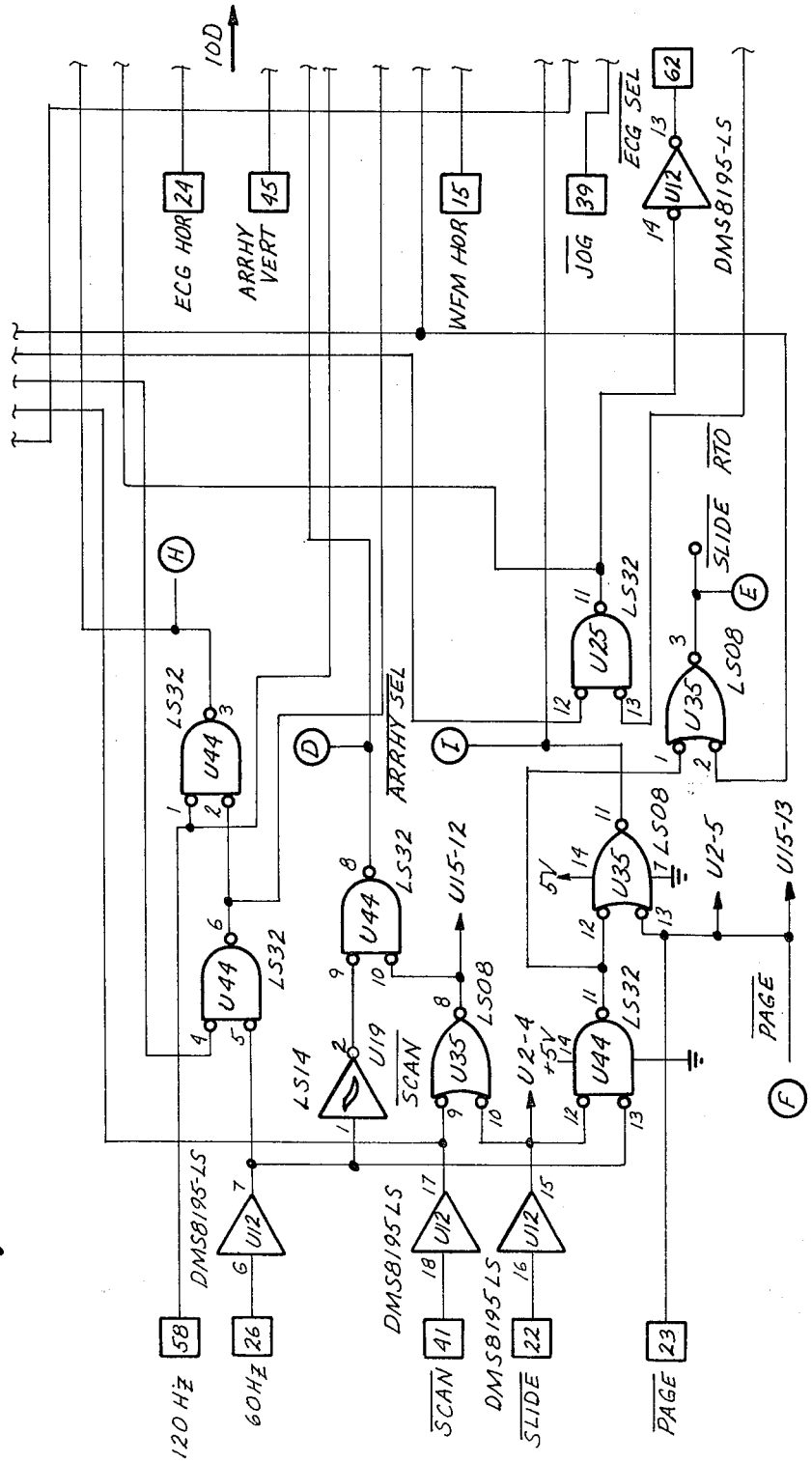

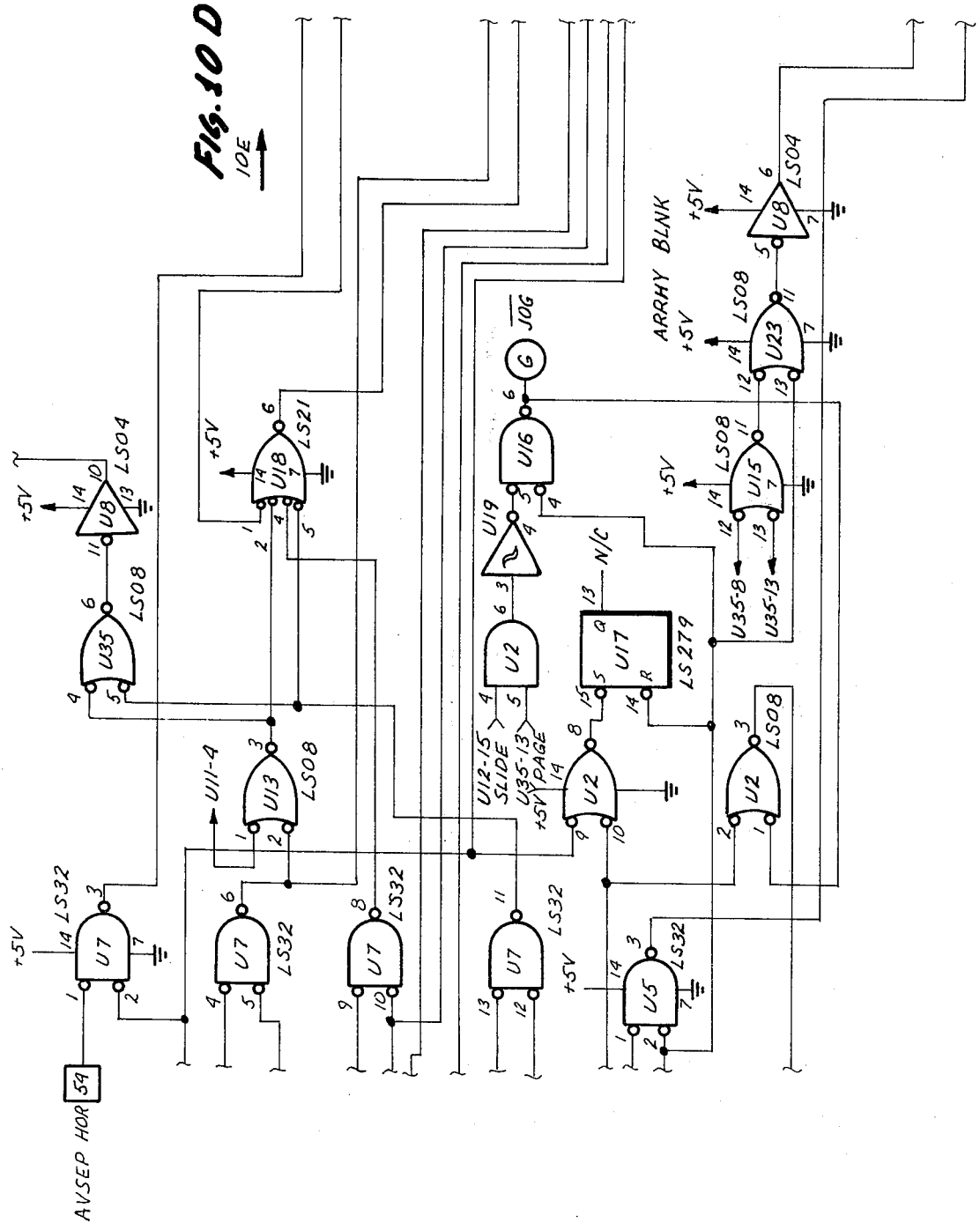

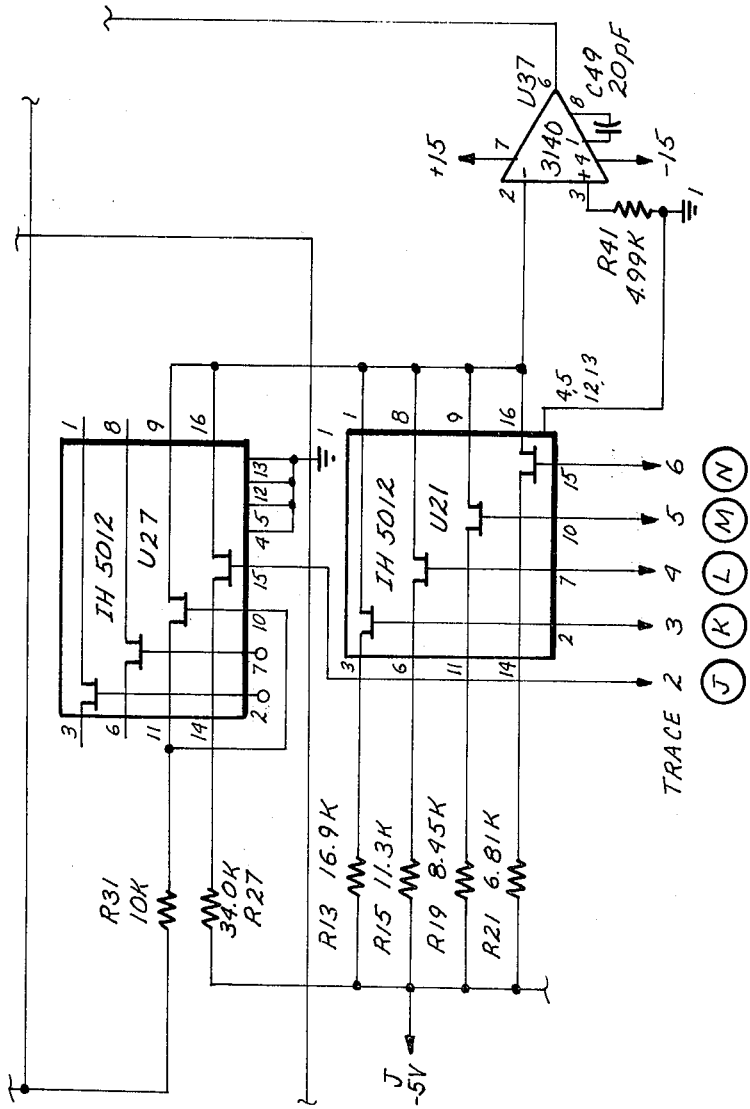

POWER UP AND RESET ENTRY POINT

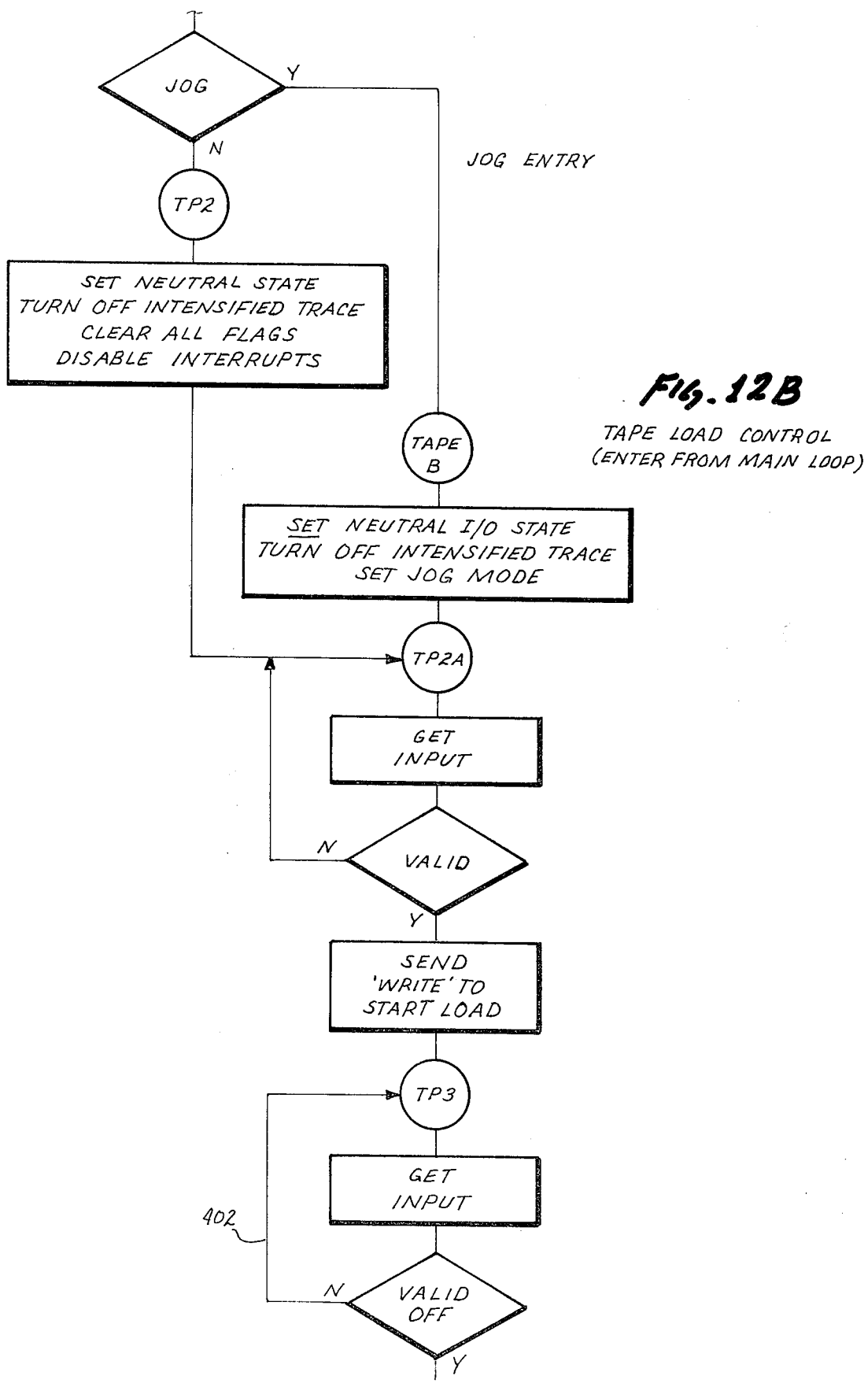

SLIDE DISPLAY CONTROL (ENTER FROM INTERRUPT CODE)

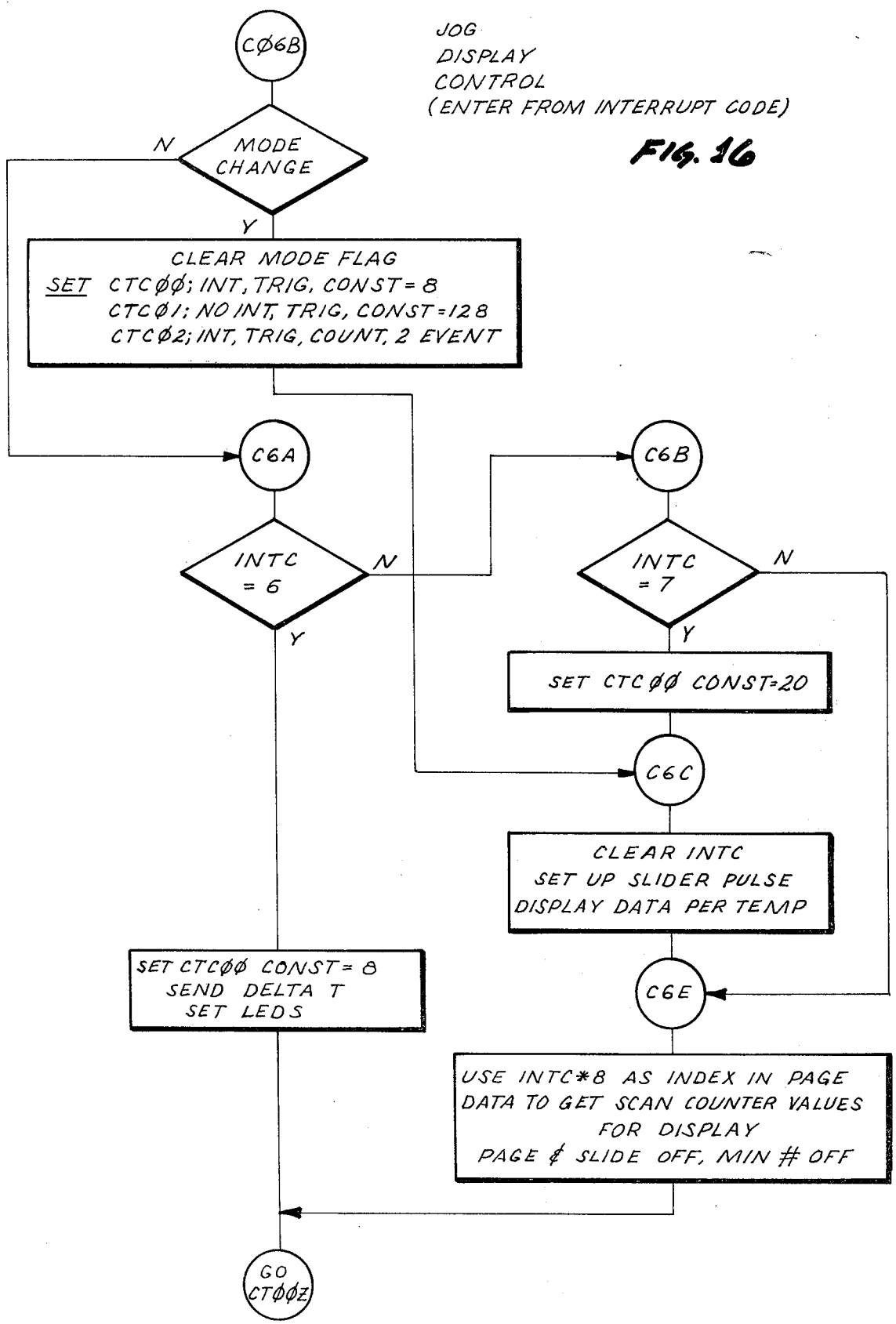

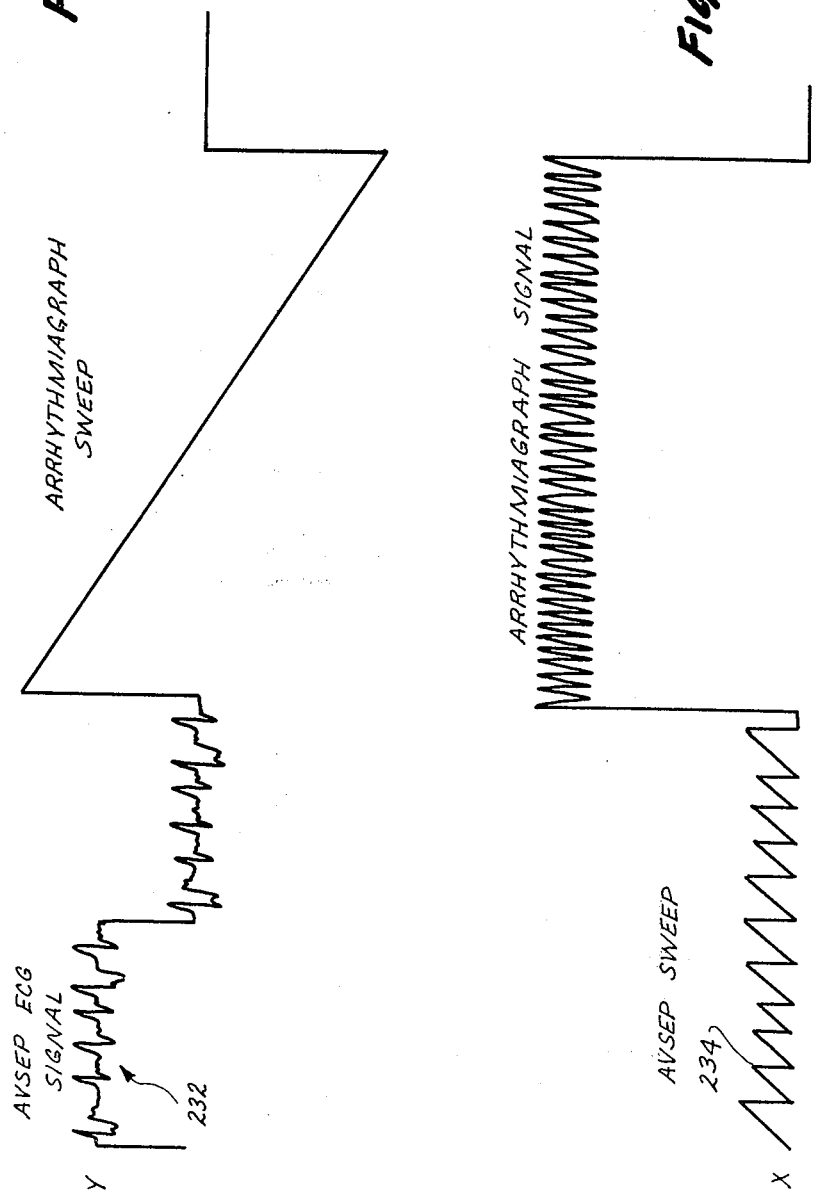

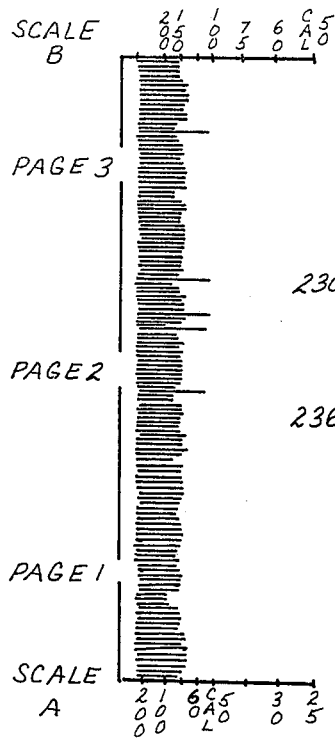
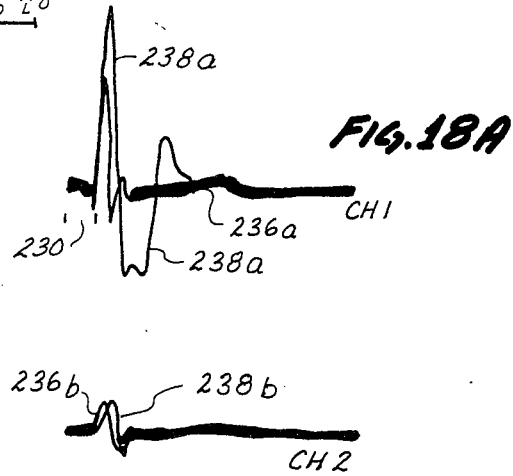
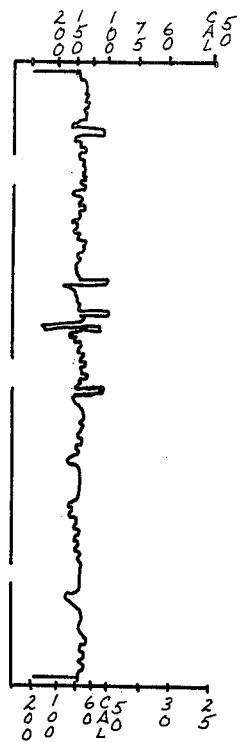
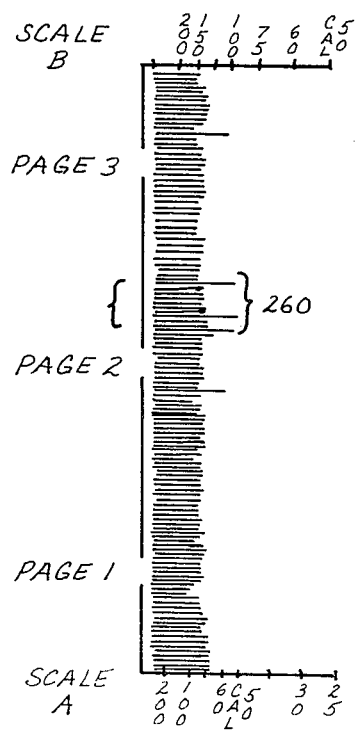

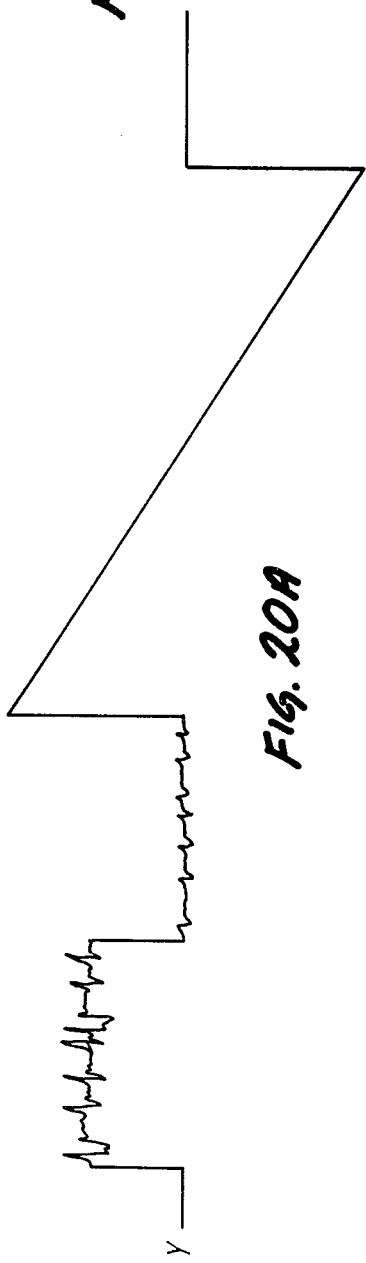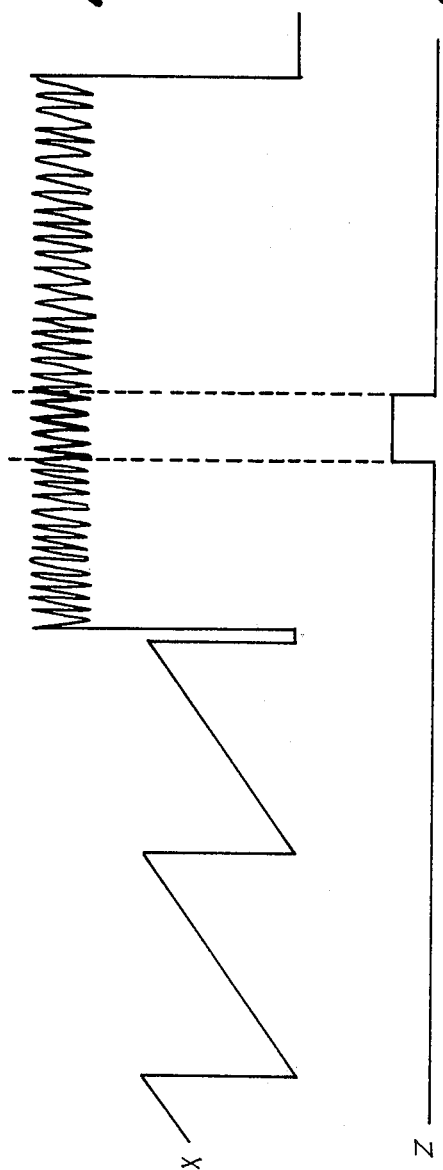
FIG. 20A
FIG. 20D
FIG. 20B
FIG. 20C

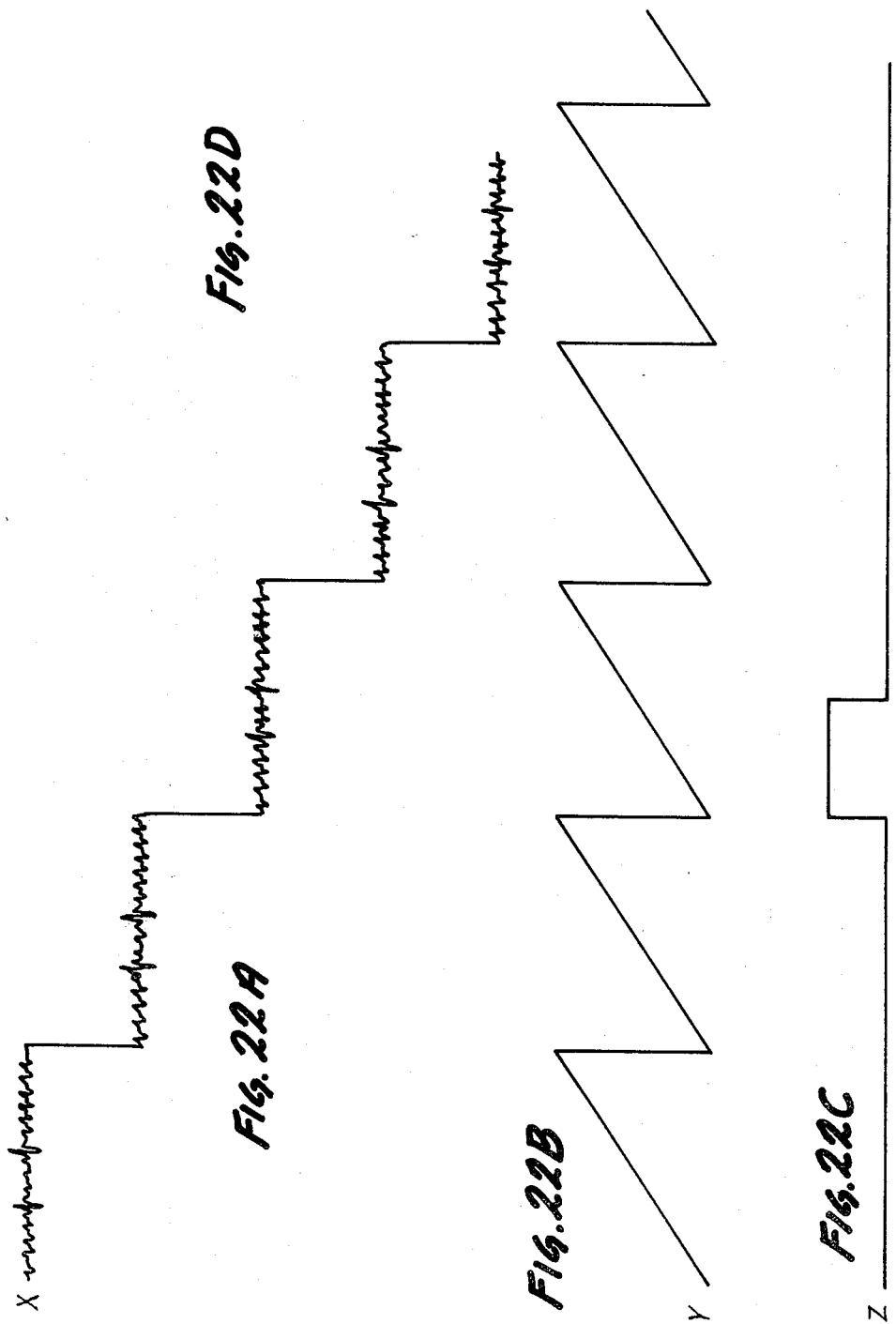

ELECTROCARDIOGRAPH COMPUTER DISPLAY SYSTEM

This is a continuation of application Ser. No. 192,600, filed Sept. 30, 1980, now abandoned.

CROSS REFERENCE TO RELATED APPLICATION

Cross reference is made to co-pending application entitled METHOD AND APPARATUS FOR ARRHYTHMIA ANALYSIS OF ECG RECORDINGS filed in the names of Donald L. Anderson, Isaac Raymond Cherry, John Allan Ripley, and David Teruo Tanaka, assigned to the same assignee, and filed Sept. 30, 1980 with Ser. No. 06/192,192, now U.S. Pat. No. 4,336,810.

BACKGROUND OF THE INVENTION

The present invention relates to an electrocardiograph computer display system, particularly adapted for the visual display and automatic processing of large volumes of electrocardiac signals and enabling the permanent recording and analysis of such signals in a relatively short period of time.

Electrical signals that appear at a person's skin as a result of the electrical activity of the heart are known as ECG signals. These ECG signals exhibit particular wave forms which correspond to the action of the heart muscle and reflects both in timing and in character the condition of the heart. It is well-known to place electrodes on the patient's skin to sense the ECG signals and to present them for visual analysis, either in real time or in a subsequent time for use by physician is the analysis over an extended period of time of a continuous ECG signal which reflects heart activity during the normal activities of the patient and which displays anomalous heart signals which represent arrhythmic and ectopic activity. As used herein arrhythmic heart activity includes activity which is abnormal, such as irregular variations in rhythm and ectopic activities, such as premature ventricular contractions, ventricular ectopic beats, and supra ventricular ectopic beats. More especially, it is desired to accumulate and analyze large volumes of such ECG signals during normal activities of the patient, as for example, over a twenty-four hour period, and to review this accumulation in a highly accelerated mode using a visual display to determine the frequency and character of the various heart signals and to identify those which are of particular interest. For this purpose there are known systems which accomplish the foregoing by recording the ECG signals in real time on a small compact tape recorder, which is worn by the patient. The recording signals are then processed by replaying the same at a much faster speed with a displayer presentation of the signals on a cathode ray oscilloscope in which each ECG complex is superimposed on predecessor complexes. This type of display is known as an AVSEP display and the description of such is set forth in U.S. Pat. No. 3,215,136 issued Nov. 2, 1965 in the name of Norman J. Holter, et al. The scanning device of U.S. Pat. No. 3,215,136 utilizes superimposition of the ECG signals from two different tracks of a magnetic recording tape. In playback the signal from one track was used to trigger an oscilloscope trace of the signal from the other track. Oscilloscope screen persistance permitted the superimposition of successive signal complexes. A subsequent improvement is set forth in U.S. Pat. No. 3,718,772 issued Feb. 27, 1963 in the name of Clifford Sanctuary which provides for the use of a single track magnetic tape recorder wherein trigger signals are produced by a separate trigger head scanning a single track of the magnetic tape recording. U.S. Pat. No. 4,157,571 issued June 5, 1979 to Stephen K. Shu discloses an improved scanner in which the tape is received at high speed by an operator, who is also able to stop the display and initiate real time, single frame viewing modes in which a segment of tape is repeated, an interval of the signal thereon representing a frame stored in a digital memory, thus the content of memory can be displayed in real time for analysis by the operator and a selected print-out can be obtained as desired.

The various display systems set forth in the above referenced patents include recording the same ECG signal on two tracks of a recording and developing a trigger signal from the rising edge of the R wave from the one track in order to trigger the signal of the other track. Generally, a time separation between the trigger signal and the signal to be displayed, representing in advance, has been found to be about 200 milliseconds for satisfactory results. Based on this system the ECG signals can be superimposed one on top of the other to provide visual comparison between the wave shapes of successive signals.

It is also known to analyze successive ECG signals to determine the R to R interval between successive pulses and to present the succession of R to R intervals as a bar graph which has come to be known as an ARRHYTHMIAGRAPH in general, the bar graph will visually indicate changes in the R to R spacing which changes are directly correlateable to PVC occurrences and other abnormalities. The use of the ARRHYTHMIAGRAPH and an audio presentation of the ARRHYTHMIAGRAPH simultaneously with viewing of the superimposed ECG signals has been found to be particularly effective way in which the SCAN recordings of ECG activity in a rapid manner. This type of scanning has become known as AVSEP. One known scanning system has combined two channels of ECG or AVSEP signal with an arrhythmiagraph in a single tube. However, even though delay lines or shift registers have been used to supply the triggering pulses, there nevertheless has been required the use of two playback heads per channel and the employment of a three gun CRT tube in order to obtain the simultaneous presentation of both channels of ECG and ARRHYTHMIAGRAPH.

Further changes have been made in which a single channel of ECG has been used to obtain a single channel AVSEP by employing a one-shot multi-vibrator as a triggering circuit and displaying the video signal after passing the same through a delay circuit such as an analog or digital shift register. Even so, such a system has required the presentation of simultaneous ARRHYTHMIAGRAPH on a separate tube which is visually difficult for the operator. Reference is also made to U.S. Pat. No. 4,073,011 to Isaac R. Cherry and Donald L. Anderson entitled Electrocardiographic Computer.

The general scheme of analysis set forth in all these references calls for the playback to include two portions. The first portion is an AVSEP and ARRHYTHMIAGRAPH display which is presented to the operator or physician. The purpose of such presentation is to identify those occurences in ECG signal which it is desired to investigate more fully as an assist in obtaining such an analysis, computers have been devised to characterize the wave shape of such successive signals and to automatically stop the AVSEP/ARRHYTHMIA-GRAPH display for time stationary analysis. Among the disadvantages of the prior art systems include the need for multiple head playback arrangements, the use of analog and digital delay lines for processing of ECG signals, the requirement of multi-gun CRT display scopes, the inability to present within a single visual field all of the information required by the operator and an inability to relate time stationary ECG displays to each other and to the AVSEP/ARRHYTHMIA-GRAPH SCAN.

SUMMARY OF THE INVENTION AND OBJECTS

It is the general object of the present invention to provide a method and apparatus for overcoming the disadvantages of the prior art and for providing an electrocardiographic computer display system which provides an improved single field visual presentation of AVSEP/arrhythmiagraph scan mode followed by operator or computer initiated time stationery displays of entire time segments of ECG data. It is a further object of the invention to provide an electrocardiographic display system of the above character in which the visual presentation of the AVSEP/arrhythmiagraph displays are related to each other in a visual sense.

The further object of the invention is to provide an electrocardiographic display system of the above character which employs a single gun CRT tube having a visual field easily comprehended by the operator.

The further object of the invention is to provide a display system of the above character which employs a single high speed playback head system for both AVSEP presentation and for time stationary presentation.

The further object of the invention is to provide a display system of the above character in which the time stationary display is provided with a SLIDE feature, by which the segment selected for print-out can be visually moved within the field displayed.

These and further objects and features of the invention will become apparent from the following summary and detailed descriptions:

The present invention is predicted on the realization that an elegant and direct solution to the problems presented in the prior art can be obtained by employing several computer memories to store various data from the playback of ECG recordings.

More specifically, computer memories are provided for storing the each channel of ECG signal for developing and storing the ARRHYTHMIAGRAPH signal and for developing R wave pulse data signal. By employing suitable clocks and counters, these memories can be continuously up-dated on a first in, first out, basis and operated in a circular manner to retrieve stored segments of data for repetitive visual presentation at a repetition rate sufficient to render stabilized images. For convenience, large memories are provided for storing ECG signals over longer time periods for stationery time presentation. The latter memories are employed after a stop SCAN signal has been generated either by the operator or by an arrhythmia detection computer.

In connection with the foregoing, cross-reference is made to U.S. patent application entitled "METHOD AND APPARATUS FOR ARRHYTHMIA ANALYSIS OF ECG RECORDINGS" by Donald L. Anderson et al and filed concurrently herewith and assigned to the same assignee as the present invention, wherein a complete computerized system for automatic arrhythmia analysis is set forth. That application details the specific computer circuitry required for rapid arrhythmia analysis and is illustrative of the manner in which a stop scan signal can be generated during high speed AVSEP scanning of ECG recordings.

More specifically, the present invention employs a method for displaying a sequence of ECG signals taken from a data recording thereof in which the operator or a computer switches the display from a time moving SCAN mode to a time stationary mode of viewing segments of ECG data. The invention calls for converting the ECG signal into a digital form and storing the same in digital memories. The signal is also applied to an R wave detector, the output of which is also converted to digital form and stored. In SCAN mode the contents of the respective memories are displayed one memory being accessed through a counter having a preload which enables a 200 millisecond delay to be established between the R wave data and the ECG signals. In this way the signals are presented seriatum and superimposed upon each other to form the visual AVSEP display. The signal is also used to generate a signal of R to R intervals which are stored in an arrhythmiagraph memory. These signals are played back as a bar graph or peak mode's signal against an arbitrary time base. If the foregoing signals are represented at a repetition rate sufficiently fast, they will appear to an observer as a visually constant signals. A repetition rate of about 60 cycles per second has been found satisfactory.

Whether generated by the operator as a stop command or by an ARRHYTHMIAGRAPH computer, the aforementioned display can be stopped in progress. ECG signal memories of substantial capacity are employed to store the ECG signal and to continuously up-date the same as the tape or recording mechanism is scannedAt least two modes of time stationary display are presented and are inter-related between each other and to the portion of the signal which was scanned immediately preceding the stop command. The first of these modes provides for a SLIDE presentation, in which one or more channels of ECG is presented for a pre-determined interval of the visual field of the scope by addressing the respective ECG memory for the time interval desired. This selected ECG field can be moved by changing the addressing in increments either (left) (up) or (right) (down). The same selected field address change is used to generate a signal the duration of which represents a cursor or window indicating the relation between the ECG display and that portion of the ARRHYTHMIAGRAPH signal which is simultaneously presented, so as to highlight that portion of the ARRHYTHMIAGRAPH display that corresponds to the viewable ECG display. Most conveniently, the cursor or window can be obtained by Z axis intensification by the portion of the arrhythmiagraph which corresponds to the ECG signal.

In a second (PAGE, JOG) display a larger segment of ONE CHANNEL of ECG signal is presented in which the signal used for selected SLIDE segment, is used to produce an intensification or cursor window directly on the ECG trace. In this display the ARRHYTHMIAGRAPH is omitted.

A provision is made for the cursor or window area within display to be printed as in a written electrocardiograph trace.

BRIEF DESCRIPTION OF THE DRAWINGS

FIGS. 3, and 3A-3F are detailed circuit schematics of the disgram of FIG. 2.

FIG. 4 is a block diagram of the ARRHYTHMIA-GRAPH module of the system of FIG. 1.

FIGS. 6 and 7 are detailed block diagrams of the ECG CPU system of FIG. 1.

FIG. 9 is a block diagram of the timing and display circuits of FIG. 1.

FIGS. 10, and 10A-10J are detailed circuit diagrams of FIG. 9.

FIG. 16 is a continuation of the interrupt flow diagram of FIG. 13 in relation to a JOG jog display control.

A detailed program listing for carrying out the steps of the flow diagram of FIGS. 11-16 is given in Appendix A.

FIGS. 17a, B are graphs of the X and Y output signals representative of AVSEP and ARRHYTHMIA-GRAPH SCAN.

FIGS. 18 A B is a CRT Trace of the display scope taken during a representative SCAN with FIG. 18c in the signals of FIGS. 17, together with the ARRHYTHMIAGRAPH display bar mode.

FIG. 19 is a peek mode ARRHYTHMIAGRAPH display.

FIGS. 20A-D are X, Y, and Z output signals representative of digitals of a SLIDE mode SCAN.

FIGS. 21A-C is a CRT trace of the display scope taken during a representative SCAN With the signals of FIGS. 20.

FIGS. 22A-D are X, Y, Z output signals representative of a PAGE mode SCAN.

Figure 23:
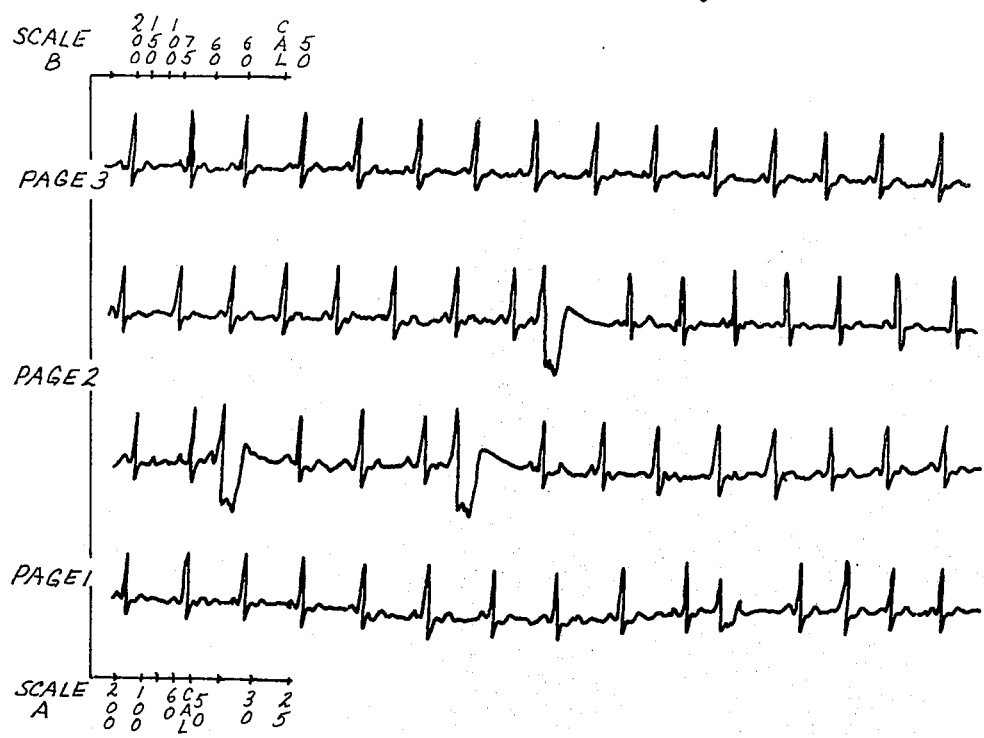

FIG. 23 is a CRT trace of the display scope taken during a representative SCAN with the signals of FIGS. 22.

Figure 24:
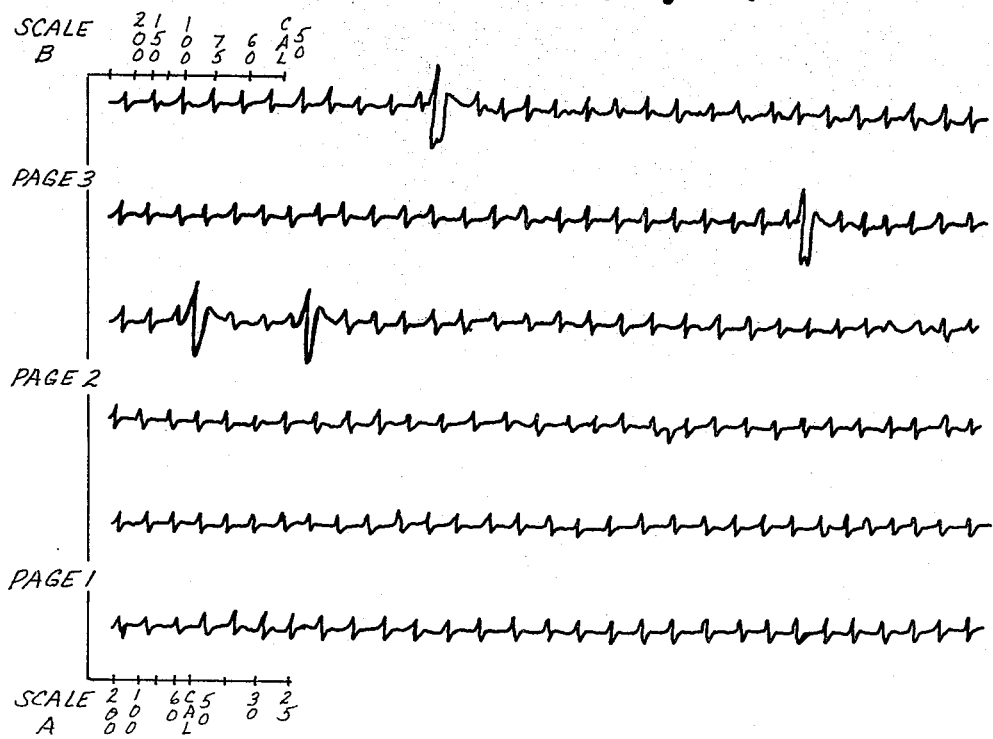

FIG. 24 is a CRT trace of a JOG mode SCAN showing complete 3 minute ECG memory display and cursor intensification, the waive forms for which are substantially similar to those of FIG. 22.

DETAILED DESCRIPTION OF THE PREFERRED EMBODIMENT

System Overview

The multiscan display system of the present invention provides for ECG waveform data to be shown in one of four possible display modes, falling into a SCAN mode and a stationary mode. The scan mode consists of an AVSEP display including a repetitive and scanning sequence of ECG superimposed signals together with an ARRHYTHMIAGRAPH display both of which are continuously updated. Upon stop command being given the display is switched to a SLIDE mode which is a time stationary mode in which both channels of ECG are displayed. Display movement within the stored time frames together with simultaneous correlation with the ARRHYTHMIAGRAPH display is provided in which a window of the ARRHYTHMIAGRAPH is defined as that segment corresponding to the ECG presentation, and also corresponding to the last segment of SCAN AVSEP display before the stop command was generated. PAGE & JOG display modes are provided which encompass larger time segments with an enhanced portion designating the cursor or window section previously designated in the ARRHYTHMIA-GRAPH display.

The SCAN display mode is more precisely a high speed superimposed two channel ECG AVSEP display with a continuously updated three minute ARRHYTHMIAGRAPH of R to R intervals displayed on the same field of view and the same CRT scope using time shared circuitry. The ECG display trace may either show a single beat superimposed or a double beat superimposed AVSEP ECG signal, as desired.

The SLIDE display mode shows a time stationary three minute ARRHYTHMIAGRAPH or R to R intervals and 11 seconds of real time ECG data from each ECG channel. An intensified section or cursor on the ARRHYTHMIAGRAPH references the displayed 11 second section of ECG wave form data. Keyboard control allows the operator to SLIDE the cursor along the entire three minute ARRHYTHMIAGRAPH and to bring into view the real time ECG daga for any 11 second segment within the ARRHYTHMIAGRAPH, the ECG presentation moving across the screen display as the cursor window is moved.

A PAGE display mode presents one minute of continuous ECG data from either channel. The three minutes of wave form ECG data held in the respective ECG memories when the tape is stopped are displayed as four, 15 second traces with respect to each of the three pages of 3 minute memory. A Z axis intensified segment of this display relates the position of the cursor to the 3 minute ARRHYTHMIAGRAPH cursor previously displayed in the SLIDE more.

A JOG display mode shows 3 minutes of continuous ECG data from either channel and displayed from memory as 6, 30 second traces. Again, intensified portions of the display traces refer to the cursor window position of the 3 minute ARRHYTHMIAGRAPH of the SLIDE display mode. The PAGE and JOG mode displays are not accompanied by ARRHYTHMIA-GRAPH displays, the latter being shown only in the SLIDE mode presentation.

In operation, the display is initially in SCAN mode and upon receipt of the stop command, automatically shifts to one of the SLIDE, PAGE, & JOG displays, preferably the SLIDE display, from which the operator may elect to use either of the other time stationary displays as desired. A computer system is employed to generate the calculations necessary to address all counters and memories and to enable the various circuits required to generate the timing and switching of the displays.

Figure 1:
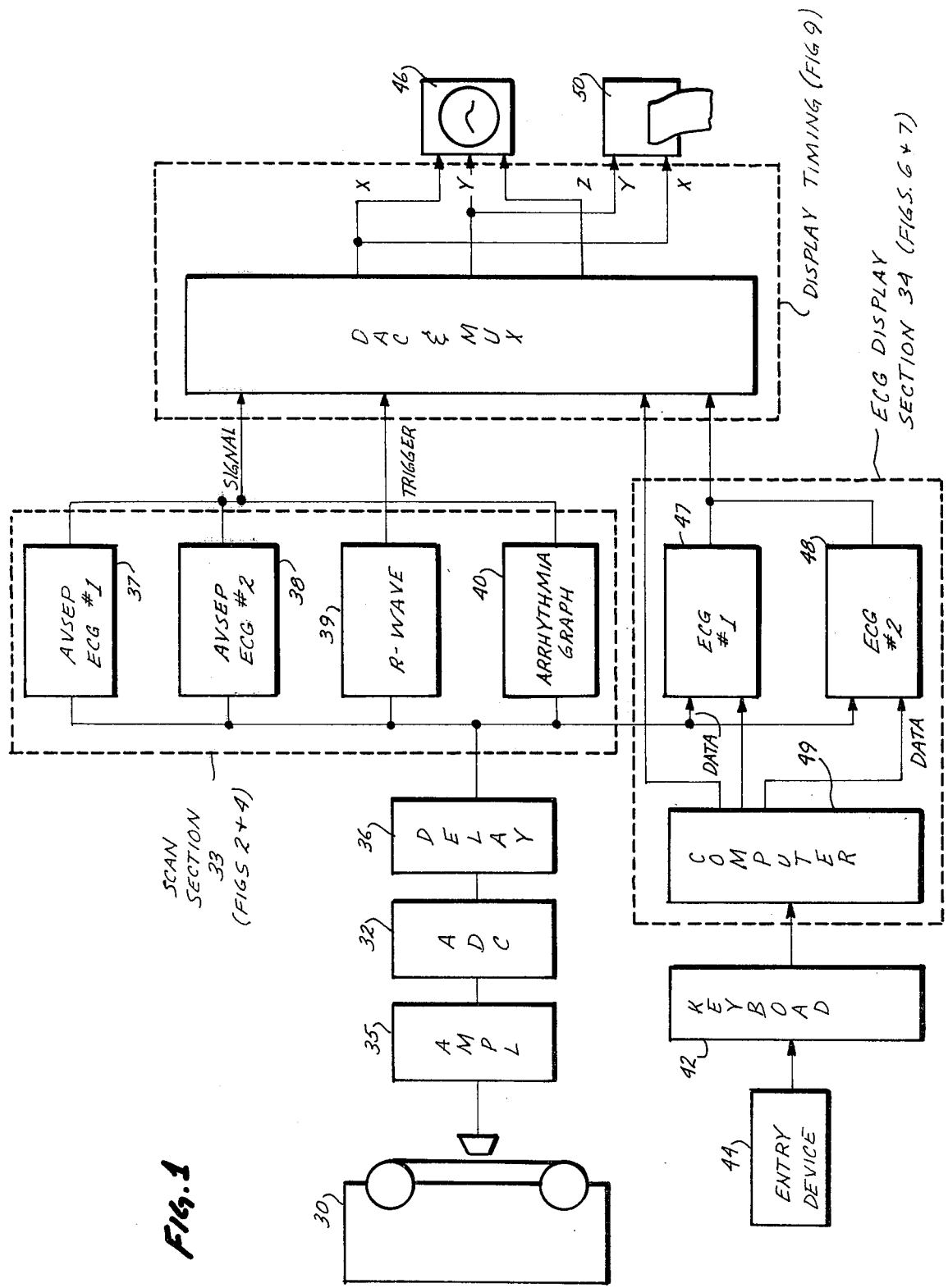
FIG. 1 is a general block diagram of electrocardiographic computer display system constructed in accordance with the present invention.

FIG. 1 shows a block diagram of the overall electrocardiograph display system of the present invention which includes a tape transport 30 for rapid scanning of ECG recordings, the output of which is applied through an analog to digital converter 32 to a SCAN or AVSEP/ARRHYTHMIAGRAPH section 33 and to an ECG time stationary display section 34 through an amplifier 35, and a two second delay circuit 36. SCAN section or module 33 includes AVSEP ECG memory 37 for channel 1, AVSEP ECG memory 38 for channel 2, R wave detector and memory 39, and R-R detector and memory 40. Operation of the system is controlled by an operator keyboard 42 which also employs a separate hand-holdable entry device 44 for rapid entry of operator generated SCAN and stop commands and other instructions. The output of the AVSEP/ARRHYTHMIAGRAPH section 34 consists of XY signals which are reassembled into analog form by a suitable DAC, multiplex and deflection circuits 45 for display on CRT 46. During SCAN mode AVSEP/ARRHYTHMIAGRAPH signals are applied to DAC/MUX 45; while upon issuance of a stop command, a second display mode of time stationary ECG signals is supplied from the ECG module 35 to the timing and display module 45 including signal DAC & MUX circuits 46. Module 34 includes extended channel 1 and channel 2 ECG memories 47, 48 controlled by micro computer 49. A moveable, selected segment of the ECG signal is located during the later presentation, and then printed out on a suitable XY platter 50 upon operator command.

Figure 2:
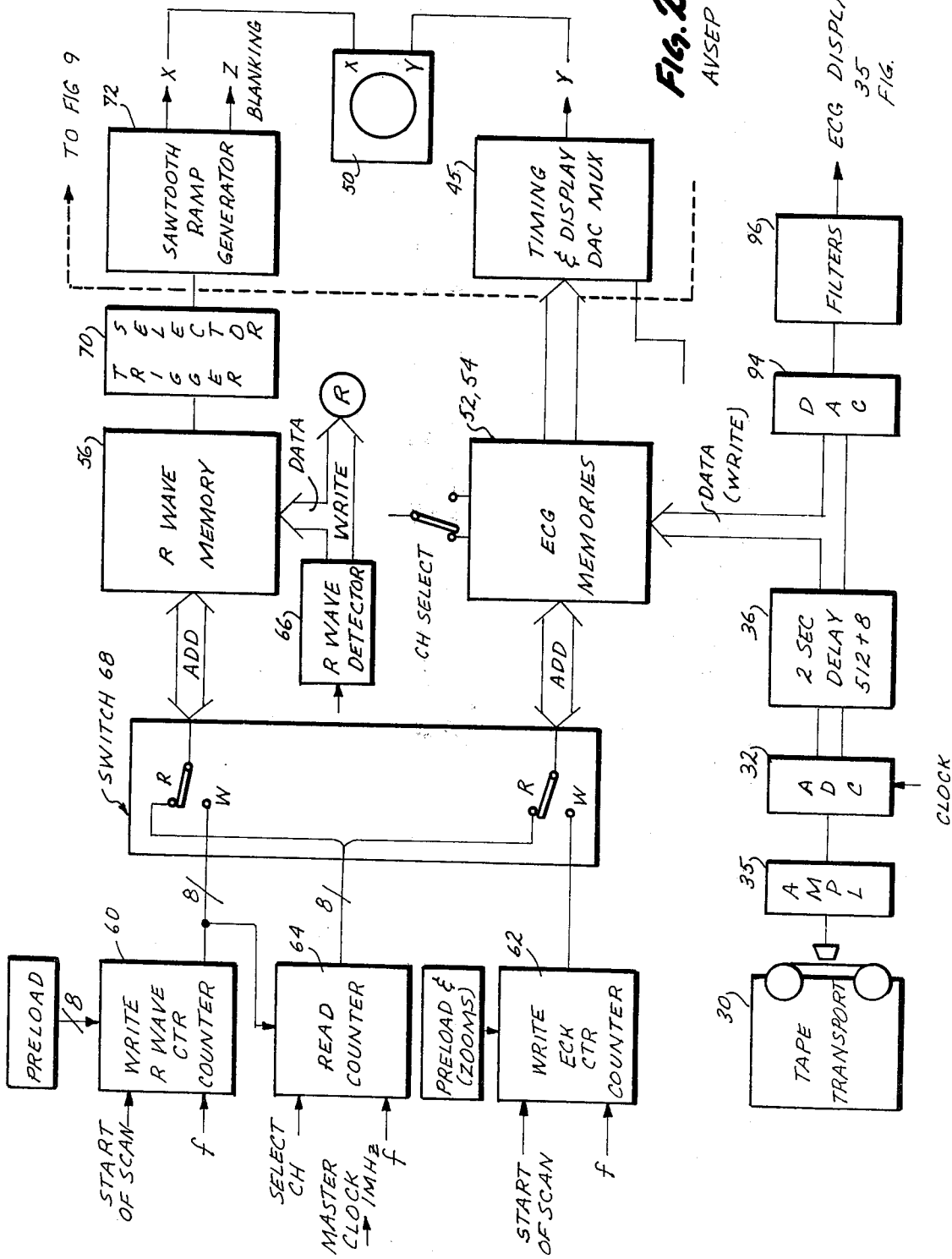
FIG. 2 is a block diagram of the AVSEP module of the apparatus of FIG. 1.

A more detailed block diagram of the SCAN section 34 is given in FIGS. 2 and 4. The basic principle in this mode of display is that all ECG and R wave data are digitized and stored in separate memories. Each memory is then read in sequence. The R wave memory 40 serving as trigger signal source for ECG AVSEP with which it is read synchronously. Wherein the memories 37, 28 comprise AVSEP ECG data channels 1 and 2 ARRHYTHMIAGRAPH R-R interval memory 40 is used in conjunction with a suitable sawtooth generator. To provide the superimposed AVSEP effect.

AVSEP Module

Figure 3:
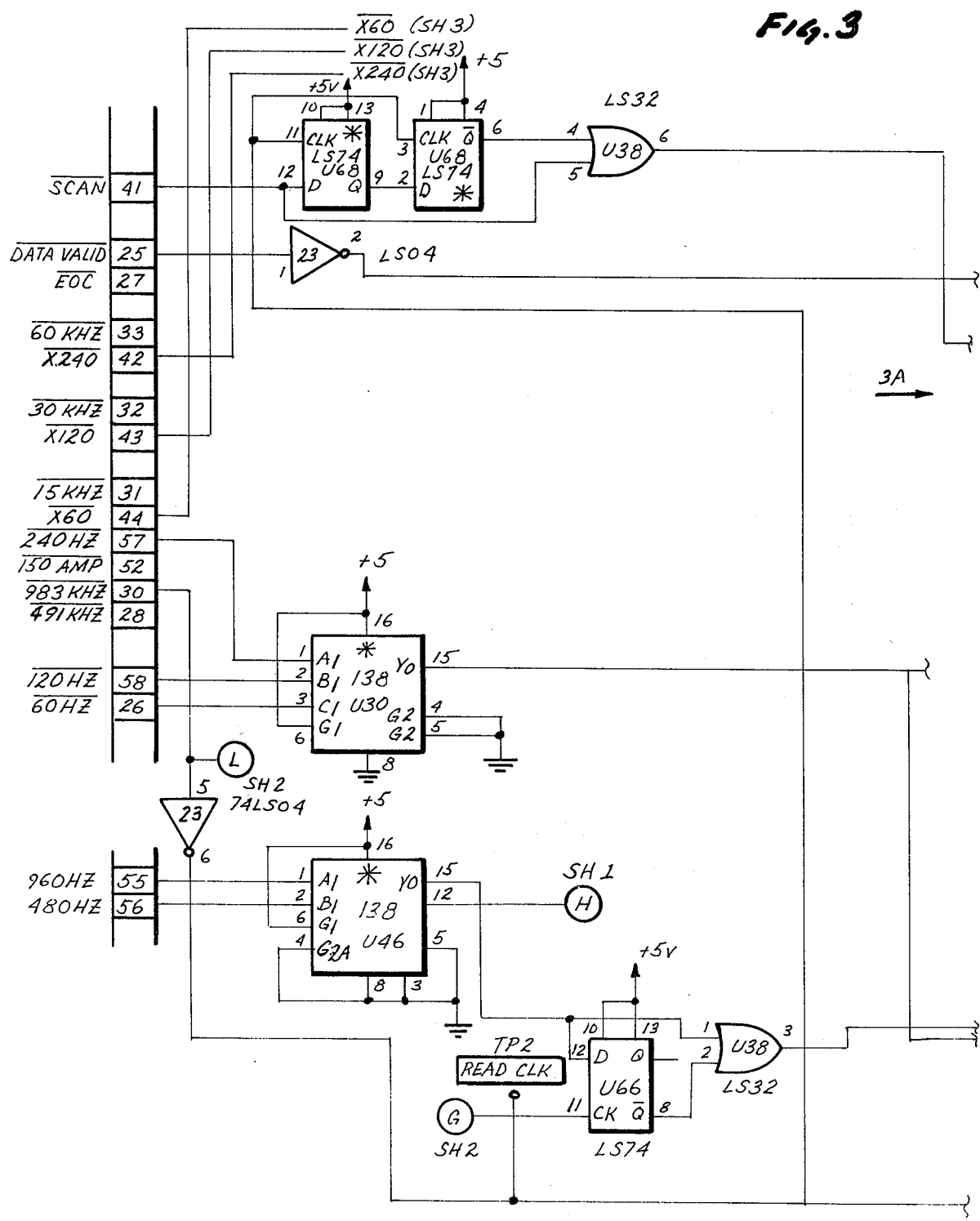
Figure 3A:
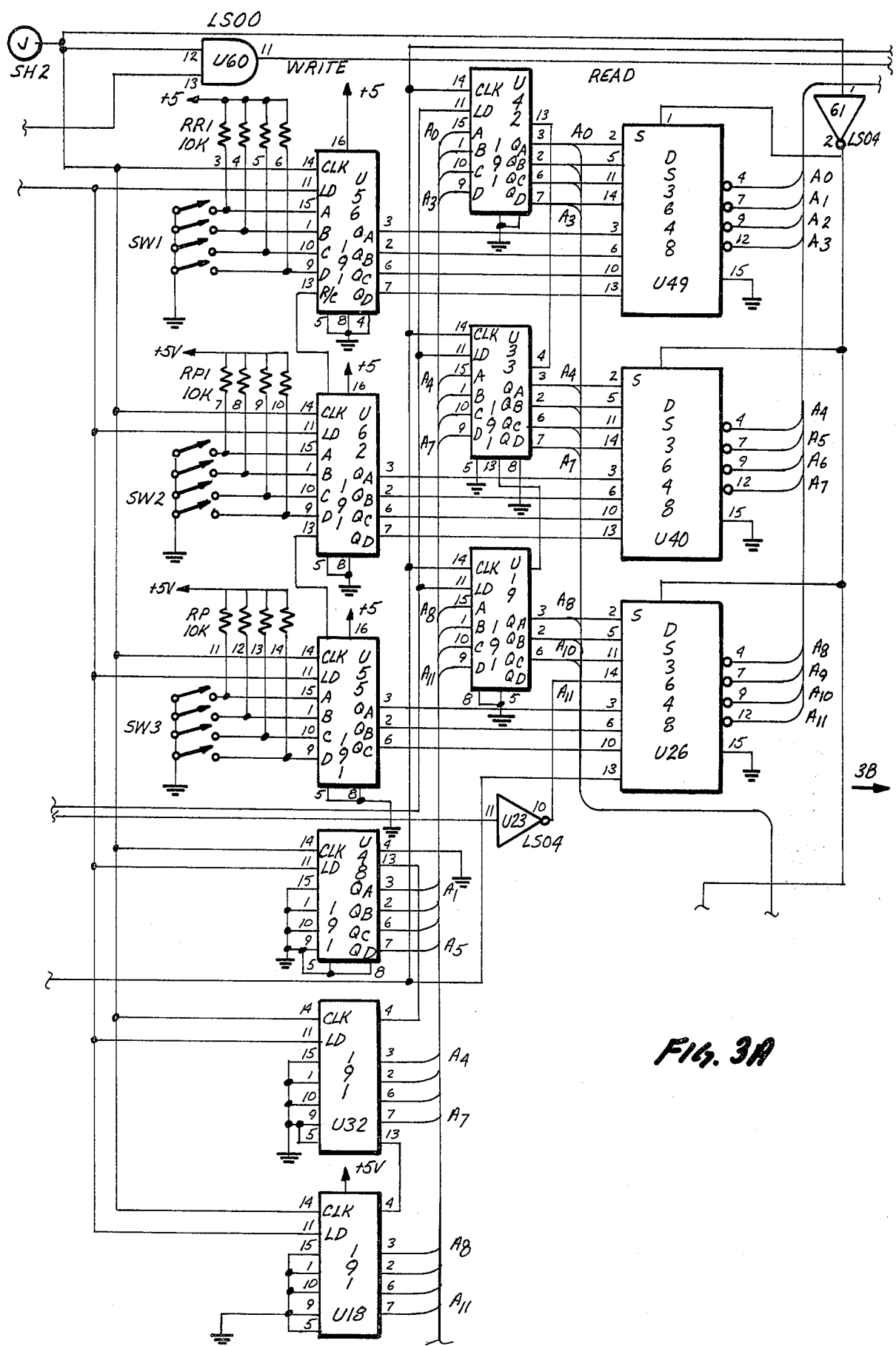
Figure 3B:
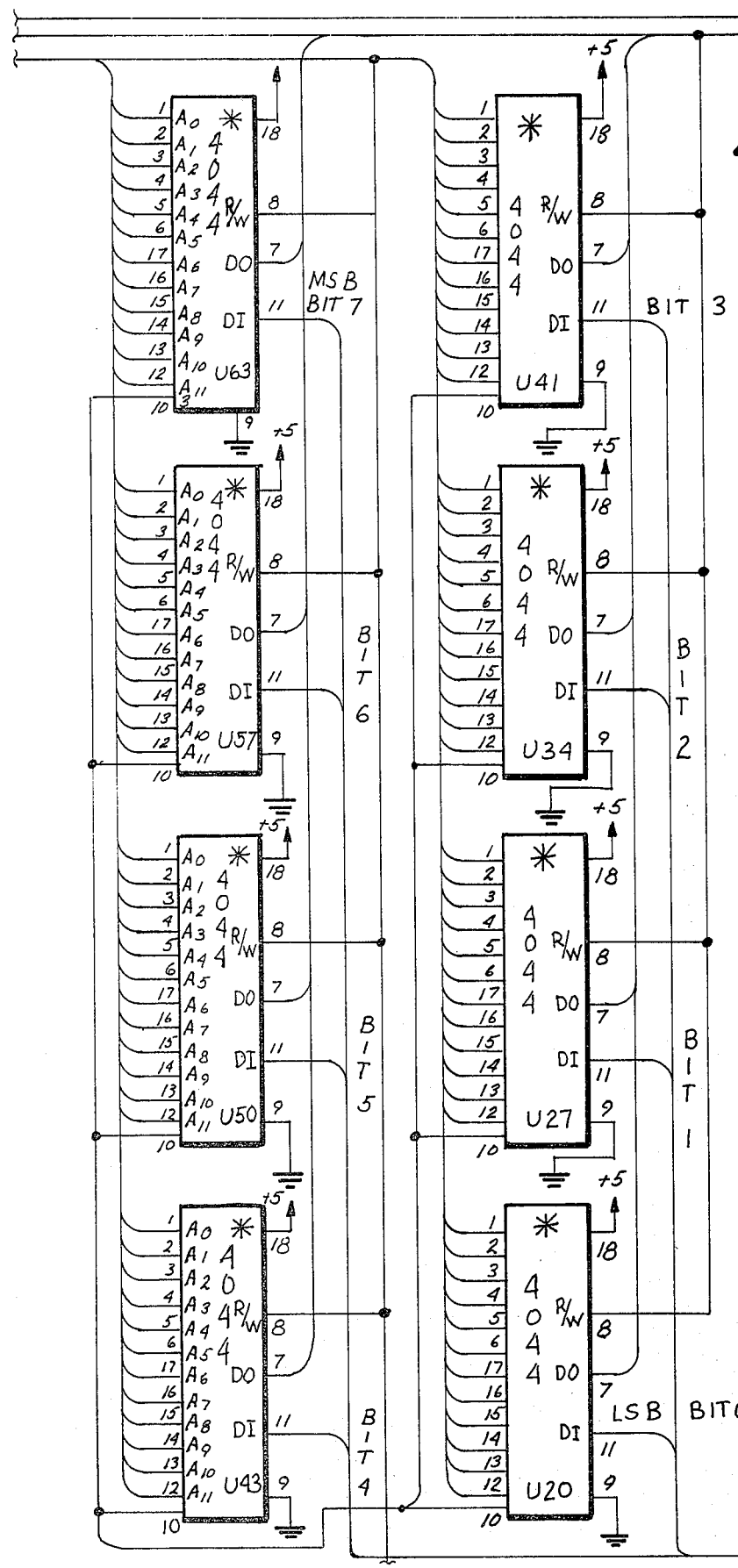
Figure 3C:
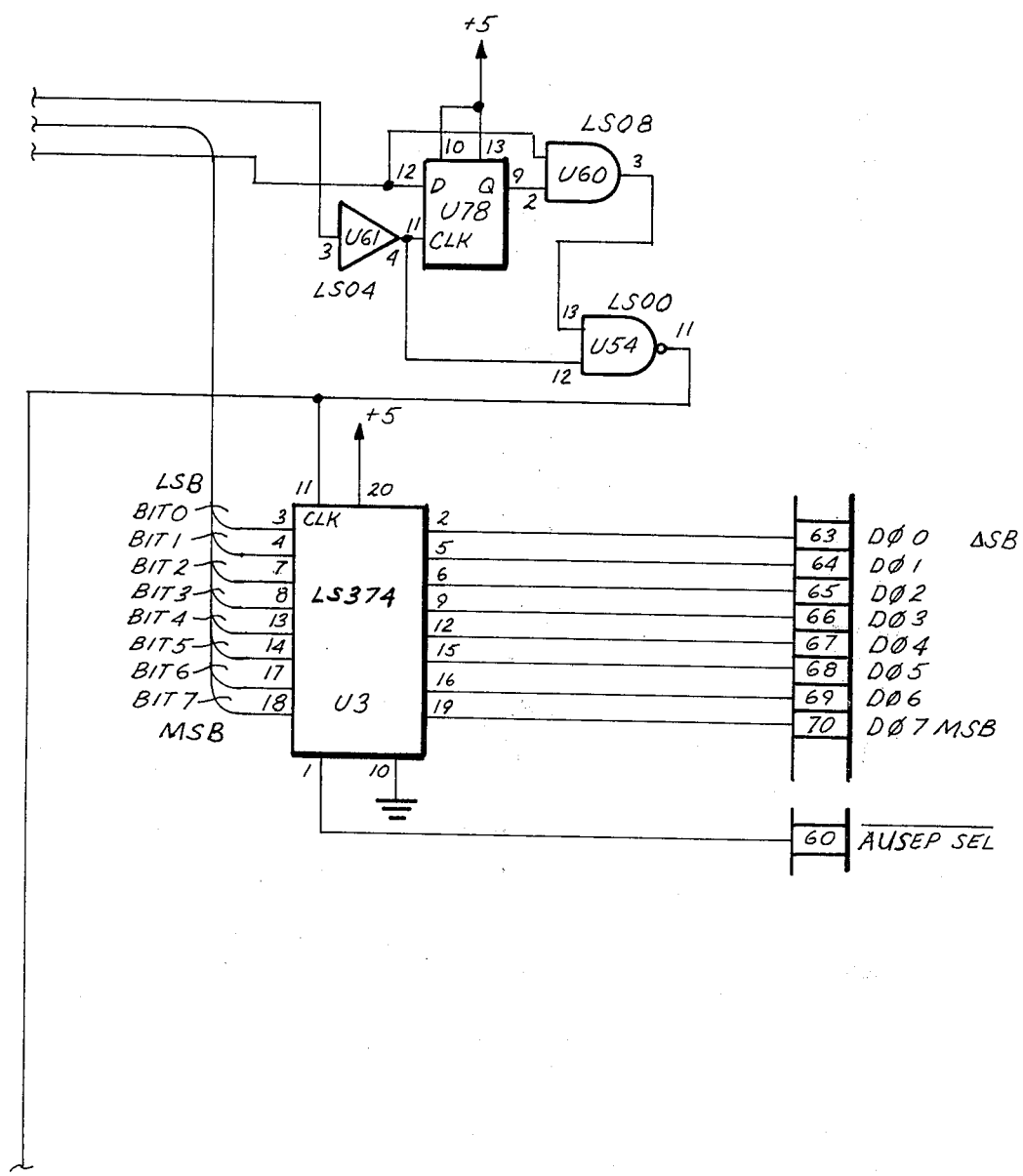
Figure 3E:
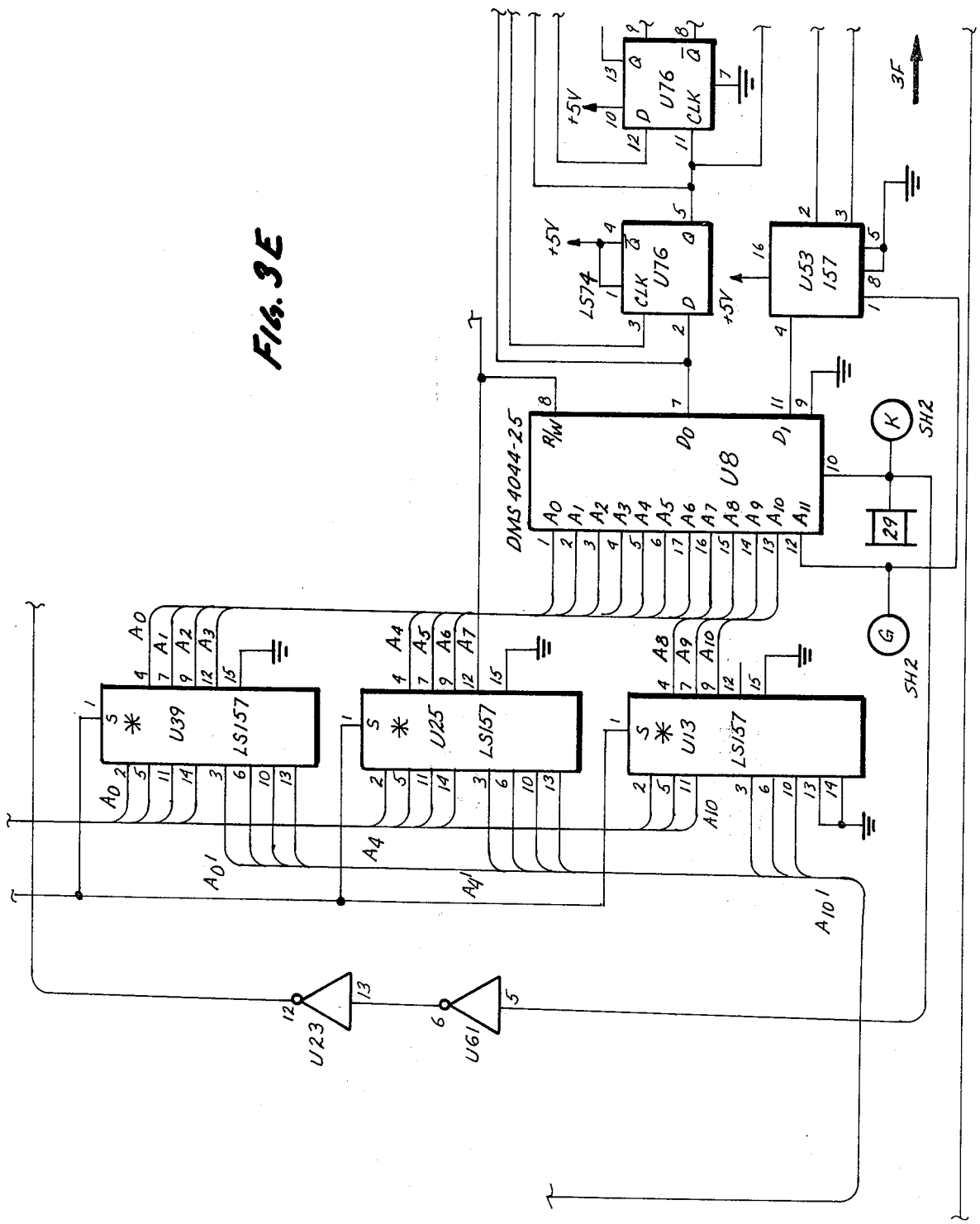
Figure 3F:
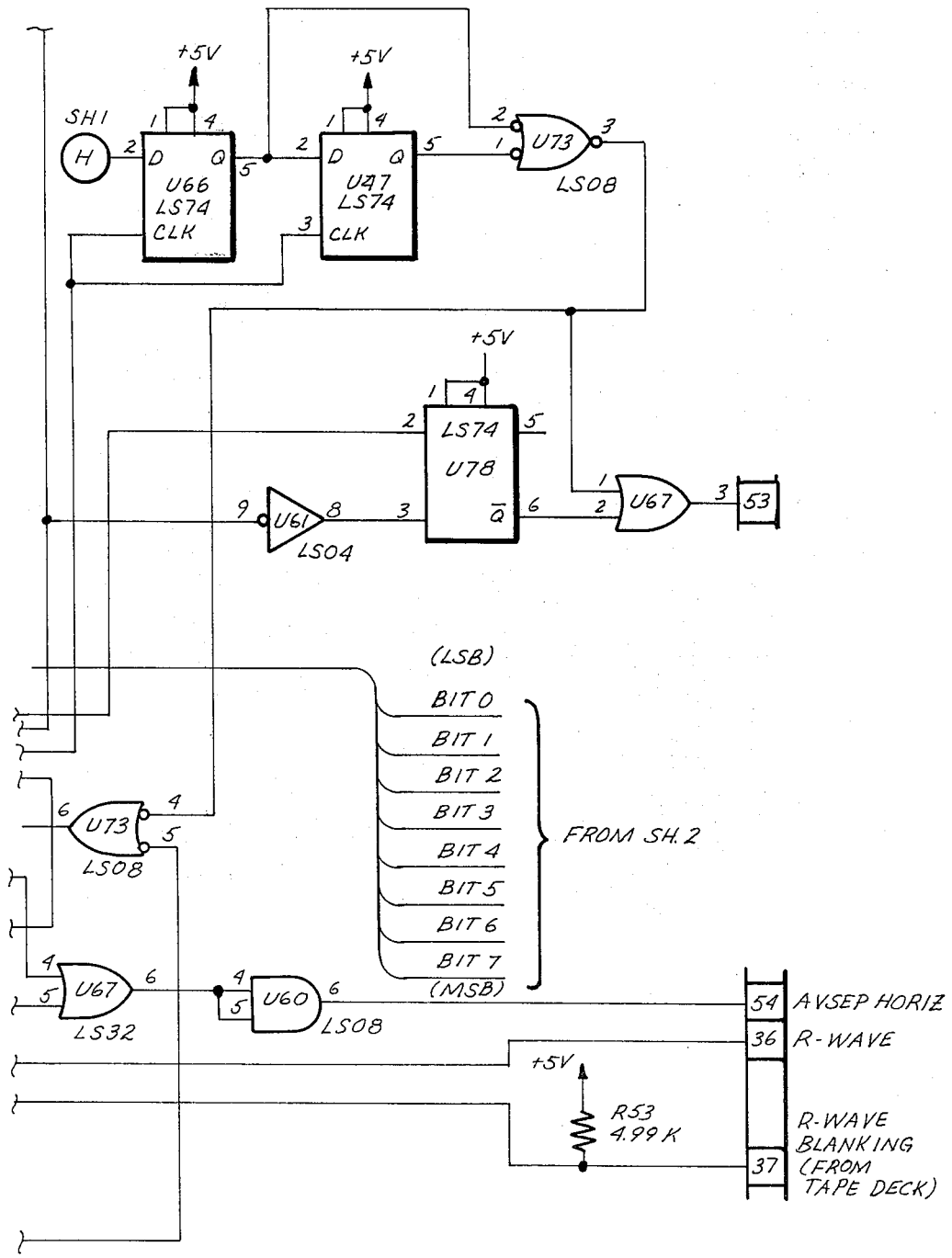
Figure 5A:
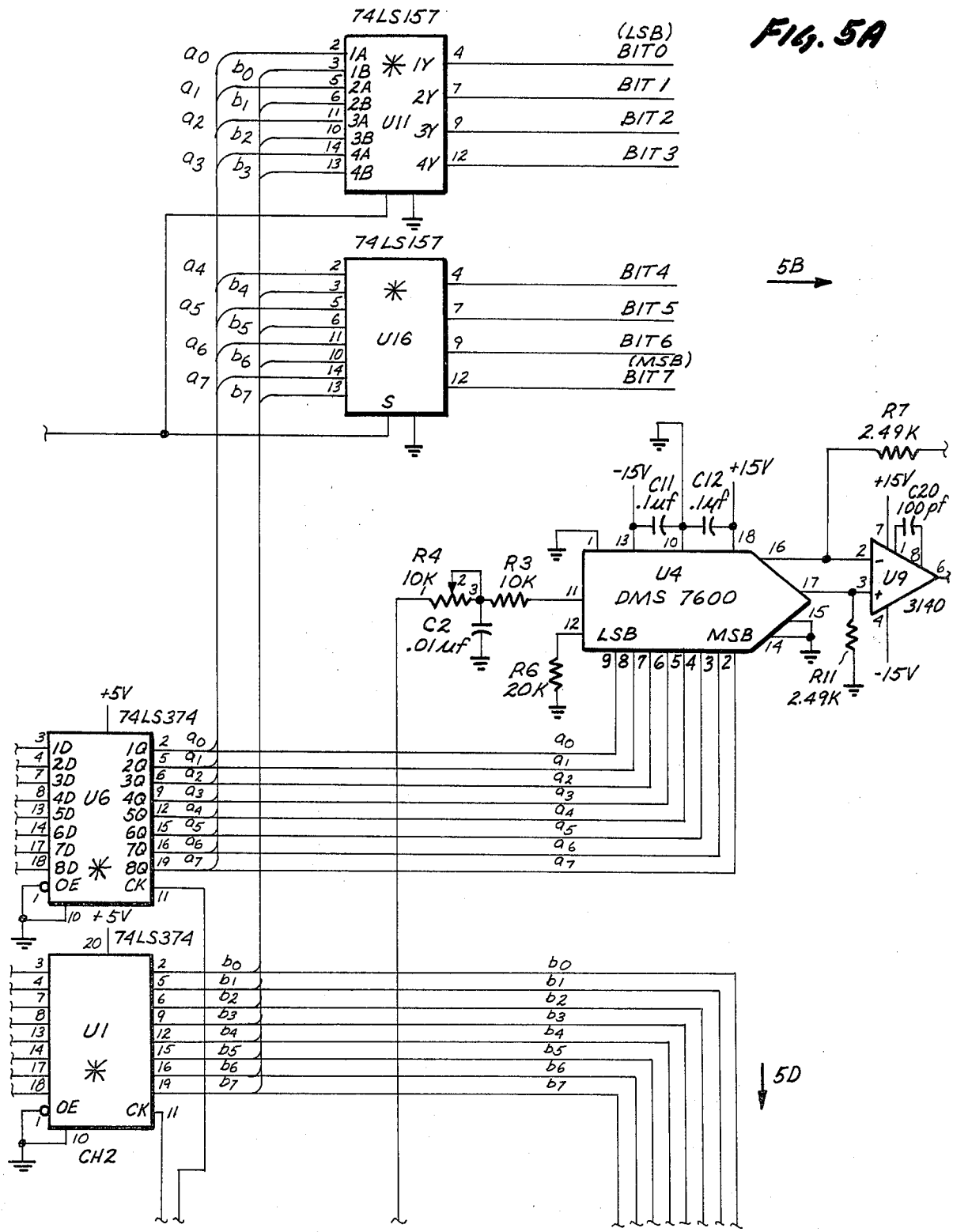
FIGS. 5, and 5A-5P are detailed circuit diagrams of the circuit of FIG. 4.
Figure 5B:
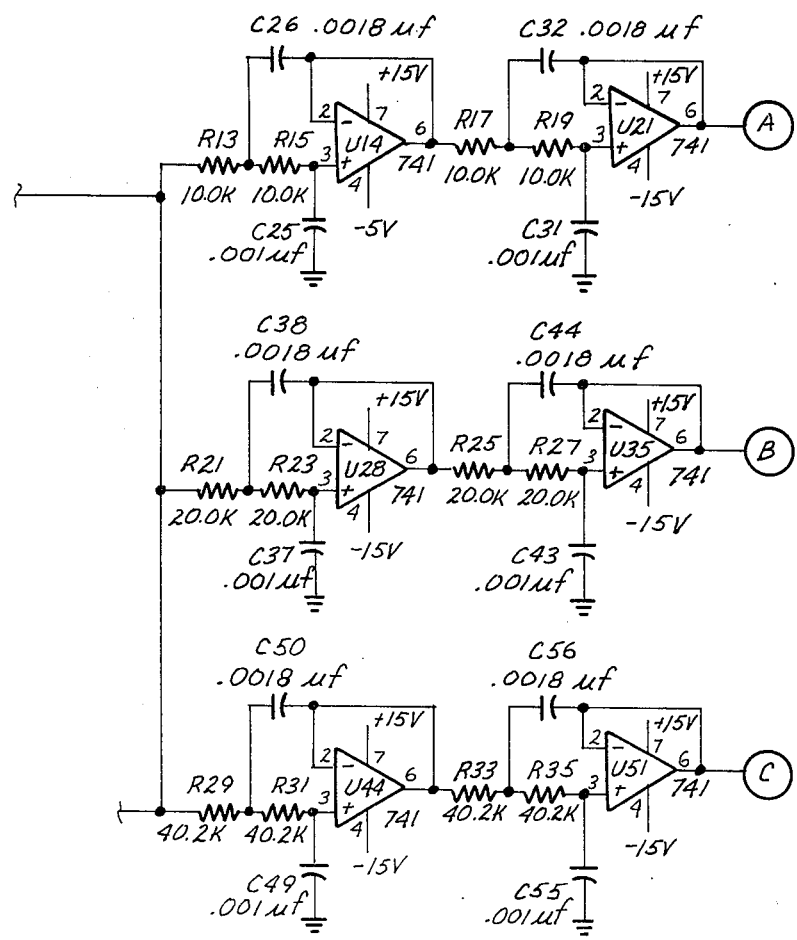
Figure 5D:
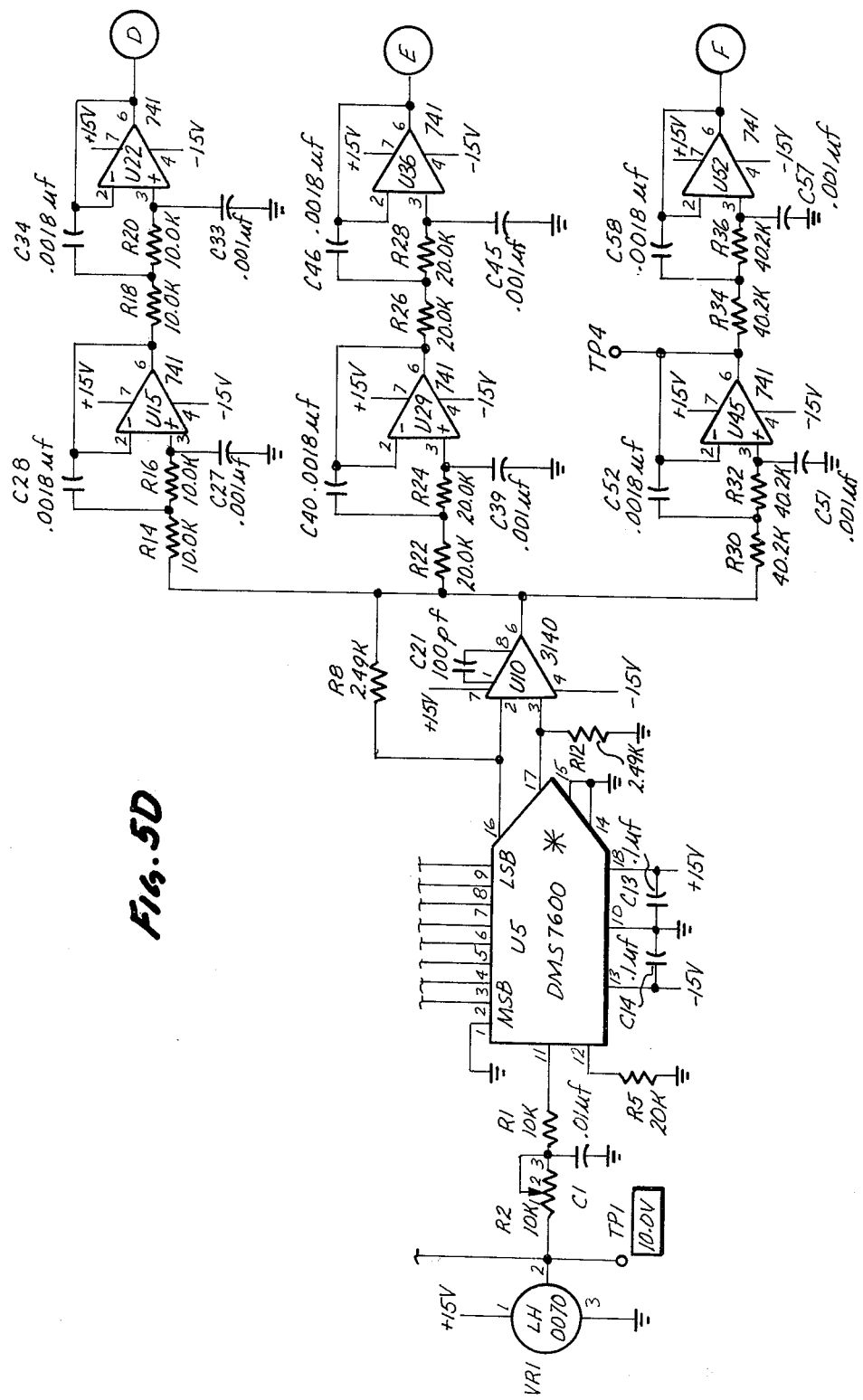
Figure 5I:
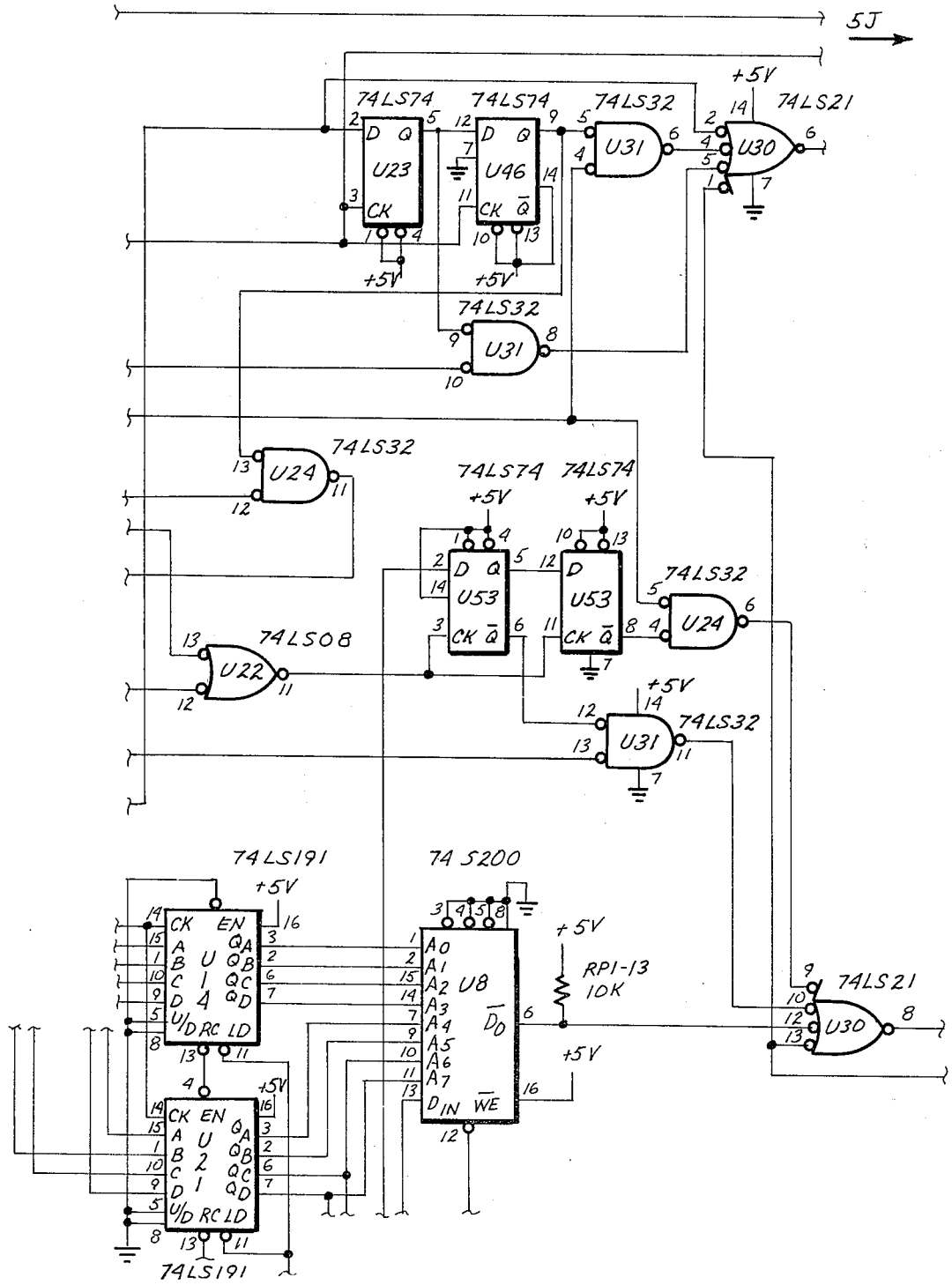
Figure 5K:
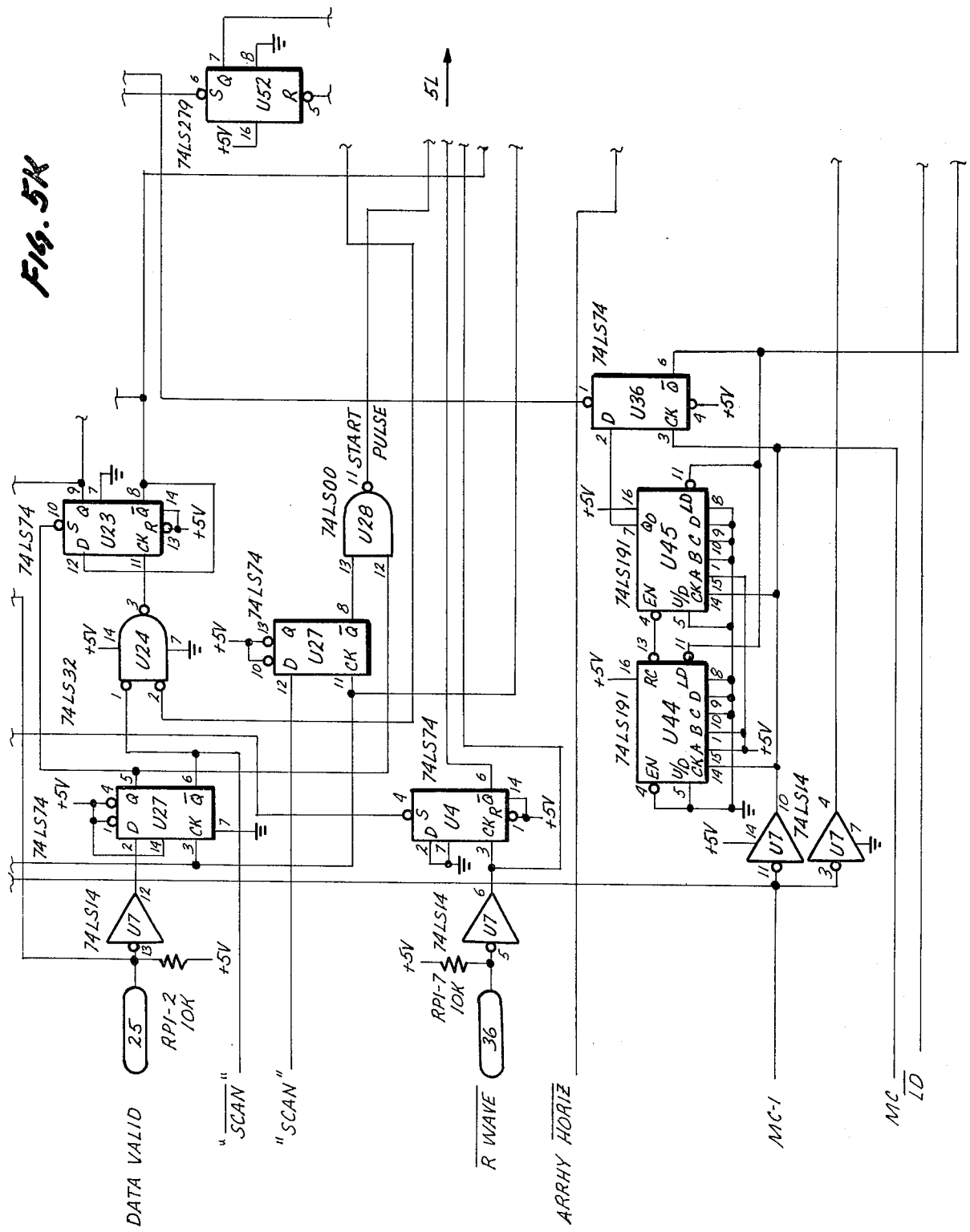
Figure 5M:
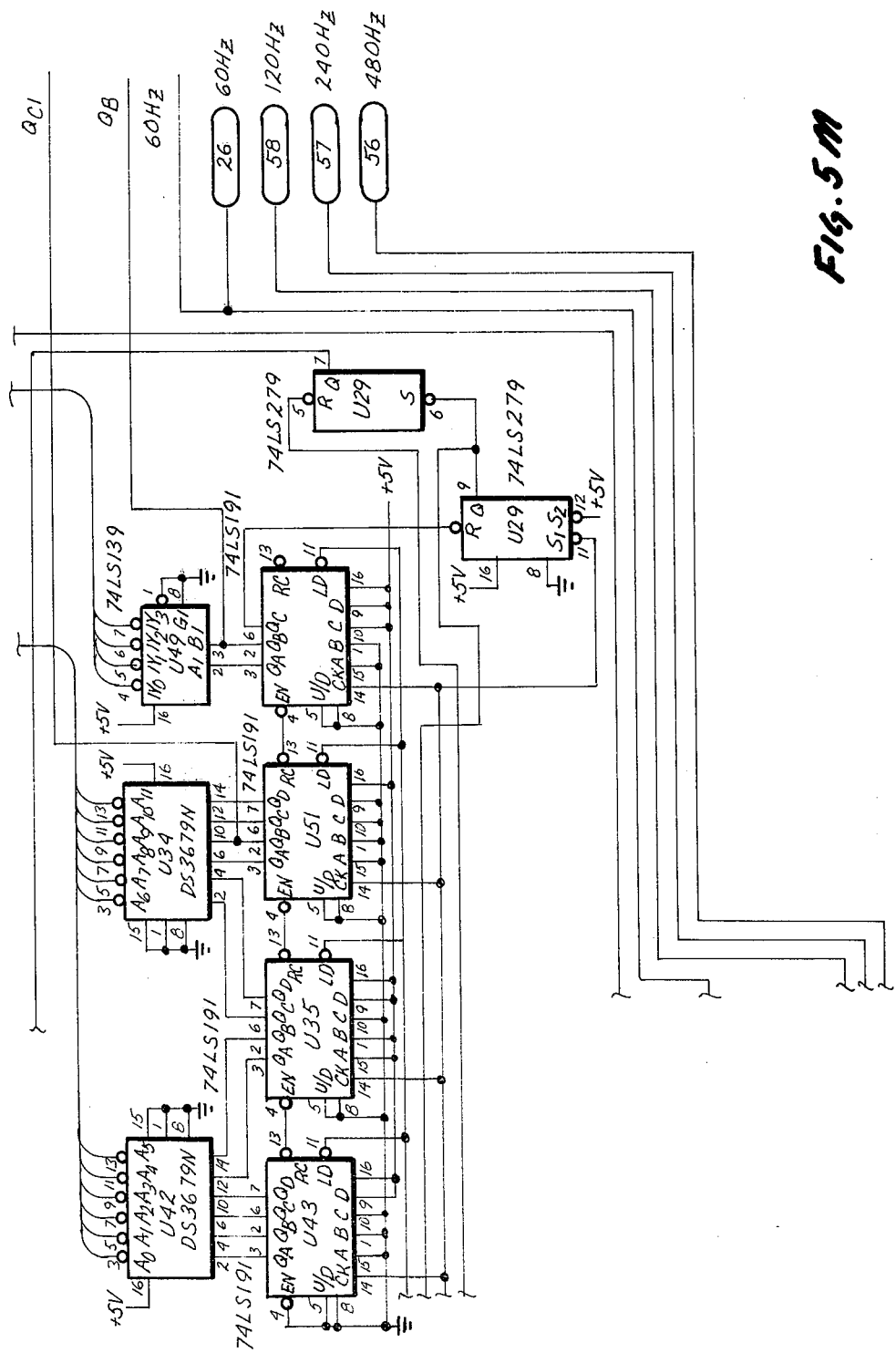

Referring now to FIGS. 2 and 3, the AVSEP module of the present invention is disclosed and consists generally of ECG memories and R wave memory controlled by suitable with clocks 60, 62 and read clock 64. In this mode the tape transport is operating in scan and the tape ECG output is taken through suitable amplifiers 35 and an ADC converter through 2 second delay memory 36 before being applied as data to the R-wave and ECG memories circuits. The delay memory is used in order to assist in distinguishing between non-ECG data contained on the tape, as for example, patient event markers and the like, which it is desired to keep from passing into the ECG circuits of the present invention. The ECG data is passed through an R wave detector 66 and developed in an R wave pulse train which is stored in R wave memory. ECG data is loaded into two circular refreshable memories which can consist of a 4096×8 bits memory divided into two sections, one for each channel. The R-wave memory is 4096×1 in size and divided into two 2048 sections. One section is used for recording the R wave pulse generated and the other section is used for an R wave blanking signal which is also generated at a suitable interval and is used to black out the display. The circuit memories for the R wave and ECG signals are controlled by write counter clocks, the preload to which is off-set by a count corresponding to 200 milliseconds. The read counter clock 64 is provided for reading the circular memories at predetermined intervals. The outputs of the counters are passed through a suitable electronic switch 68 which is cycled between the read and write functions as will be described. Referring to FIG. 4, a detailed circuit diagram of the AVSEP module is disclosed in whigh the various blocks of the diagram of FIG. 3 are indicated. The frequency of operation of the write clock may be the basic sampling rate, i.e., the same frequency as used in digitizing the analog ECG signal. Thus for every digitized sample, there is a stored signal for each of the ECG and R wave memories at a rate of 256 samples per second at patient time. However, when playing back at higher speeds, as x120 or x240, it will be appropriately faster. The read counter is running at a fixed rate which is 1 megahertz and the resulting signal is within a 60 hertz time frame, or refresh period. The switch circuit is synchronized with the clocks so that the read and write functions are derived. Referring to the schematic U49, U40 and U26, forms a set for ECG memory and an additional set U39, U25 and U13 are employed for the R wave memory. This switching function is electronic which has two inputs selected by a control line so as to switch two sets of line. Each set has 12 address lines for each of the write and read functions. The switch is normally set at the read position and then when a write command comes, it switches back to the read again. During each cycle there is a certain amount of data which is stored in the memory so that there are about 8 cycles (approximately) during each read cycle that one has to update the memory.

As shown, there are two preload circuits, one for each of the ECG write counters. The difference is that the write counter for the R wave is set at zero and so consequently there is no switch required. The preload for the right counter is set at a value determined by the difference from the zero address to an address suitable for establishing a 200 millisecond delay, so that the ECG display is approximately 200 milliseconds ahead of the R wave sawtooth. By this means, the R wave of the ECG complex is included in the ECG AVSEP display. Thus, each of the memories operates in a circular fashion being loaded by the write address counters and unloaded periodically by the read counter. The output of the R wave memory is taken through a trigger selector circuit 70 to a sawtooth generator 72 while the ECG data output is taken through a DAC timing and control circuits 45 display scope 50.

For two-channel AVSEP system shown, a 60 Hertz refresh rate is used for the display with the display time allocation as collows, ARRHYTHMIAGRAPH 8.33 milliseconds, channel 1 ECG 2.08 milliseconds, channel 2 ECG 2.08 milliseconds, a minimum of 4 seconds real time storage is required for each channel, so that no ECG wave form is missed even at a x240 tape speed of SCAN. An 8 second memory has been found satisfactory so as to provide sufficient overlap.

ARRHYTHMIAGRAPH Module

Referring to FIG. 3 the ARRHYTHMIAGRAPH module block diagram is shown and comprises means 66 for generating an R wave pulse train corresponding to the rising portion of each ECG complex received, the output of which is passed through a buffer memory 80 to 16 k×1 RAM memory 32. A buffer address counter controls 84 the buffer memory for loading and updating of the contents at a periodic rate. A memory address counter 86 is connected to the RAM for loading and unloading the contents in accordance with the read-write cycle established by a logic control circuit 88. Both of the buffer address counter and the memory address counter are cycled at the 2 megahertz sampling rate from counter 90 and used throughout the system. The output of the 16 k×1 RAM 92 is taken through an 8 bit counter 90 and a peak latch 92 before being converted to an analog signal by a DAC 94. The peak latch is selectively operable to sample and hold each last R wave value received so that when connected, the R wave memory is taken as a peak signal graph, and, when otherwise disconnected, the peak latch is reset at the sample rate so that a bar graph signal is generated.

In operation the main memory runs circularly through a complete loop and at that point all of the data collected in the buffer memory is unloaded into the main memory during the write cycle. During the read cycle, the information is stored in the buffer memory and at the end of that loop time, the memories cease reading and are written from buffer to main memory. When scanning has stopped, there is no new data coming in and it is desired to know where the main memory was at the point of interrupt by the stop command. This brings into operation the time base counter 96 which actuate at that point. This counter has the same length as the main memory so consequently it will repeat to the point wherever it stops. That point is detected and used to generate a pulse to carry the necessary time base to the remainder of the display system. The write sampling rate is 16 killohertz while the read sample rate is 1 megahertz.

Two basic types of time stationary displays are provided in this system. The first is termed the SLIDE mode of display and consists of multi-channel ECG display in conjunction with a simultaneously presented arrhythmiagraph. The ECG display is of a relatively short duration encompassing at least the portion of ECG signal which constituted the AVSEP display which immediately preceded it. The arrhythmiagraph display includes an enhanced portion which corresponds to the segment of ECG. The enhancement is preferably by way of Z axis intensification of the trace. More specifically, the SLIDE mode display ECG portion is derived from a selected 11 seconds of the 3-minute ECG memory for each channel, while the arrhythmiagraph portion of the display is taken from the complete arrhythmiagraph 3-minute memory. A keyboard is provided for entering the operator's selection of display mode and other features of the invention. A hand controller is also provided for entry of stop commands and left and right motion of the ECG SLIDE display. Suitable push buttons are provided on both the hand controller and keyboard for this purpose. Pressing the left or right buttons on the hand controller or keyboard causes the computer to add or subtract values from address counters which control which 11 seconds of the 3-minute ECG data is displayed and thereby move the ECG display left or right in a sliding motion together with the intensified portion of the arrhythmiagraph display.

In a second time-stationary display mode a single channel of ECG is displayed over a period much longer than the AVSEP or slide displays. The first of these is termed the PAGE mode and consists of 1 minute of ECG memory in which the portion related to the SLIDE display mode is enhanced, as by Faxis intensification. The last display mode is the JOG mode which is a 3-minute ECG display in which the SLIDE segment is also enhanced.

Referring to ECG CPU module FIGS. 6 and 7, the ECG CPU control circuits are shown and include the general means for generating the time-stationary displays of the present invention comprising the SLIDE, PAGE, and JOG displays. Thus, memory means are provided for storing a 3-minute interval of each channel of ECG signal and consists of suitable digital memories 90, 92 connected to the ECG digitized data output derived from ADC 32 and delay circuit 36 DAC 94 and smoothing filters 96 of FIG. 2. Addressing, loading and unloading, and control of these memories is undertaken by a dedicated Z780 microcomputer 102 connected to a computer data bus 100 together with associated PROM 104 and RAM 106. The computer operates through system I/O ports and I/O control select circuits 142, 144. Suitable clock and counter circuit 115 is provided for generating the clock frequencies of the entire system. The master clock runs at 7.86 megahertz and suitable frequency dividers provide other clock frequencies as required.

Refresh clock U-48 and other IC's that surround it. Also, specifically determine other wave forms like the right pulse and some refresh timing which is further division of the basis oscillator clock and that's done in a U47, U54 and U43. Those produce the refresh address and are distributed to other parts of the system to produce synchronous operations associated with digitizing the taped data so that it may be loaded into the memory.

Referring to the detailed drawing at the output of U55 and U43 indicate that 60 kilohertz signals 30 and 15 kilohertz signals generated for use in other parts of the system. Additionally, the entire group numbered 300 on the drawings serve as a fresh address.

A computer system data bus 100 connected to Z-80 CPU 102 102 serves to control the operation of the entire display ECG display system. PROM 104 is provided for storing the control softwear of the system. A RAM 106 is connected to the data bus 100 for temporary storage of data and other scratch pad purposes. A CTC (U-12) 108 is connected to the data bus and serves as a dedicated counter timer circuit for servicing the CPU. The CTC 108 is programmed by the CPU and softwear to define exact display time intervals and these time intervals define or determine durations of the display segments on the ECG CRT screen. It establishes uniform timing and the scanning and interruption of the display traces. More particularly, it defines the start and stop times for address codes of the various segments of the display depending upon whether the display is in SLIDE, PAGE or JOG.

Figure 8:
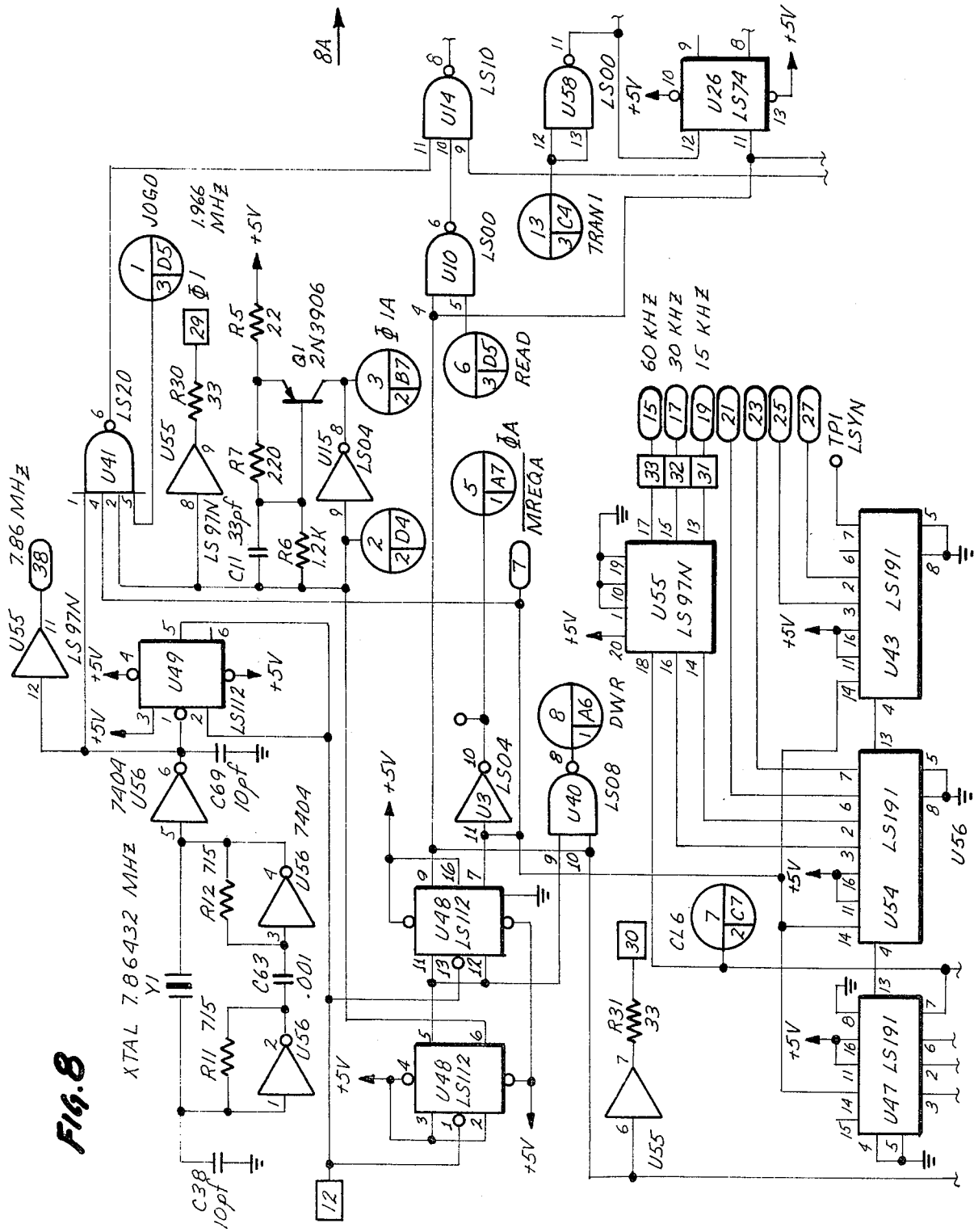
FIGS. 8, and 8A-8Z are detailed circuit diagrams of FIGS. 7 and 8.
Figure 8B:
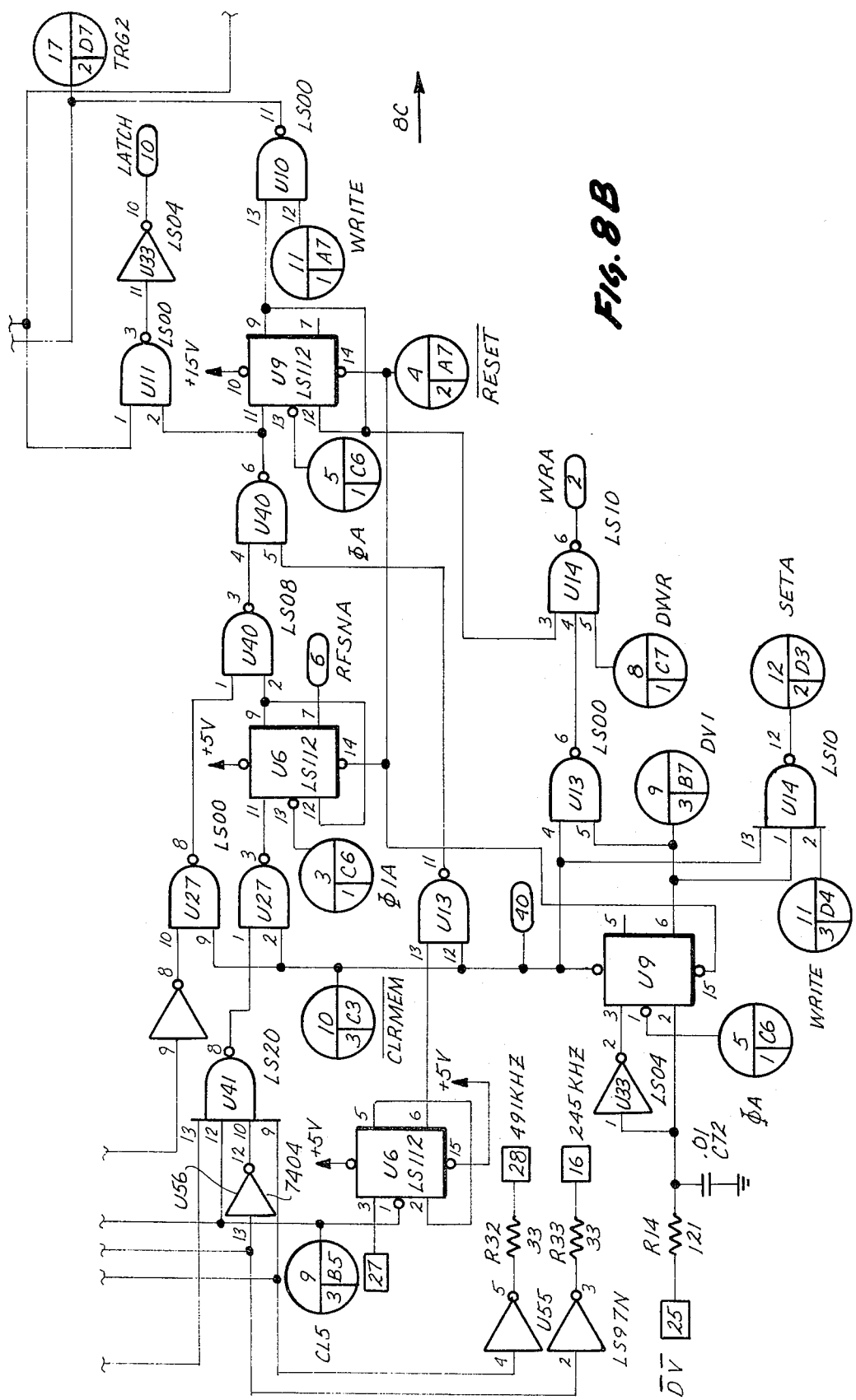
Figure 8C:
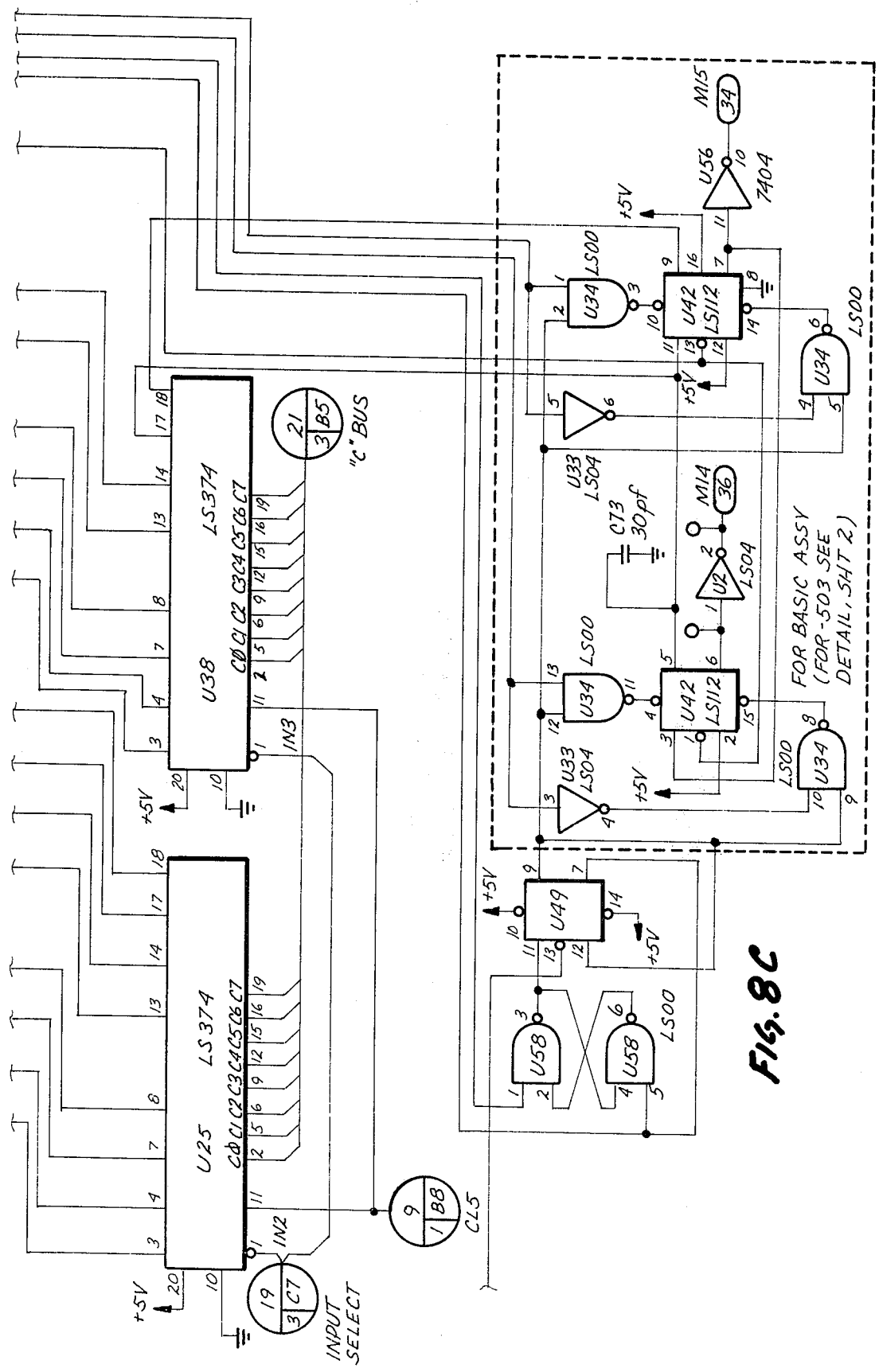
Figure 8E:
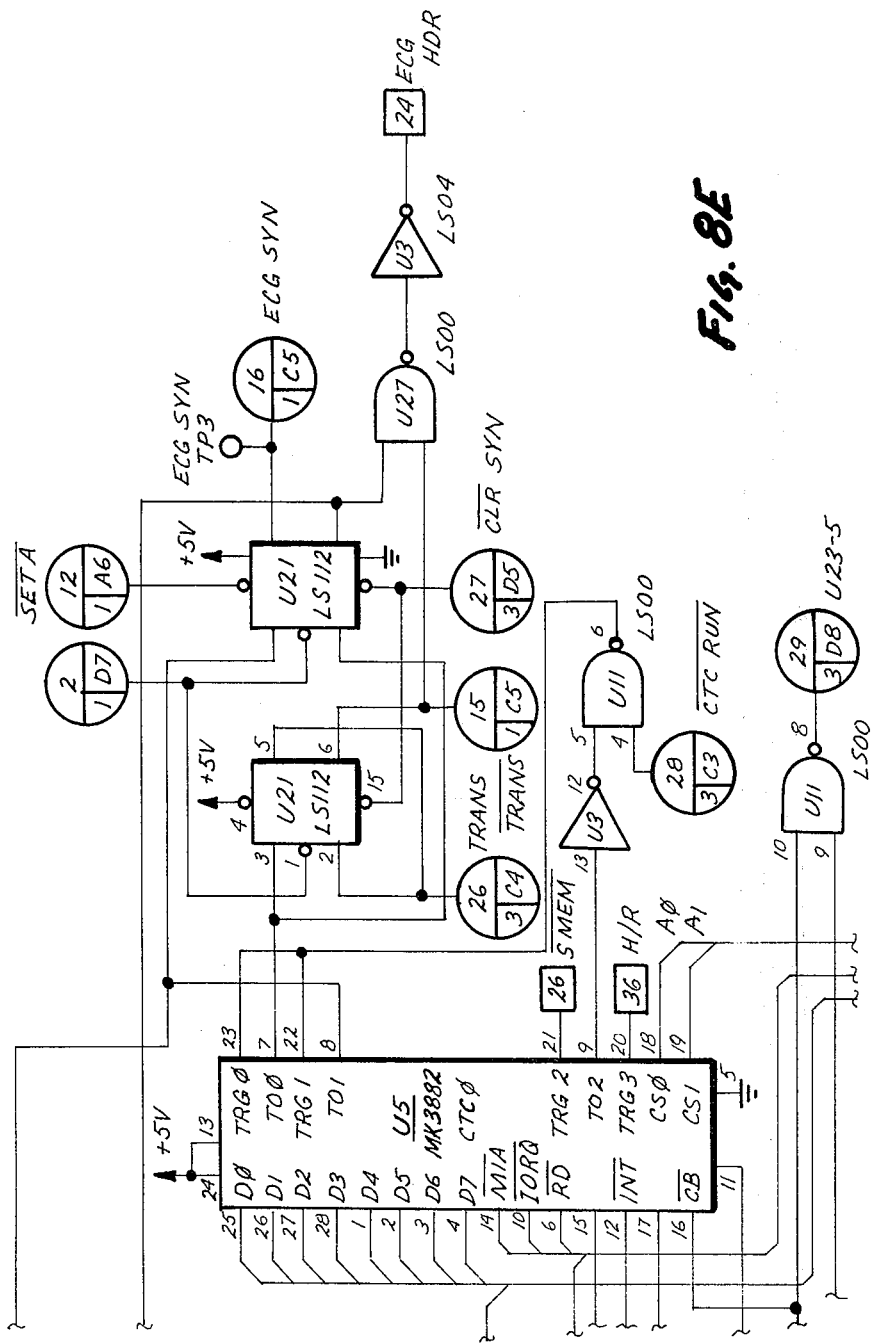
Figure 8F:
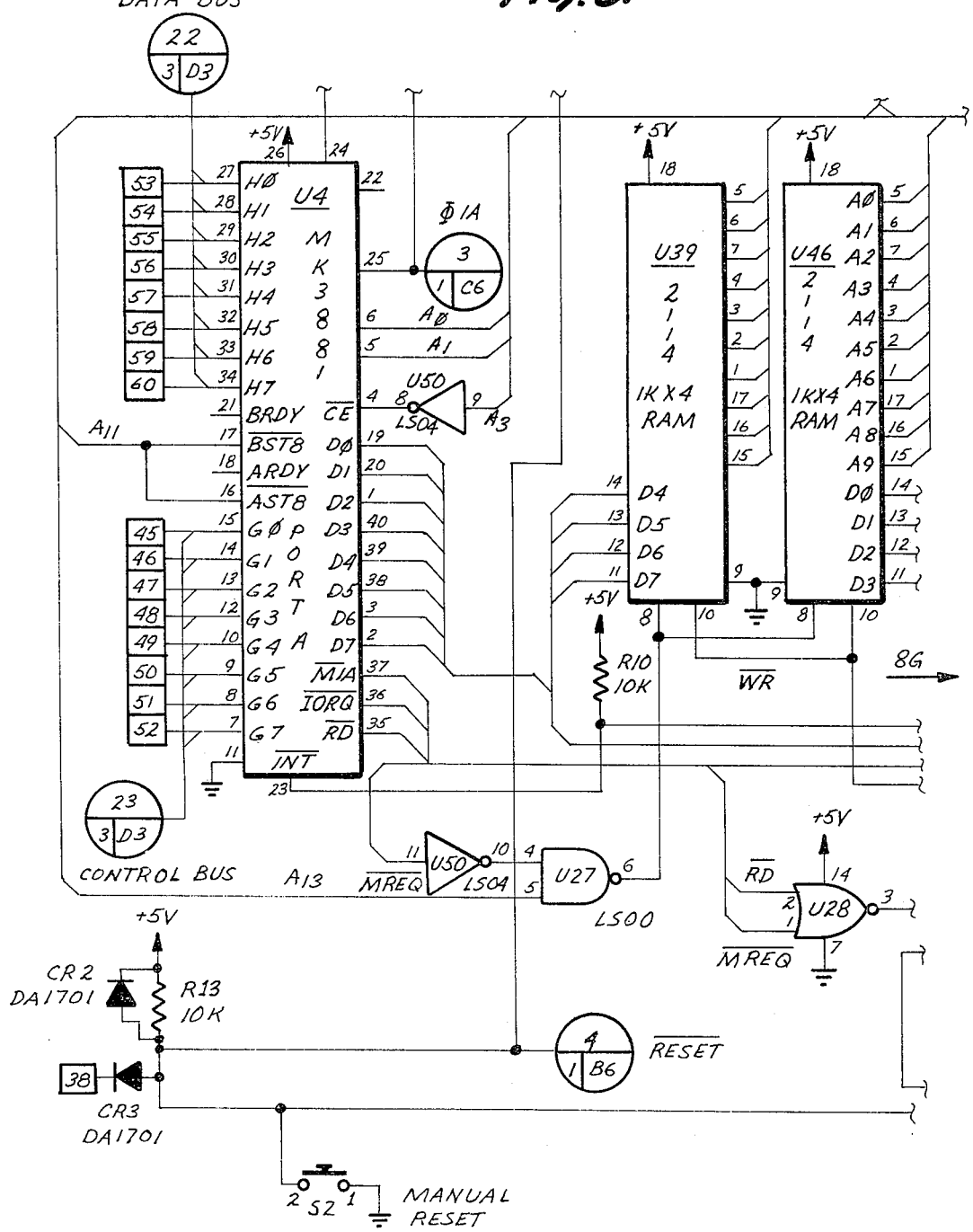
Figure 8G:
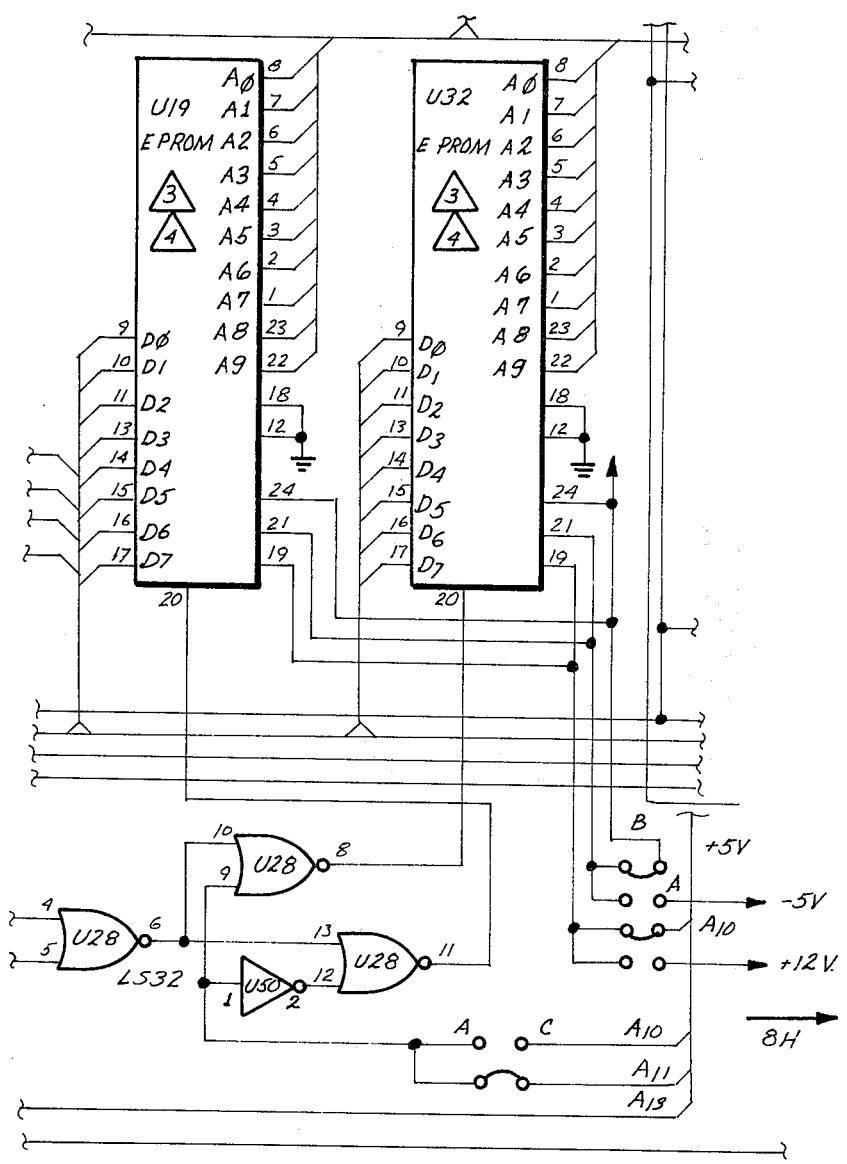
Figure 8H:
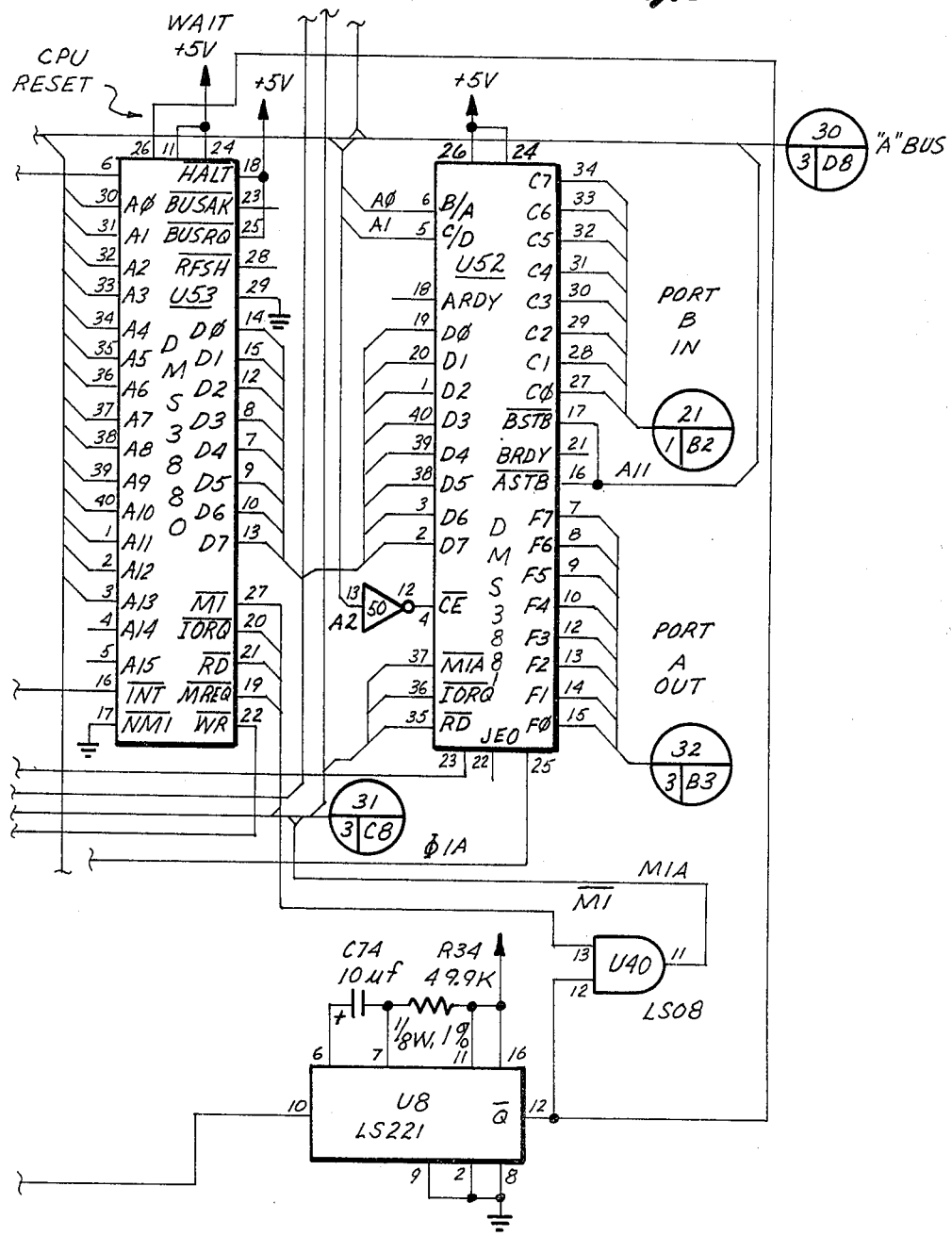
Figure 8I:
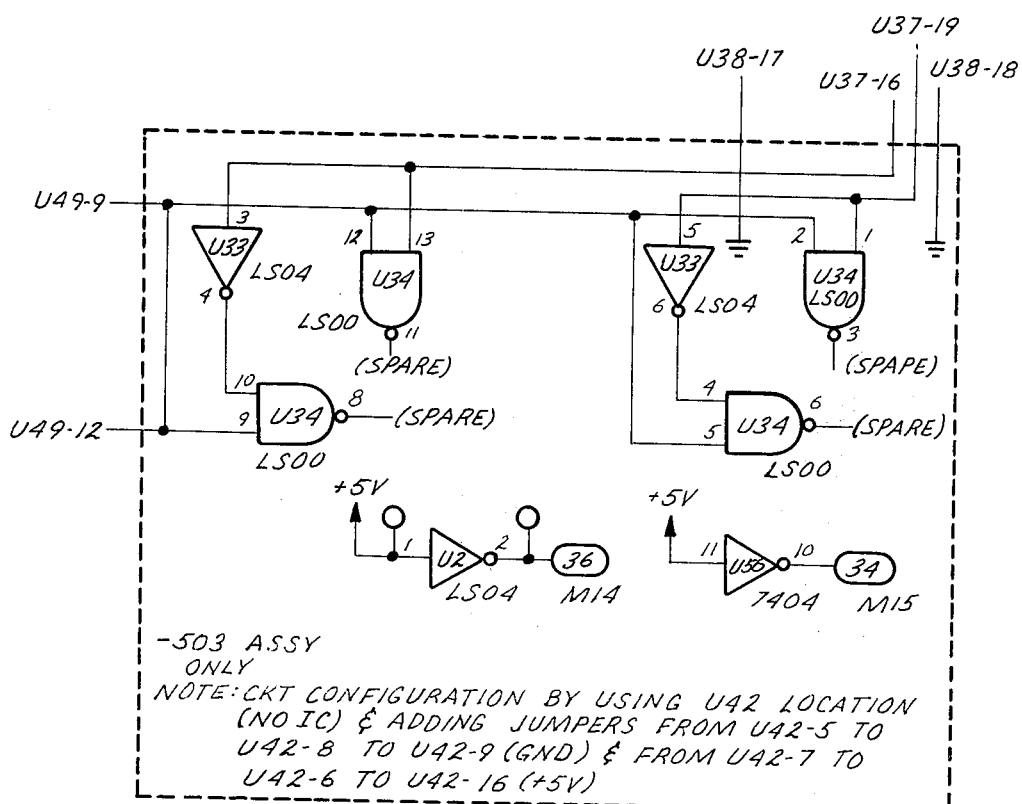
Figure 8K:
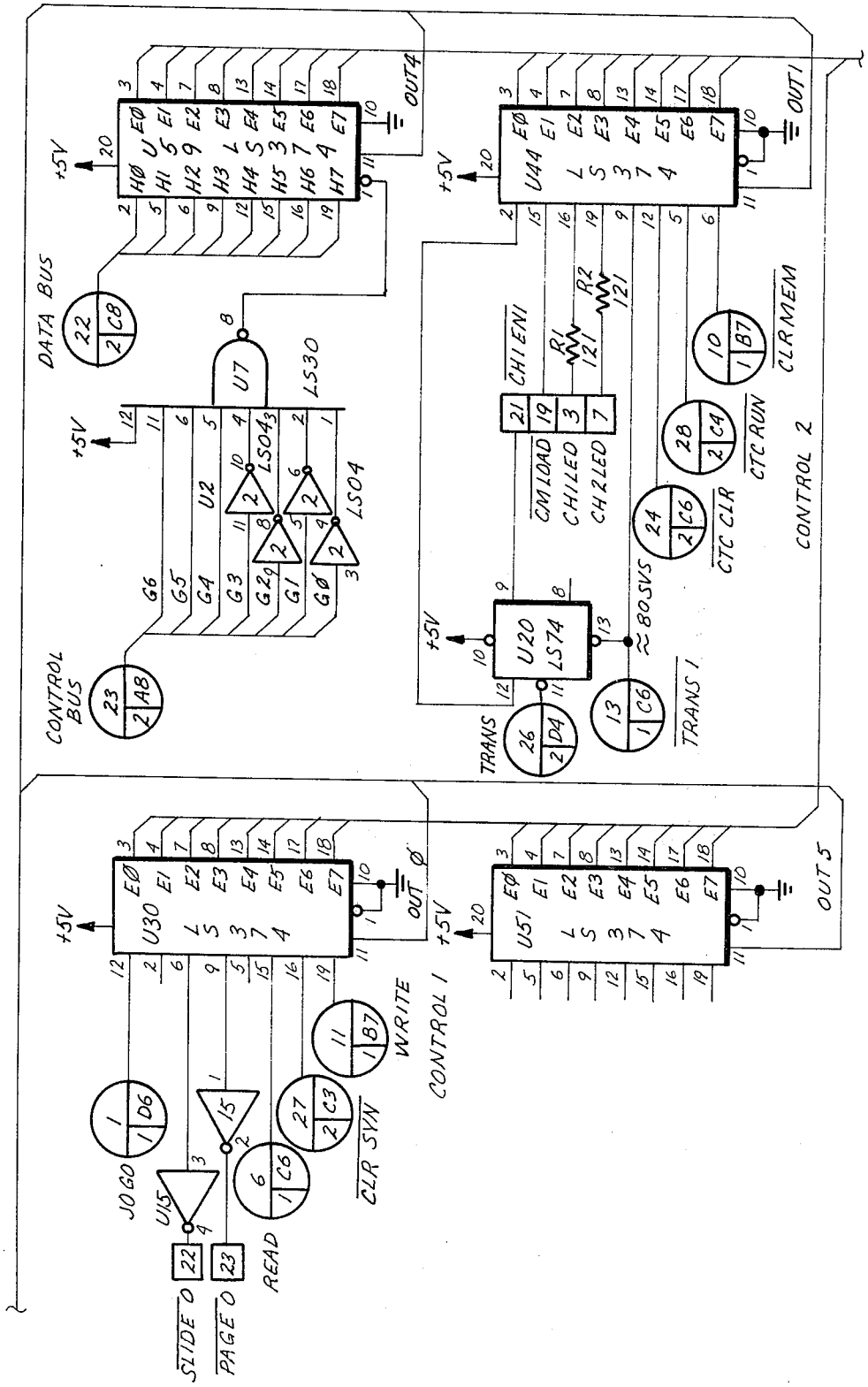
Figure 80:
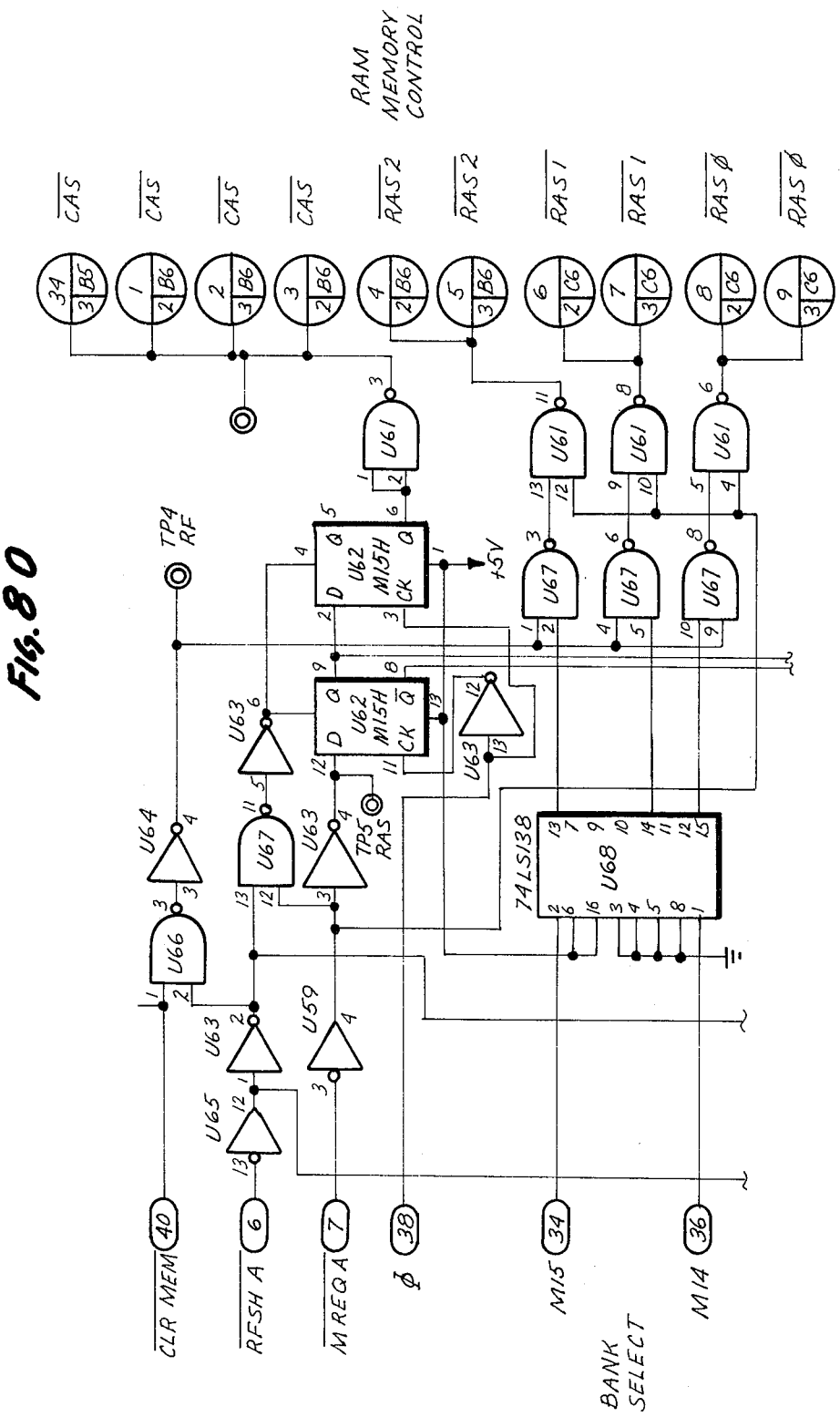
Figure 8P:
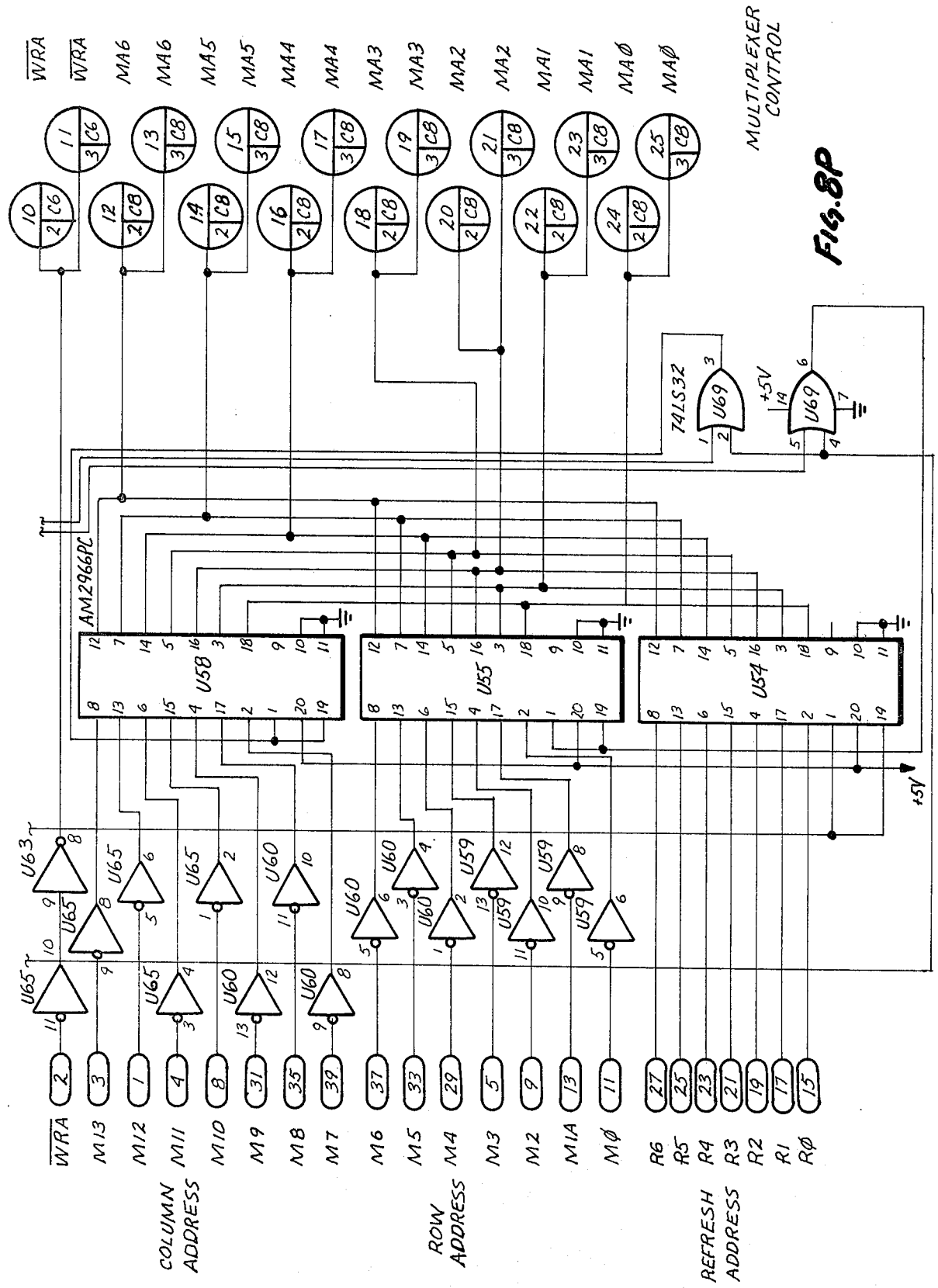
Figure 8R:
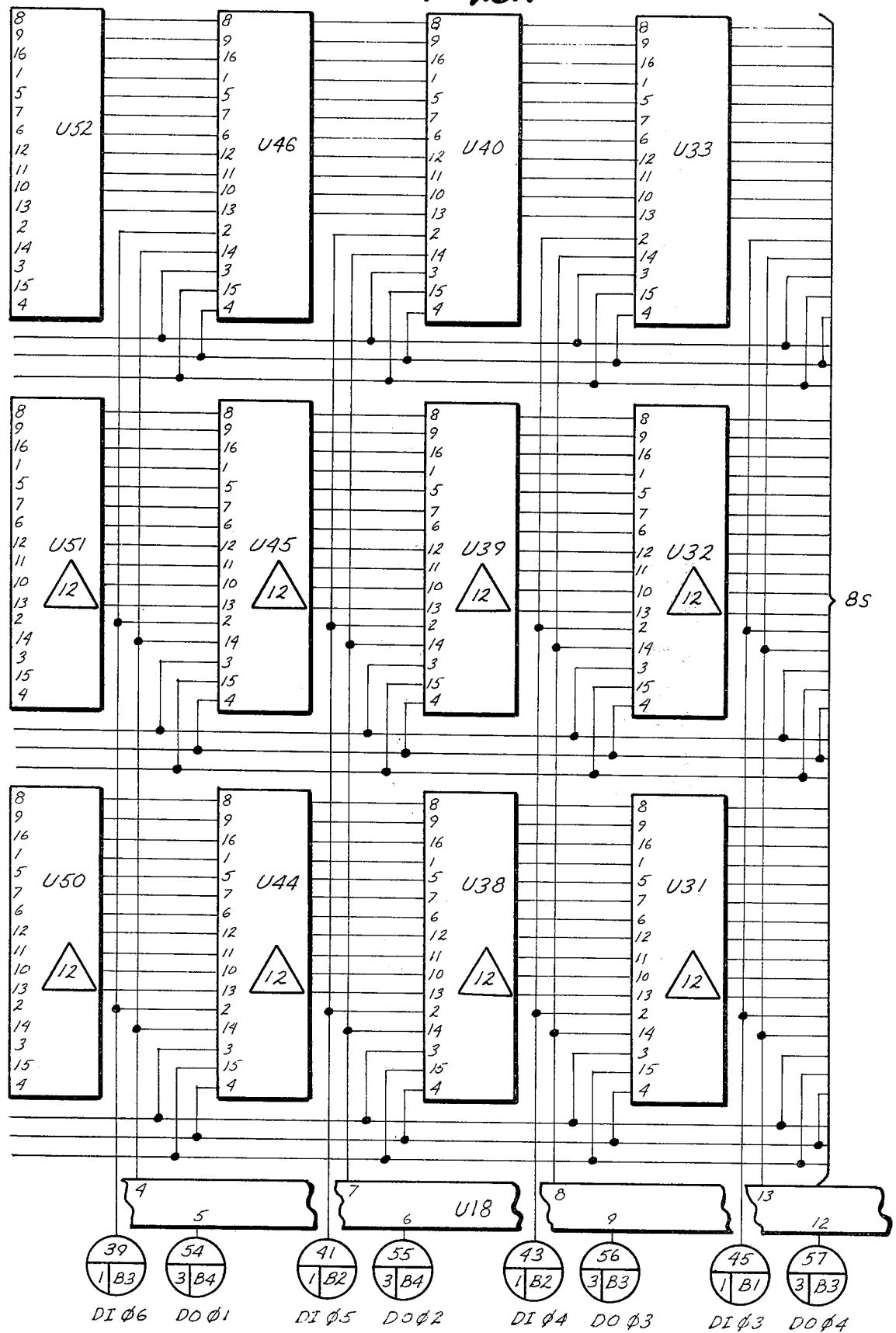
Figure 84:
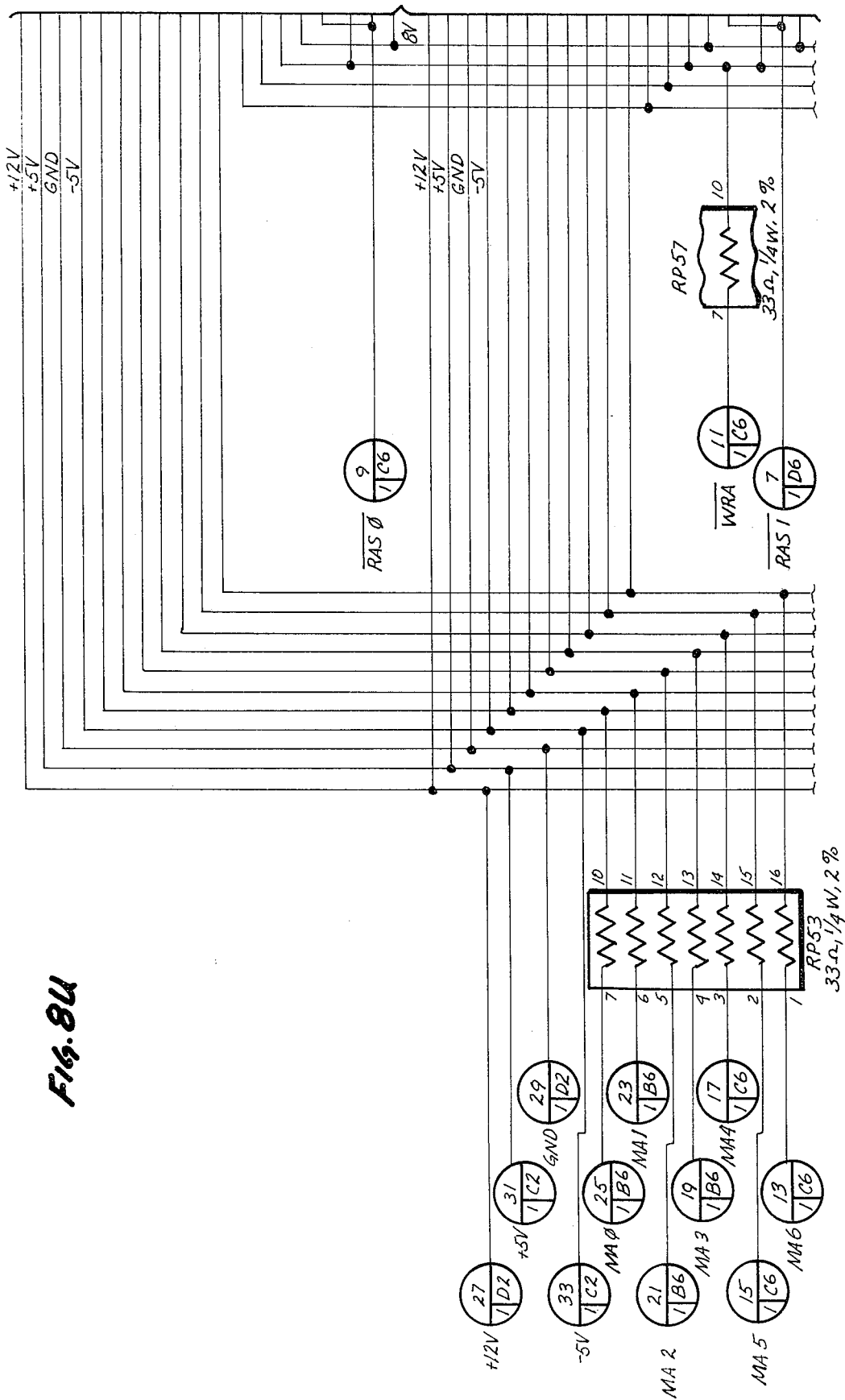
Figure 8V:
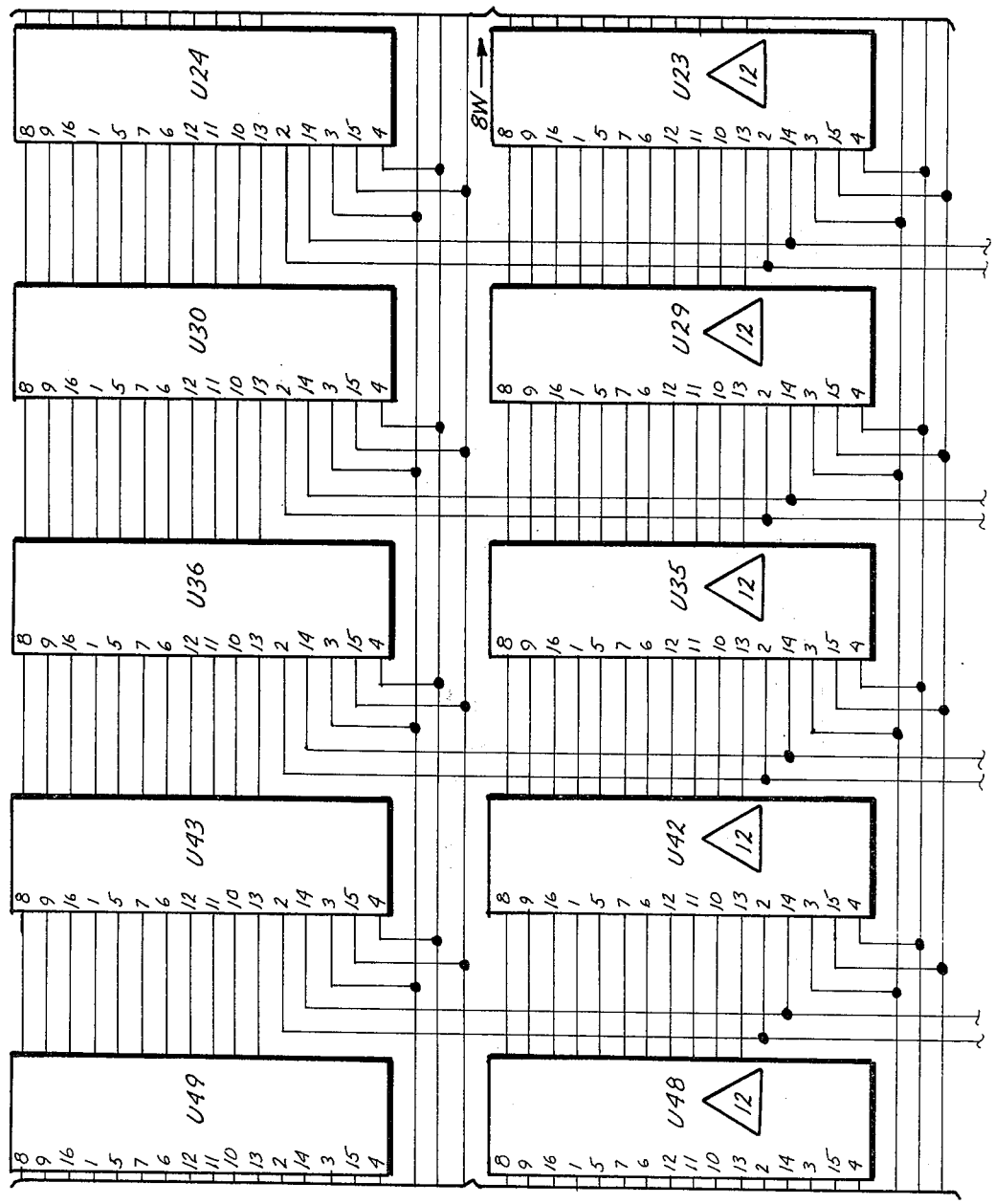
Figure 8W:
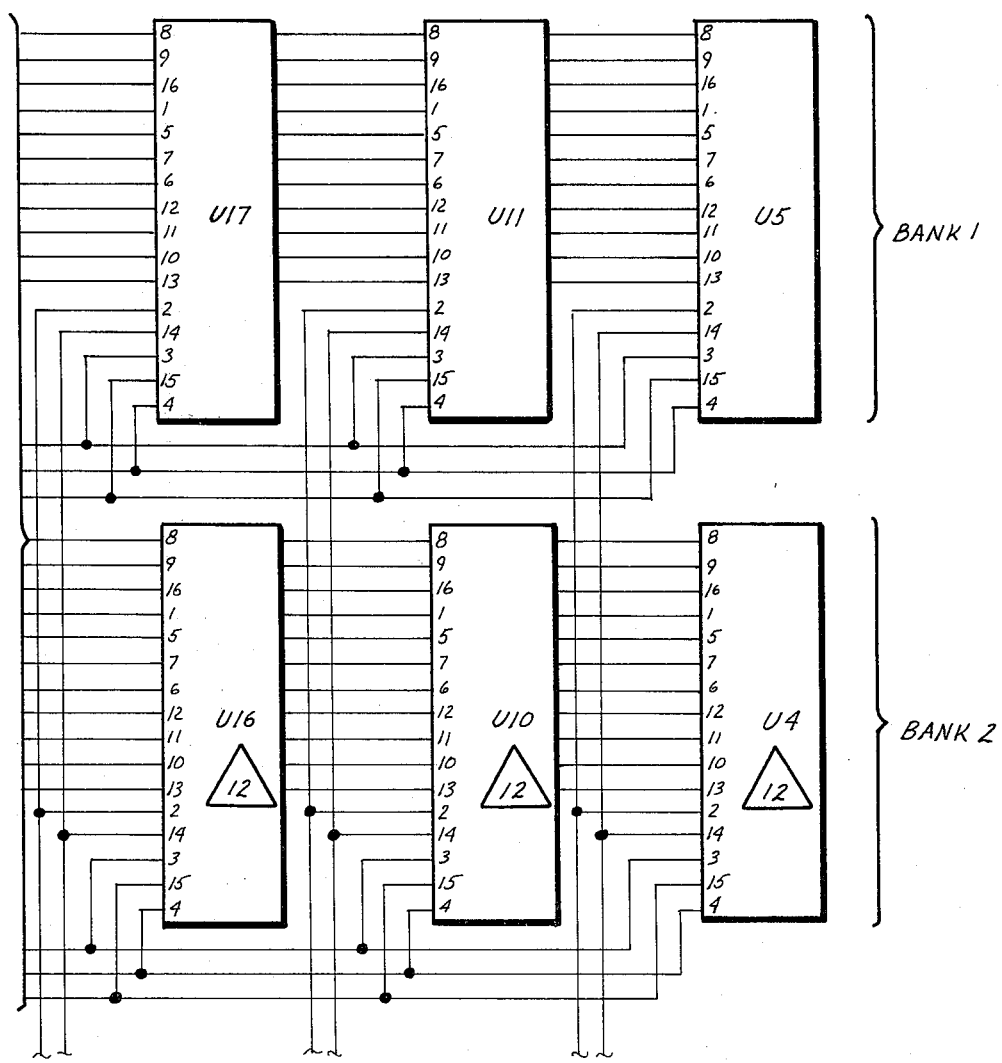
Figure 8Y:
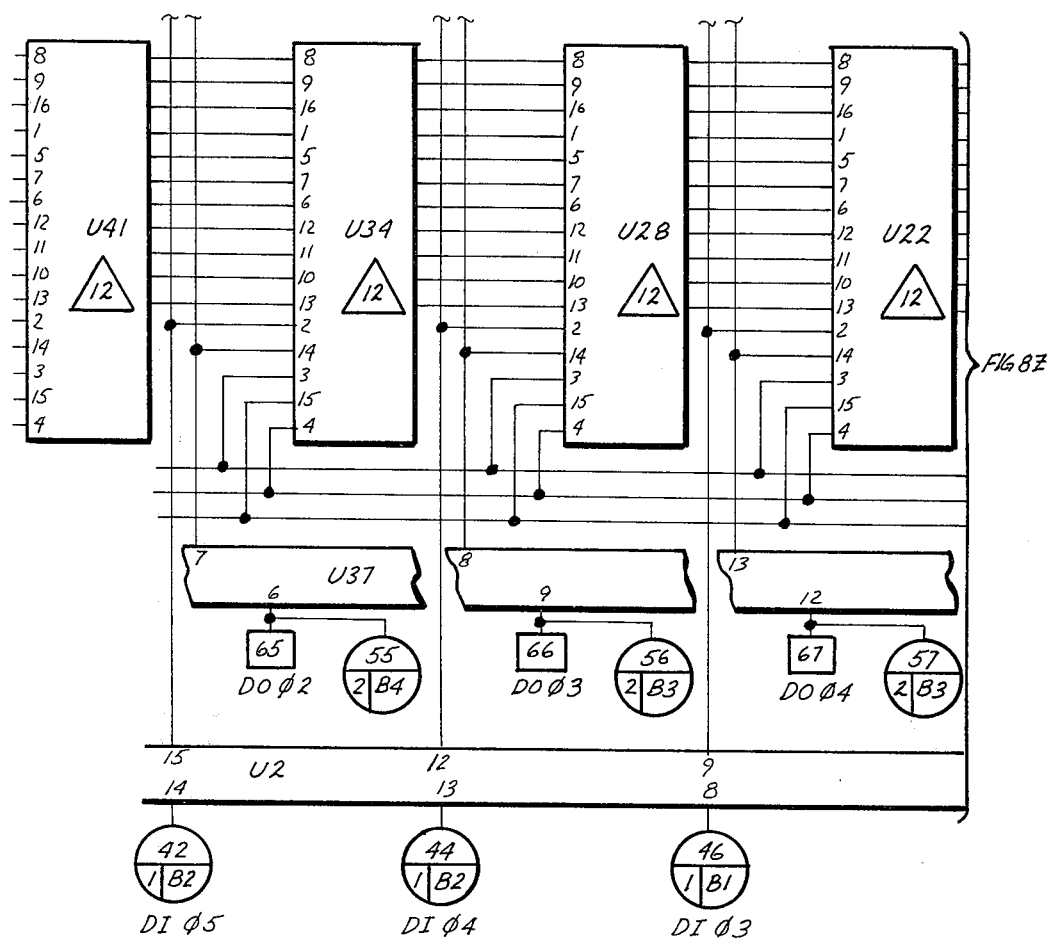
Figure 82:
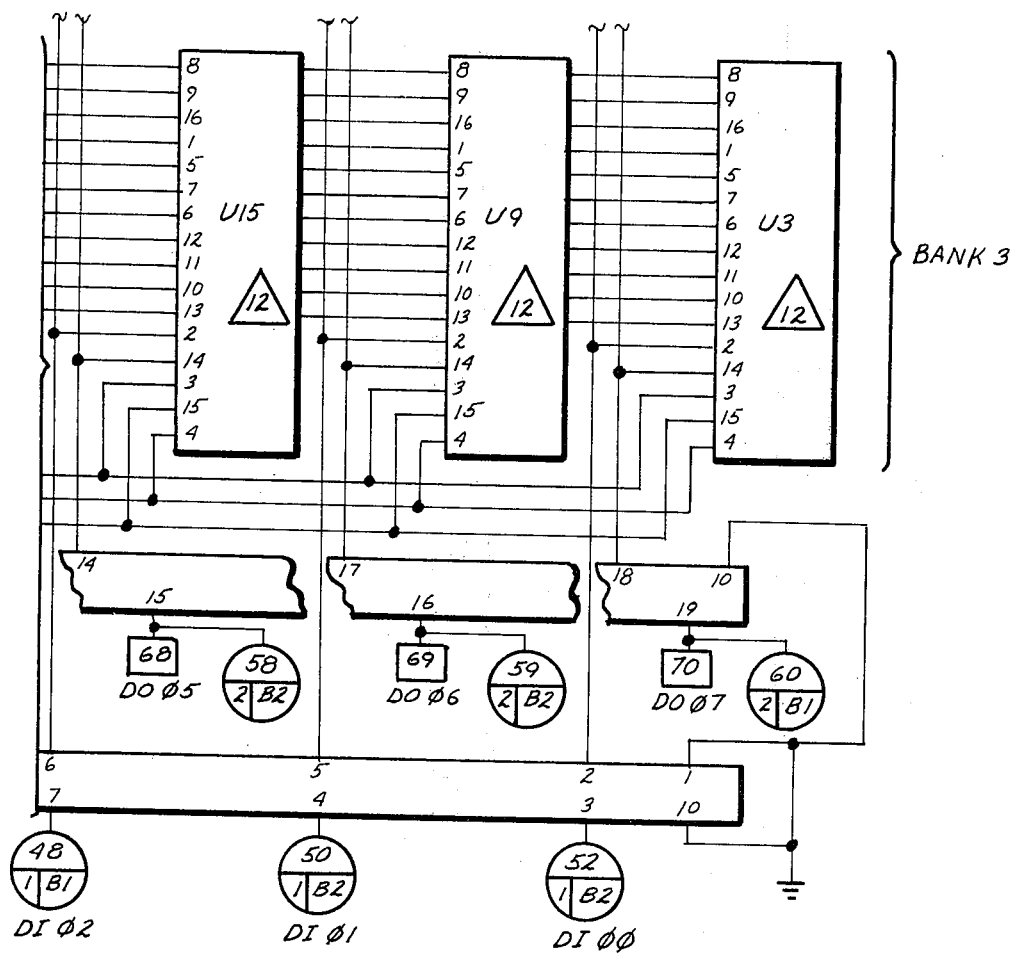

The CTC 108 is a programmable device which can either count events or count clocks within the system to define intervals very accurately. The memory is clocked such that a data sample is developed for every clock. The CTC 108 is clocked at the same time and therefore can define a data sample interval very accurately and issues control signals to the CPU indicating that the particular programmed interval has been terminated. The CTC is a trigger which defines the time intervals. The CPU responds to the end of any time interval and then produces the appropriate addresses which are used. The CTC is programmed to respond a known interval after the CPU sends it a number. That number defines the interval, so, once the CTC has started, sometime later, that number will eventually count down and that number will then issue a stimulus back to the CTU indicating that the interval ended. Then the CPU takes the appropriate action in preparation for the next interval. In one case, the CPU may load the same number back into the CTC, in another case it may be a different time interval corresponding to a different number that its loaded. In all cases the CTC provides a single timing pulse fed back to the CPU, when the timing interval that the CPU has requested it to time, has completed or timed out. The following description will include reference to FIG. 8.

Means is provided for enhancing a portion of the arrhythmiagraph trace in SLIDE mode or the 11 Second SLIDE segment of the PAGE or JOG MODE. This is preferably by Faxis intensification of the scope CRT.

U-12 is part of CTC circuit 108 and has an output of T0 and an output of T-01, the first of which is the intensification start pulse which is passed through flip flop U-1 and gate U-13 start portion to develop the intensification start pulse indicated in diagram 110. At a later time trigger circuit output at T-01 is applied through the lower half of flip flop U-1 to develop the stop pulse for the intensification which then is delivered to U-13 and returns the output to reference. The same trigger signals are used in the same way for the intensification enhancement regardless of the mode of presentation. Frame timing is accomplished by U-5, again block 108 of the block diagram wherein the T-00 output pulse and T-01 output pulse combine in flip flops U-21 to produce ECG SYNC and horizontal SYNC drive.

The system is further defined by an I/O output control data bus 156 which is accessed through I/O port 112 (U52) to data bus 100 and by a second I/O input control data bus 157 which is accessed by I/O port 114 (U52) to the system CPU data bus 100. The general function of the input I/O output bus and I/O input bus 156 is to control the states of the circuit which are directly responsible for producing the various displays. This is the means by which the CPU communicates with the various elements of the display system. More specifically, the I/O output bus connects through OUT 0 latch 154 to system control 155. The input I/O bus 157, which communicates through I/O 114 to the CPU, has an input latch 116 connected to keyboard (pushbutton) system 118 and IN 1 port latch 120 which connects to system status and various other circuits. An example of the functions indicated for keyboard are SLIDE, SCAN, PAGE selection, left and right slider movement selection and the like, while system status indicates data valid, jog line used to progressively shift entire JOG memory segments.

The I/O input bus 157 also connects to input latch 3 and in latch port 2. These latches are connected to a counter system 130 consisting of counters U-22, U-29, U-36, U-35 numbered 132, 134, 136 and 138. Each of the counters has a four-bit output which are summed together to give a 16 output on memory address bus 140. An input I/O control 142 serves as select mechanism for controlling which of the devices connected to I/O bus are selected for operation while a similar I/O control (U-23) 144 is connected to select which of the devices connected to the I/O output bus is used. I/O controls 142 and 144 may be considered as dispatch circuits. Each of I/O controls 142 and 144 are connected to the CPU on independent control lines. I/O output bus 156 is similarly connected to CPU in parallel with I/O input bus. The output bus communicates with the counter to indicate that the out latches OUT-2 and OUT-3 150 and 152 are located via I/O 412 from the CPU data bus and CPU. After both OUT 1 and OUT 2 are loaded, they are enabled by a suitable circuitry to transfer a start count to counter string 130. OUT-0 and OUT-1 154 and 156 are miscellaneous outputs which are sent to system control points for other purposes. Refresh clock 160 supplies the refresh address to the ECG memory for the purpose of maintaining data since the memories are constructed of dynamic RAM chips.

There is one portion of the memory 13 that is slightly modified. Counter block 138 (U-35) only conveys two of the lower bits of address data to the memory. The upper two bits are not used as part of the memory address. That portion of the circuitry is formed of U-42 and its associated gating.

U-42 serves as a three times counter which when multiplied against the U-132, 134, 136, 138 gives a 48K addressing range required for the scope of the 48K memory.

Control over the CTC U12 is accomplished through the data lines D0 to D7 input lines of U12 and some additional associated control lines which instruct the CTC that some of the data being written to may be a control number for slider position whereas some of the data written to it may be a control word or other subsidiary function.

The devices U39 and U46 (RAM) serve as a scratchpad memory and the control program is written into EPROMs U19 and U32, all of which serve to service the CPU chip microprocessor U53.

The U-52 is a PI/O chip used to permit interfacing to all other circuit hardware. It supplies a pair of ports through which all input data is collected and all output data is written. The input port collects keyboard data and also gives the two bites of information from the memory address counter which define a tape stop time location in memory. Tape stop time correspond to a specific stop address in RAM memory when a tape load has completed, and also when the system state needs to be changed. The output port, which is port A, is used to latch the new system state; that would be OUT 0, OUT 1, OUT 2 and OUT 3 latches. OUT 2 and OUT 3 specifically are used to control ECG display memory data accessing while OUT 0 and OUT 1 are two exit latches that control system state by the particular pattern of bits that may be written into it. Those bits always establish whether the system is in tape load, memory read, or memory write and/or ground state whatever may be demanded on the basis of the last sequence of the last unprocessed input data that was received by the CPU.

The memory address counter which is responsive for either loading data into the ECG display memory or extracting it from them, depending whether it's a tape load cycle or a display cycle, are composed of U22, U29, U36 and U35. In addition, there are several other IC's that make this a 3-bank counter as opposed to a 4-bank counter and that function is produced by U42 together with U34. Outputs become N14 and N15 at 1036 and 1034 are connected to the ECG memory bank select to be described. The memory address counter U22, U29 and U36 and the other IC 242 are reach through two latches which happen to be controlled by IN 2 and IN 3 strobes which the CPU issues to interrogate the contents of that memory address counter so that after a tape load has occurred and a tape stop has occurred, the last memory cell loaded in the CTC memory can be read into the CPU and consequently from that single number all of the other segments (15-second segments) of the data can be computed by subtracting a constant to establish the last three minutes of tape data that has been coded into the memory. Only one number is needed, and this is essentially the only time that the latches are actually interrogated, but they have to be interrogated at least once after each tape scan and to establish this point and to compute the numbers. Since the exact instant when the tape stops is not predictable, this number can be ranged over the full number scheme of 0 to roughly 48K of address. Latches U24 and U37 are controlled by OUT 2 and OUT 3 and as a cross-reference, they are shown diagrammatically or in a block form, and they are used depending on the particular display mode, they are used to load the memory address counter with the desired display with a desired address and that address then accesses certain memory for display. The counter is loaded through the latches and that selects a specific region of memory for presentation on the screen.

U25 and U38 latches read the content of the memory address counter and they are only used at one time during the operation, and that is when the tape mode operation has ended. At that particular time, U22, 29, 36, 35 and the other IC's in the counter have a number in them which corresponds, which is an address and corresponds to the last bit of data which was loaded into the ECG memory during the last tape scan.

I/O control circuits U16 and U23 are used to select the various latches that are involved in either data output or data input, the two functions are mutually exclusive such that a data input and output will not occur simultaneously. Data output U23 selects a specific latch by virtue of one of its outputs going active and then whatever data happens to be present on the data bus at that time presented at the input of a specific latch. Only the latch which is selected will get that specific data written into it. The data that appears at the port A output bus is buffered by U57 presented to all of the output latches. However, only the specific latch selected by one of the output select in U23 will be the one that receives the data while the other is maintaining the data that has already been written to it at some previous time. These outputs then control the states of peripheral hardware which is needed to support the display and other functions that the CPU performs. U16 is an input select and that permits reading of the various operator inputs or data from the memory address counter which are controlled by IN2 and IN3 covered in a previous few words of discussion. The operator presses a specific button, but until it's interrogated, the data of that particular latch will not be read in by the CPU unless a specific select has been applied to it so that, in the case of an operator pressing the PAGE PB, it is fed into U18 and that data would be latched into U18 at the input but it would not appear at the output until the N1 signal at U16 and U13 was asserted to select the U18 contents and apply it to the C bus which would then be connected to the input ports of U52 and thereby the CPU would then recognize that the operator has pressed the push button of the PAGE PB push button so that the appropriate sequence would be initiated to start processing this fact.

The memories 90, 92 are each organized into two channels; 48K data bits by 8 data bits for 3 banks in each channel and data is supplied to the RAM through its data input lines. Data is supplied to both channels. In the case of Channel 1, the data is latched in and held since the bus structure that feeds the two channels is identical. The data is multiplexed such that Channel 1 data is immediately followed by Channel 2 data and then Channel 1 data is applied at the data input lines again. The latch is necessary so that when a write cycle occurs of data into a specified memory cell within a specified group of memory cells, within the memory the latch signal holds the data for Channel 1 and then since the write cycle occurs during the time slot that Channel 2 data is present, there is no latch needed for Channel 2 data since that is the data that is present at that instant and consequently Channel 1 data is held over in the latch and then written into Channel 1 memory and at the same time since data for Channel 2 is presented at the data input pins and the write pulse occurs at that instant, thus, Channel 2 data is written into the Channel 2 memory.

A multiplexe4 composed of U58, U55 and U54 controls the memory loading sequence by applying a timed sequence of address data to the memory in such a way that one of 16K addresses is selected for writing into the row address and is applied first through the select that connects to U58, U55 and U54. Those selects are generated in the timing circuitry the memory cycle control circuitry. M0 through M15 addresses are already stable, but only M0 to M13 are multiplexed. The sequence of events is that the row address is applied first. It is latched in the internal structure of the 4116 RAMS which compose the 48K memory array for each channel and then following a certain time interval the M0 through M16 bits no longer apply to U55 to the output structure because they have already neen latched by the RAM due to the control signals. Then the M7 through M13 bits are applied to the output of U58 which is also connected to the address inputs on all of the RAMS and that address is latched and this information then establishes which particular cells of the memory are being read from or written into. The only distinguishing feature between the two modes is that the write A signal, pin 2 U65 1011, is active in the write cycle and is inactive during any read cycle that may be occurring from the memory. M14 and M15 outputs are fed to a decoder that selects one bank out of the three banks that compose each channel, so that a bank select together with the multiplexed address are required to actually address or write data into any particular cell in the memory. The data is volatile since this is dynamic RAM so that periodically a refresh address is applied during the refresh memory cycle which also is connected to the control circuitry during that cycle the refresh during a specific row of data will occur in memory and the memory reads and write functions are temporarily suspended.

The general layout for this frame timing uses 4 channels within this CTL unit. Two of them are directly related to producing synchronizing pulses that produce a stable display on the screen and define the various time intervals so that ECG data can be displayed on the screen. The two outputs of the ECG are the T0 time OUT-0 and time OUT-1 which are then detected in the 2 flip-flops U21 resulting in a ECG vertical and horizontal timing to produce the stable display on the CRT.

Referring now to Figure, two channels of U12 (TØ, TO1) are used to produce a gating pulse that intensifies the output trace in the region where the slider happens to be currently positioned in any of the displays that happen to be the current display mode. The method of operation is such that the CPU loads the 2 CTC channels, one of the channels with the start a number address that corresponds to a start of the intensification and another number which corresponds to the end of the intensification interval and then when the two channels are at the end of their time period, the pulses that are generated toggle the hardware which is composed of U1 and U13 and 11, and the sum of the 2 slip-flops U20 and U26. These produce the intensification pulse that defines a brighter patch on the display screen. The position of the slider is a CPU computer number, is maintained internally in RAM storage area, and that particular number is then rescaled so that it fits within the time frame of the particular display mode and the scaling has to differentiate depending on what the display mode is because a different time interval is represented by each of the displays.

Referring again to the clock circuitry, the master oscillator runs at 7.86432 MHz and all other timing in this circuit is derived from this rate to generate many clock signals used by other portions of the system. The 7.86 MHz signal is buffered at U55-11 and used by the ECG MEMORY in memory cycle timing and is also gated at U41-6 to produce the special memory address counting required in JOG Mode (described in subsequent section). Additional frequency division at U48 results in a 1.966 MHz output which is routed to U15, Q1 and other components which form the clock driver for the CPU, CTC's and PIO's (U53, U12, U5, U4, U52). Other outputs of U48 form MREQA and DWR which are used to define the ECG Memory read and write pulses. Further division of the input frequency at U47 is decoded so as to produce a refresh enable for the ECG Memory which occurs once every 8 memory cycles (U6-7).

Stages of division in U54 and U43 result in outputs which are used as the Refresh address (7 bits) for the ECG Memory. At the end of the timing chain is TP1 which may be used as a sync for observation of all higher frequency waveforms on this assembly. The ECG Memory Address Counter (U22, 29, 36, 35, 42) is under the control of the CPU and is used to manage data transfers into and out of the ECG MEMORY. U42 is connected as a modulus 3 counter making the count length a maximum of 49152 (16K×3), which is the size of the ECG Memory. Input clocks to the counter string are controlled by the CPU via gate U14-8. During data write time, the clock source is U14-9 and is a maximum of 61440 Hz corresponding to 256 samples per second at 240 rate. During SLIDE and PAGE modes, the clock source is U14-10 and is constant at 983 KHz. The JOG display clock source is a combination of the clocks at U14-10 and U14-11 which effectively becomes a clock rate of 2.949 MHz to allow display of the entire contents of memory in 16 msec.

To select data for display, a count value may be loaded into the counters by the CPU using the strobes from one of two sources. TRAN1 is CPU issued and TRANS is generated as a result of the timing out of a program-controlled constant in CTC Channel 0 (U5). Both of the strobes are generated non-synchronously with an ECG memory data access cycle and the SR flip-flop formed by gates in U58 and the JK FF U49 serve to synchronize these signals. It is necessary to synchronize the transfers of the counter data in order to avoid modifying the current count value during a critical portion of a memory cycle which can have the effect of destroying an entire row of stored information.

FIG. 9 shows the general block diagram for timing and display on circuits to which either AVSEP or ECG data is taken from DAC 194, buffer 196, and filter circuit 198 to the X axis MUX Switch 200 through a vertical axis driver amplifier 202. Input data is received by DAC 194 from either the AUSEP memories or from the ECG memories. Position and gain amplifiers Selects 204, 206 are provided as well as sawtooth Horizontal Sweep as developed from drive Signal line 210 borrowed from the Horizontal Sweep to be described in connection with the X axis. The step generator 209 controls base line position. System logic control 210 causes the R wave of signal to trigger sawtooth generator of 212 which drives horizontal MUX switch 214 and horizontal drive amp 216.

Figure 10:
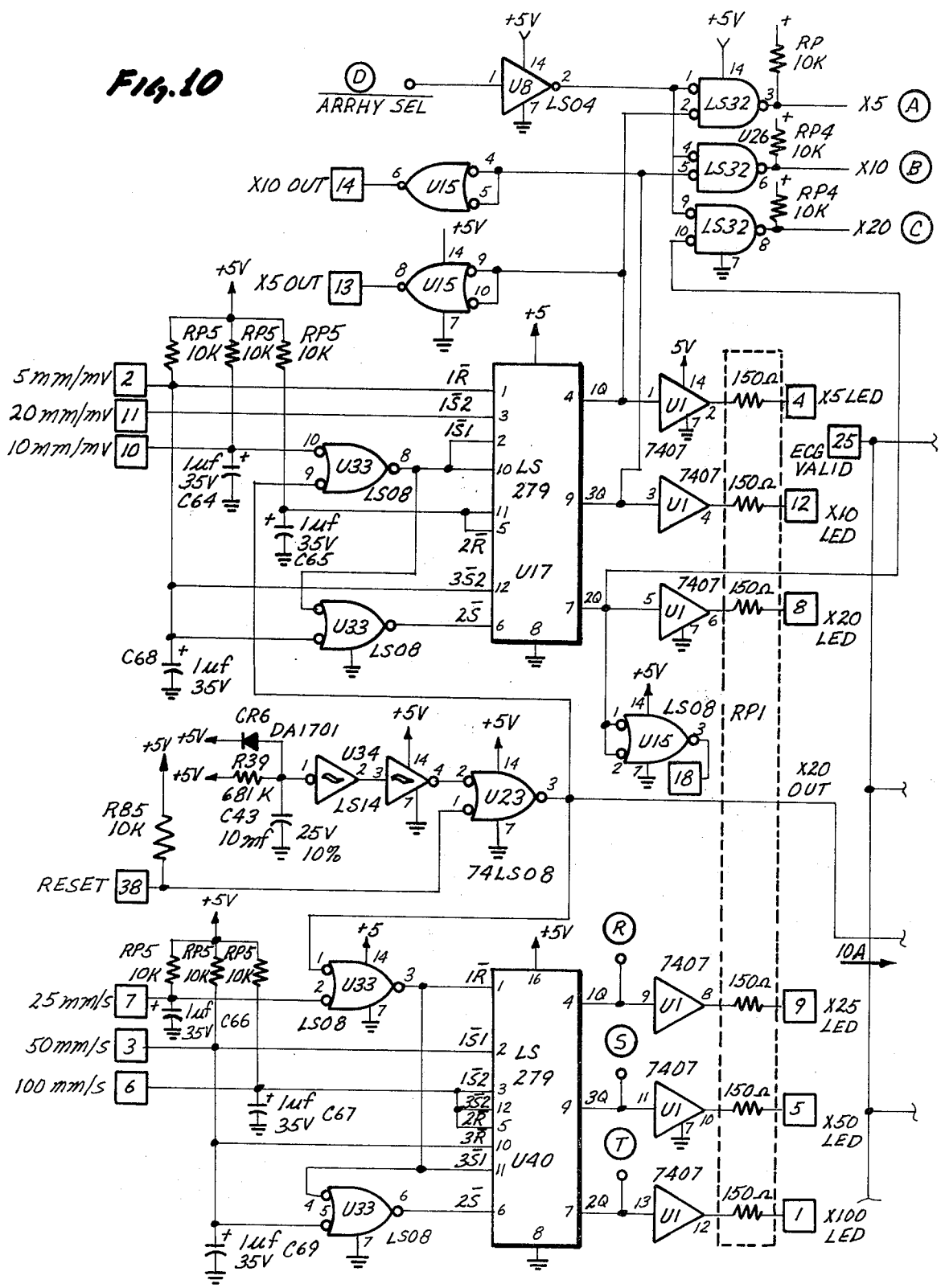
Figure 10A:
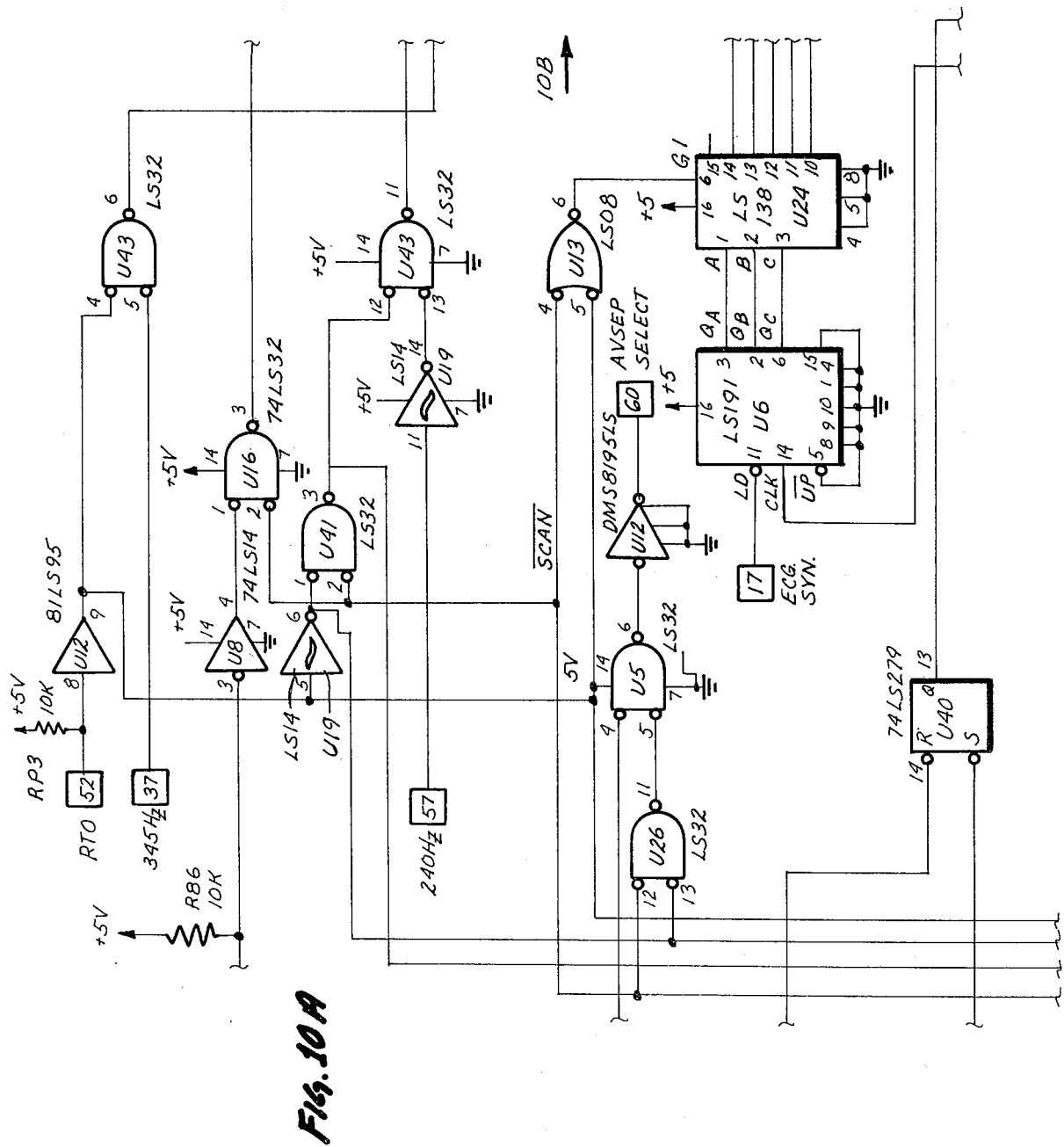
Figure 10B:
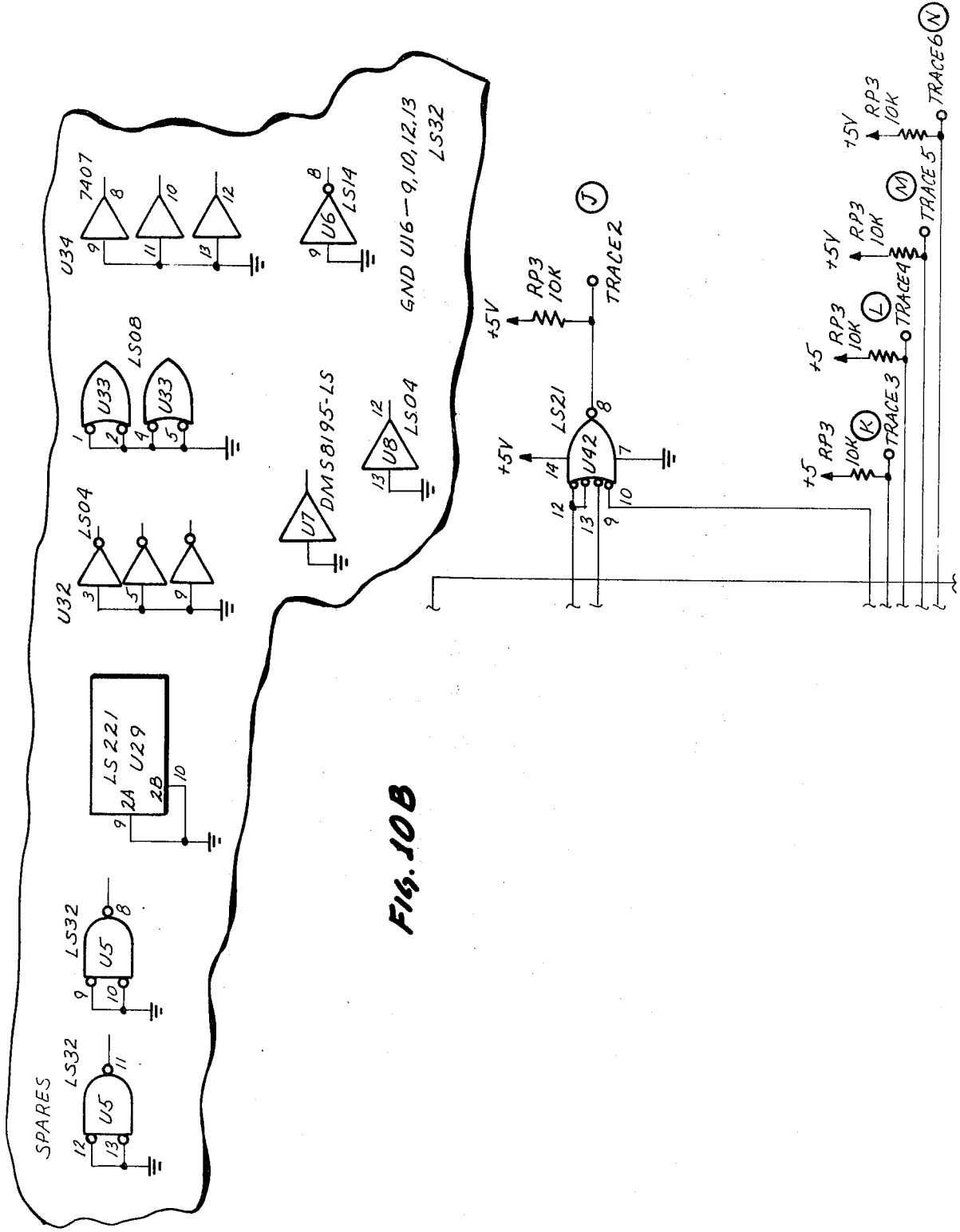
Figure 10E:
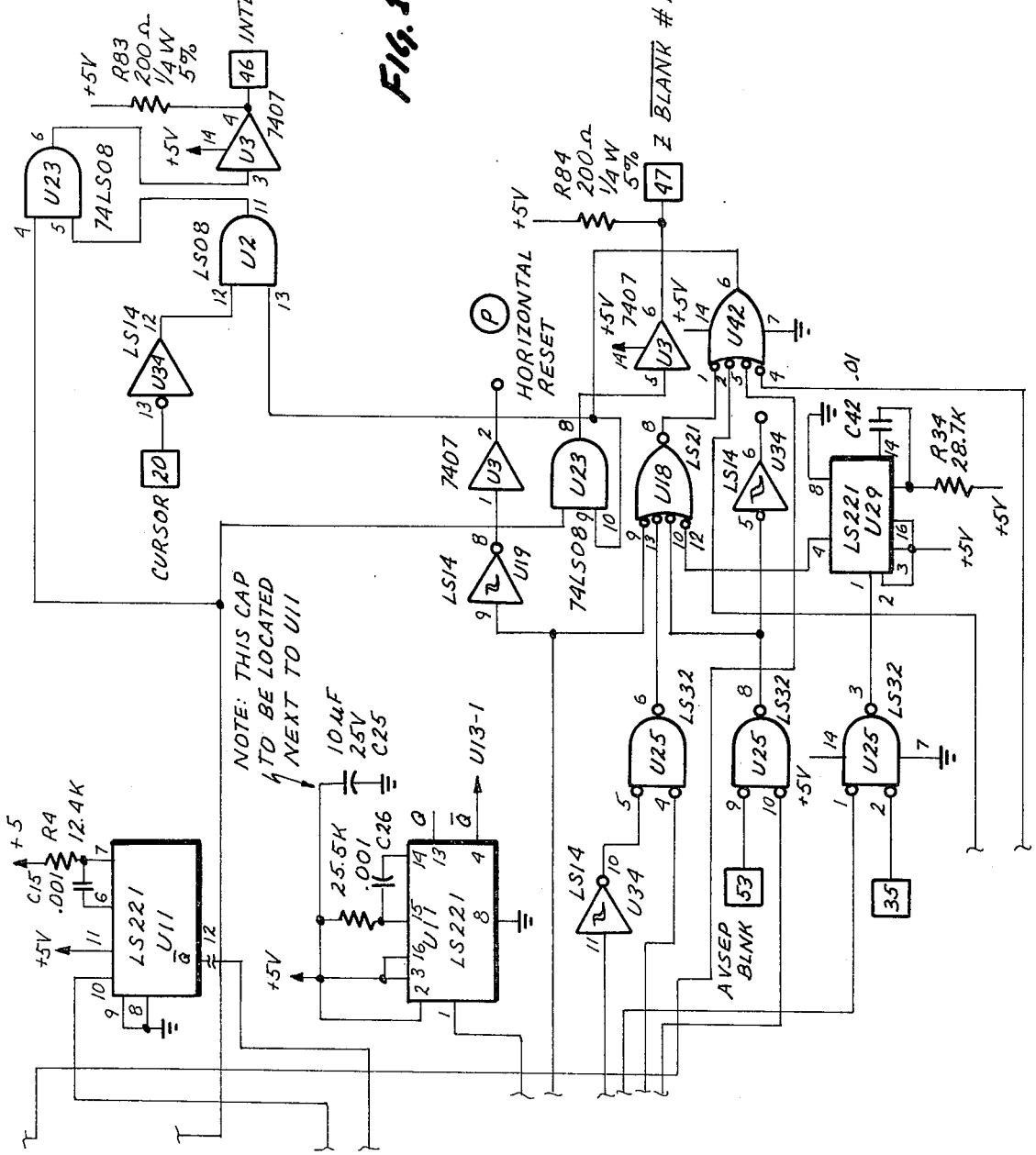
Figure 10F:
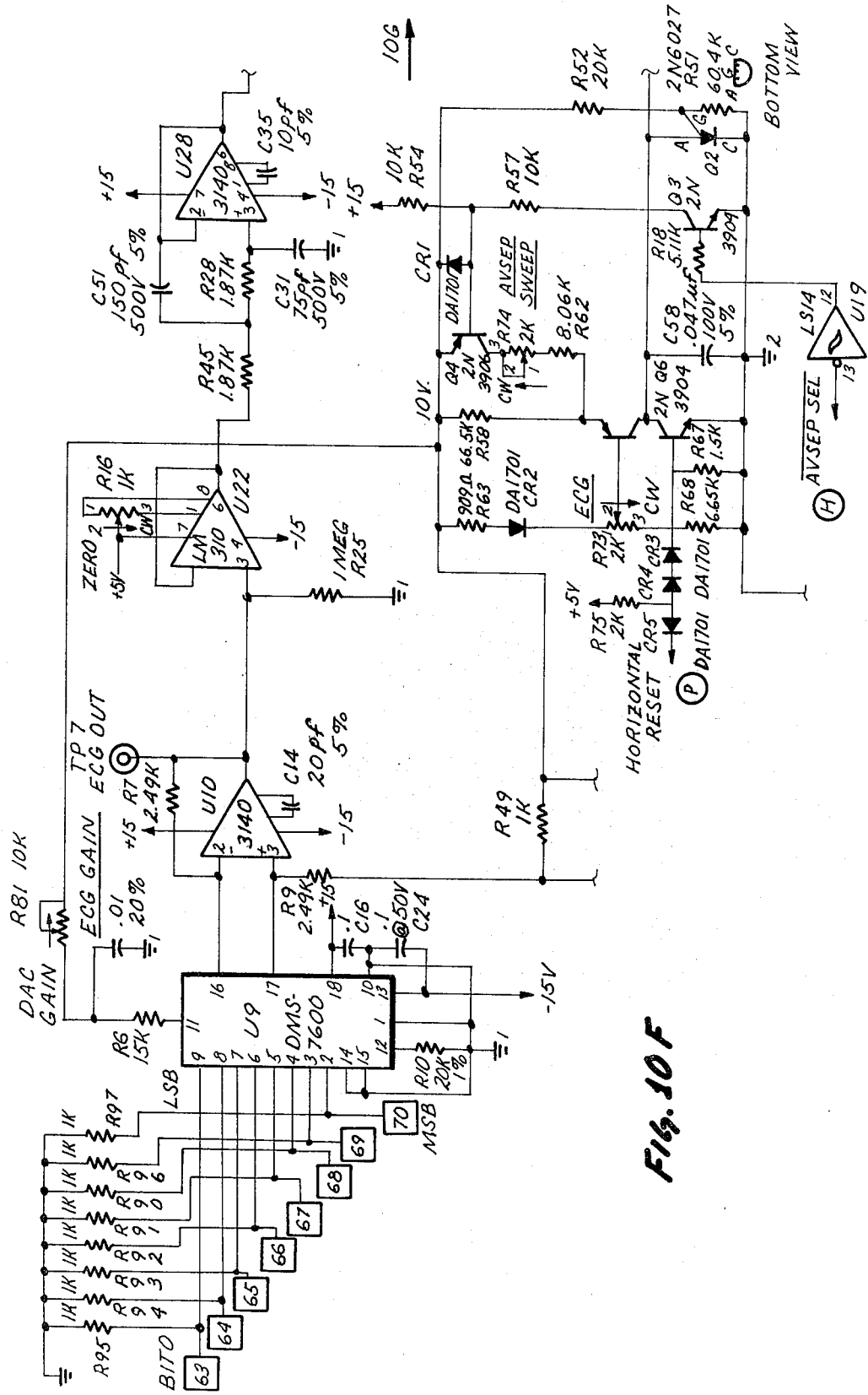
Figure 106:
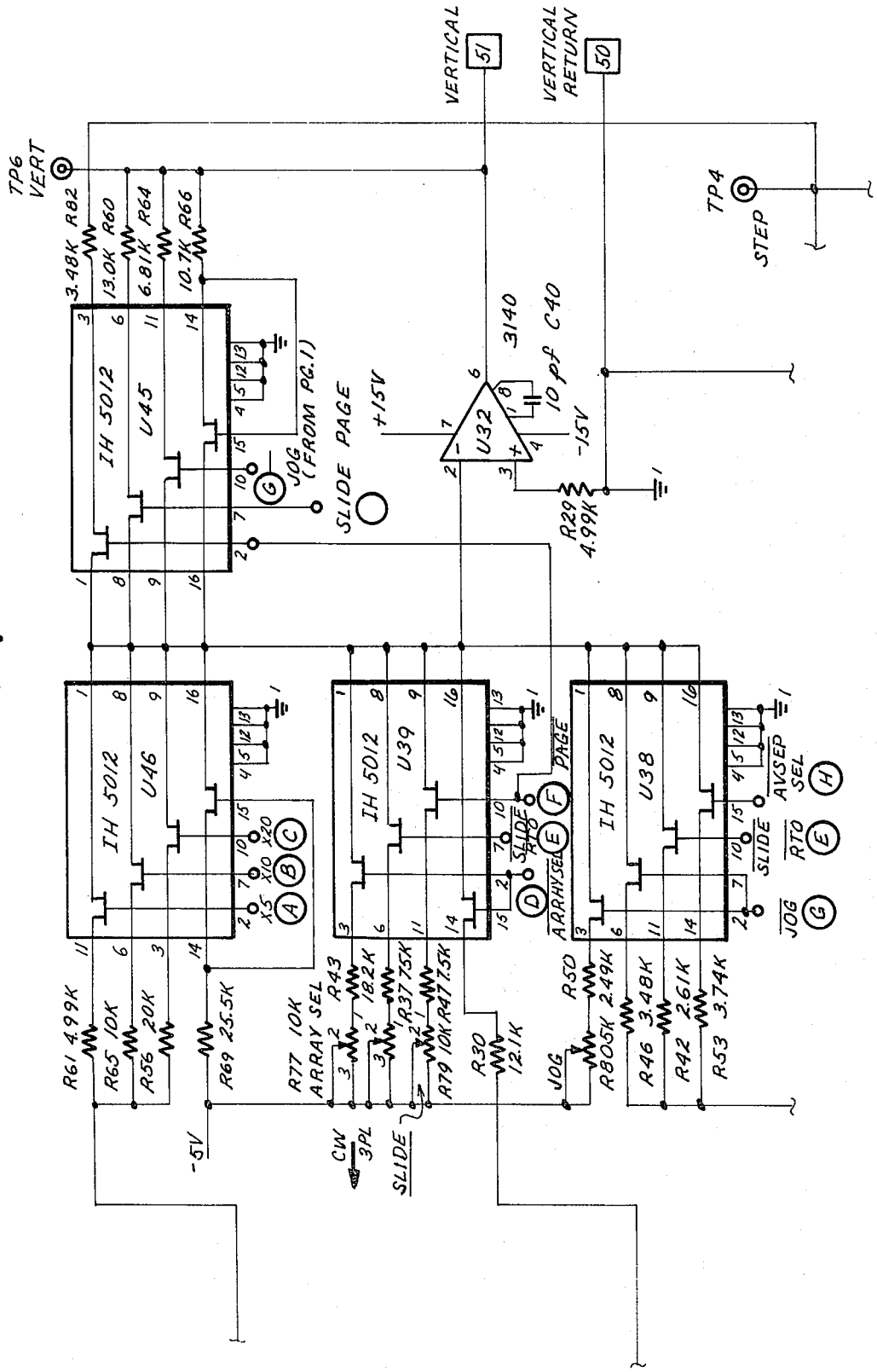
Figure 10H:
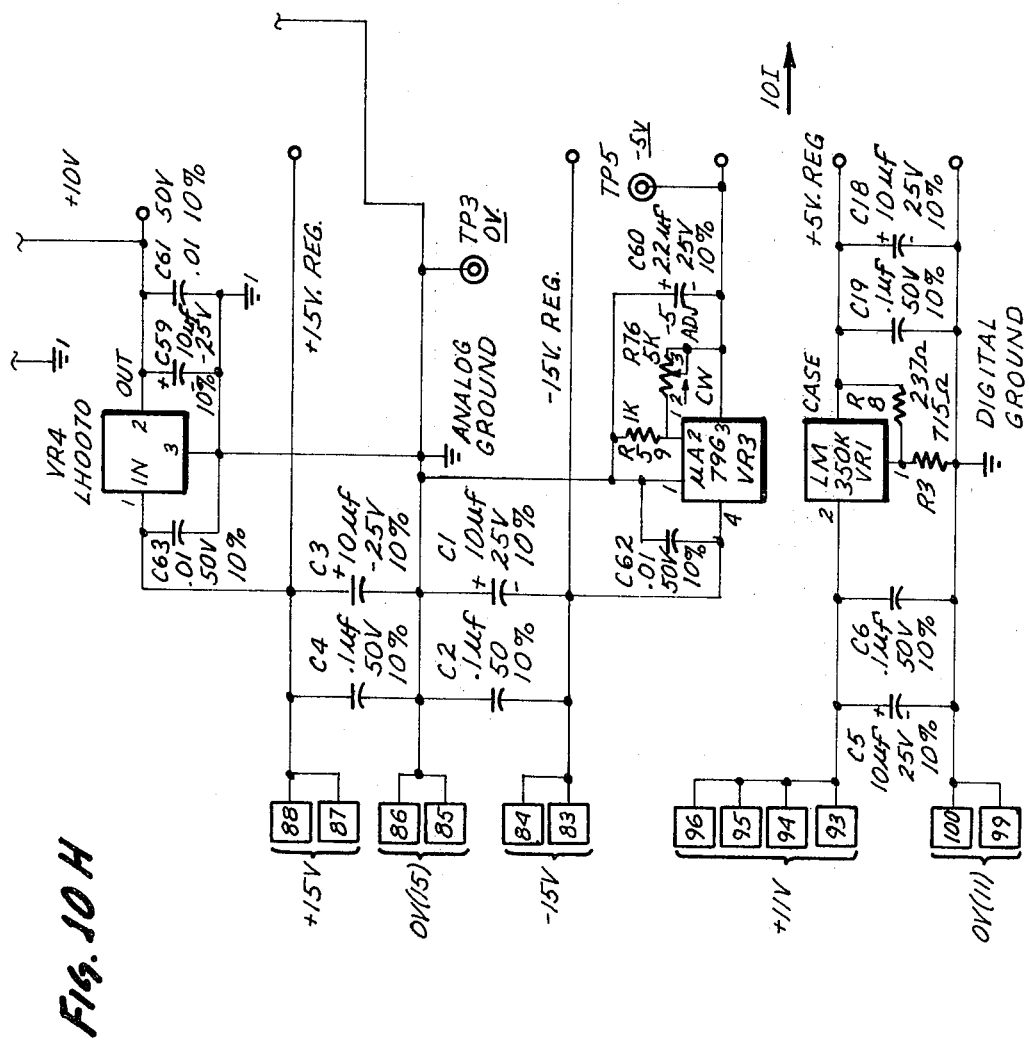
Figure 10I:
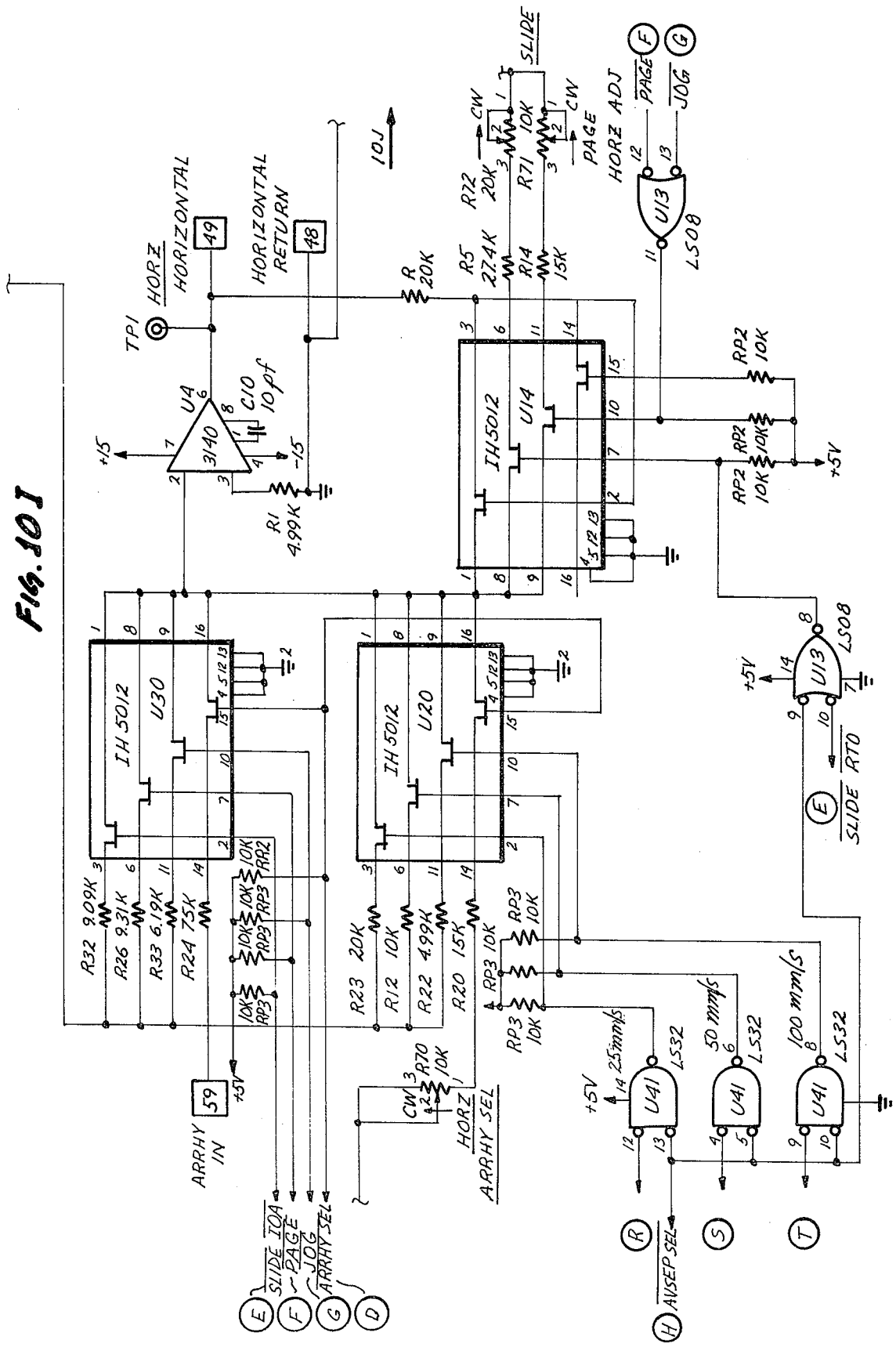
Figure 11:
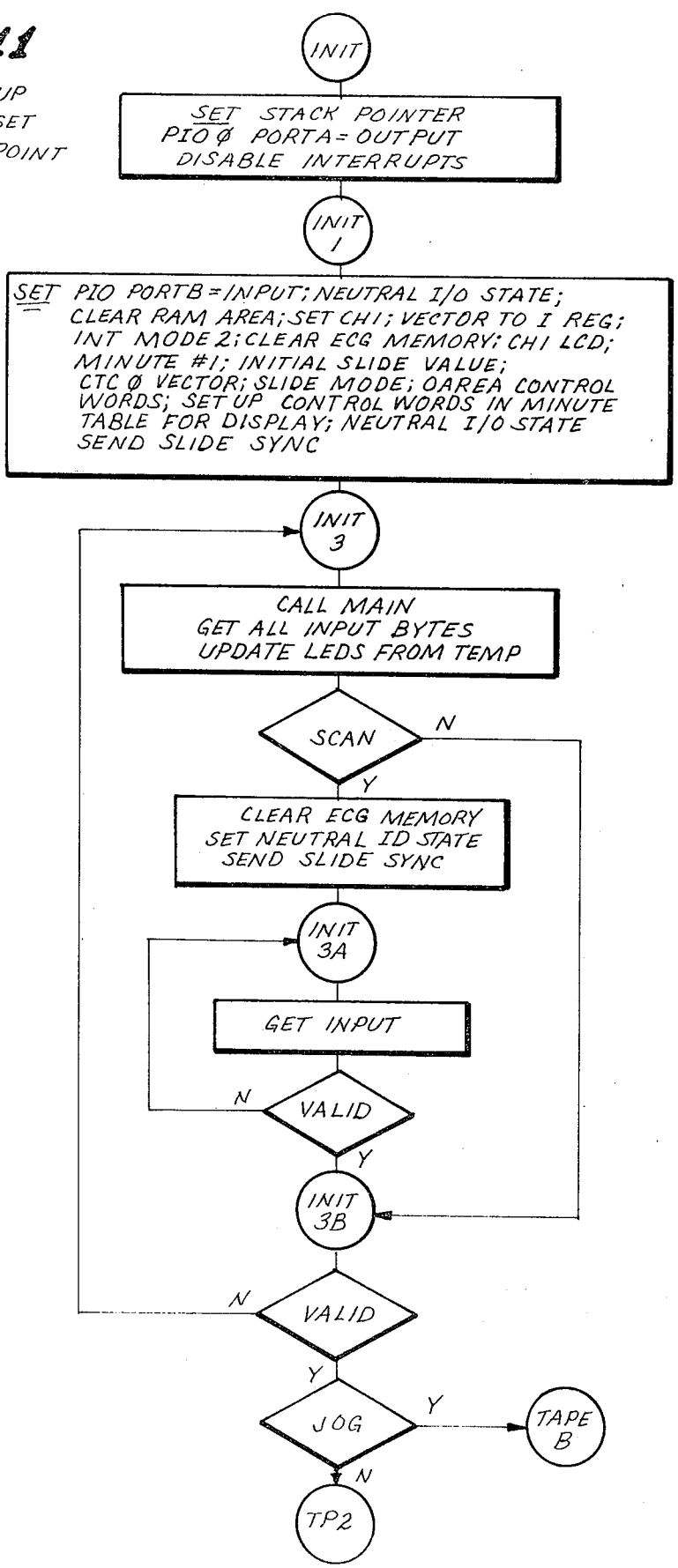
FIG. 11 is a logic flow diagram of the power-up cycle of the present invention.
Figure 12:
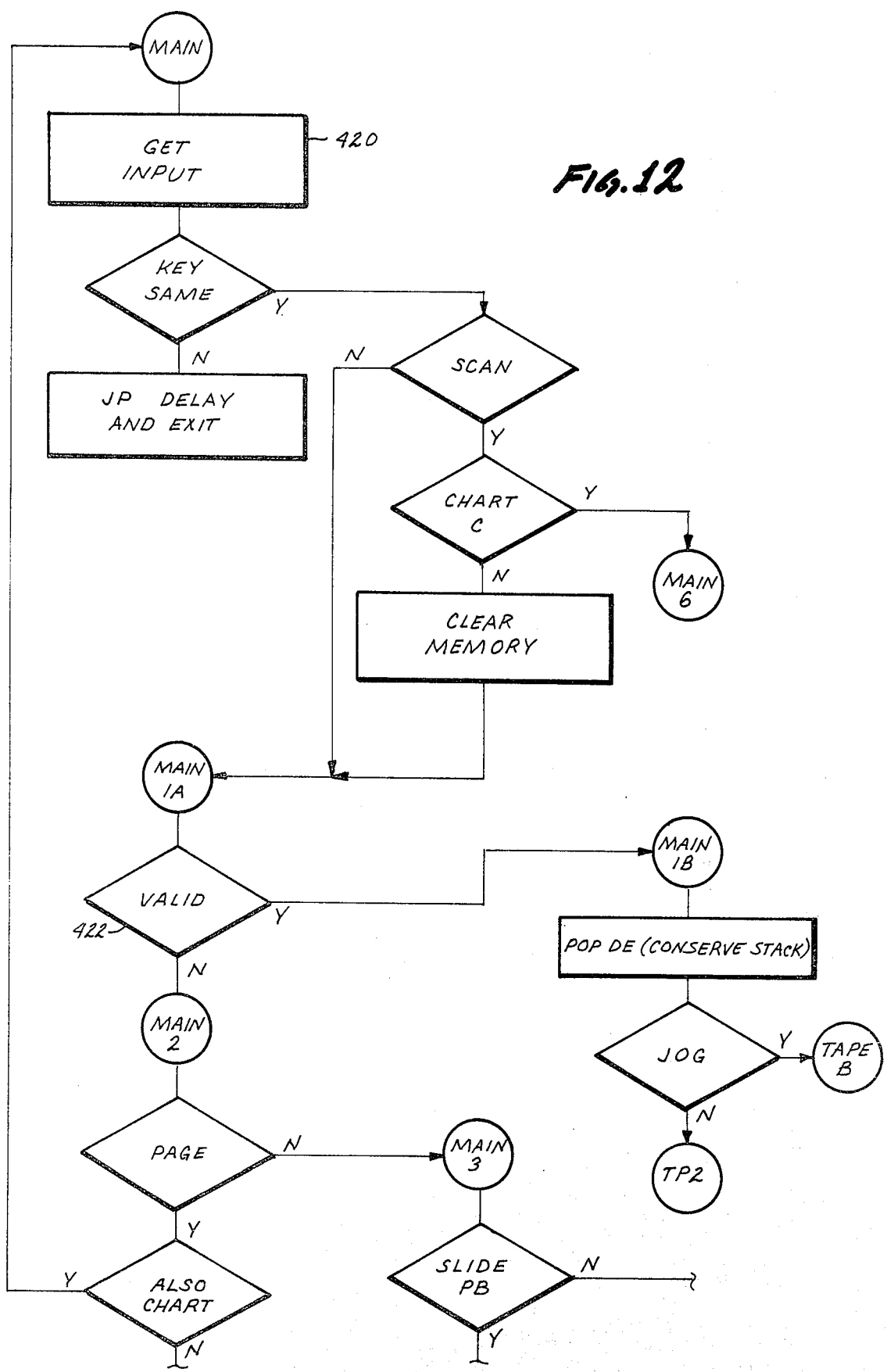
FIGS. 12, and 12A-12C is a logic flow diagram of the main computer subroutine of the present invention.
Figure 12:
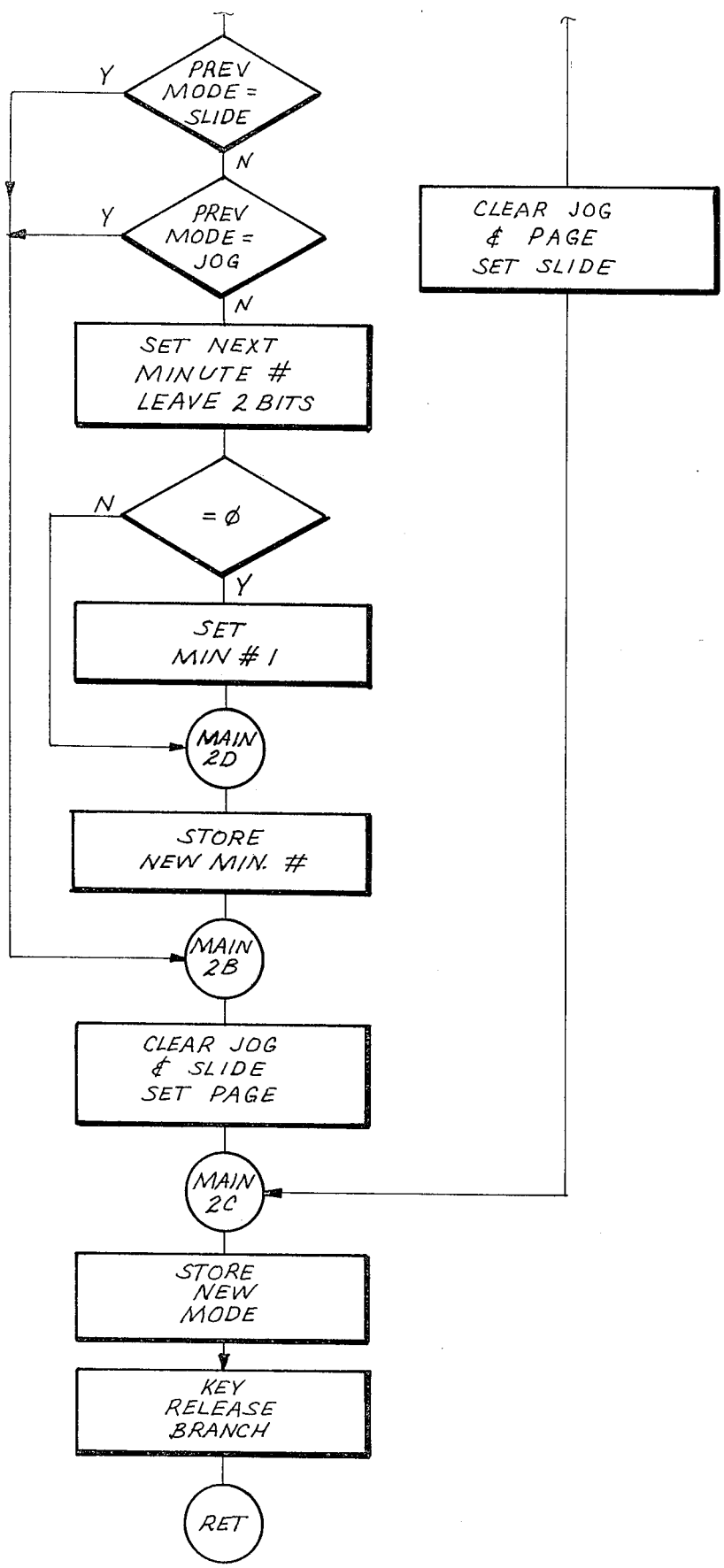
Figure 12A:
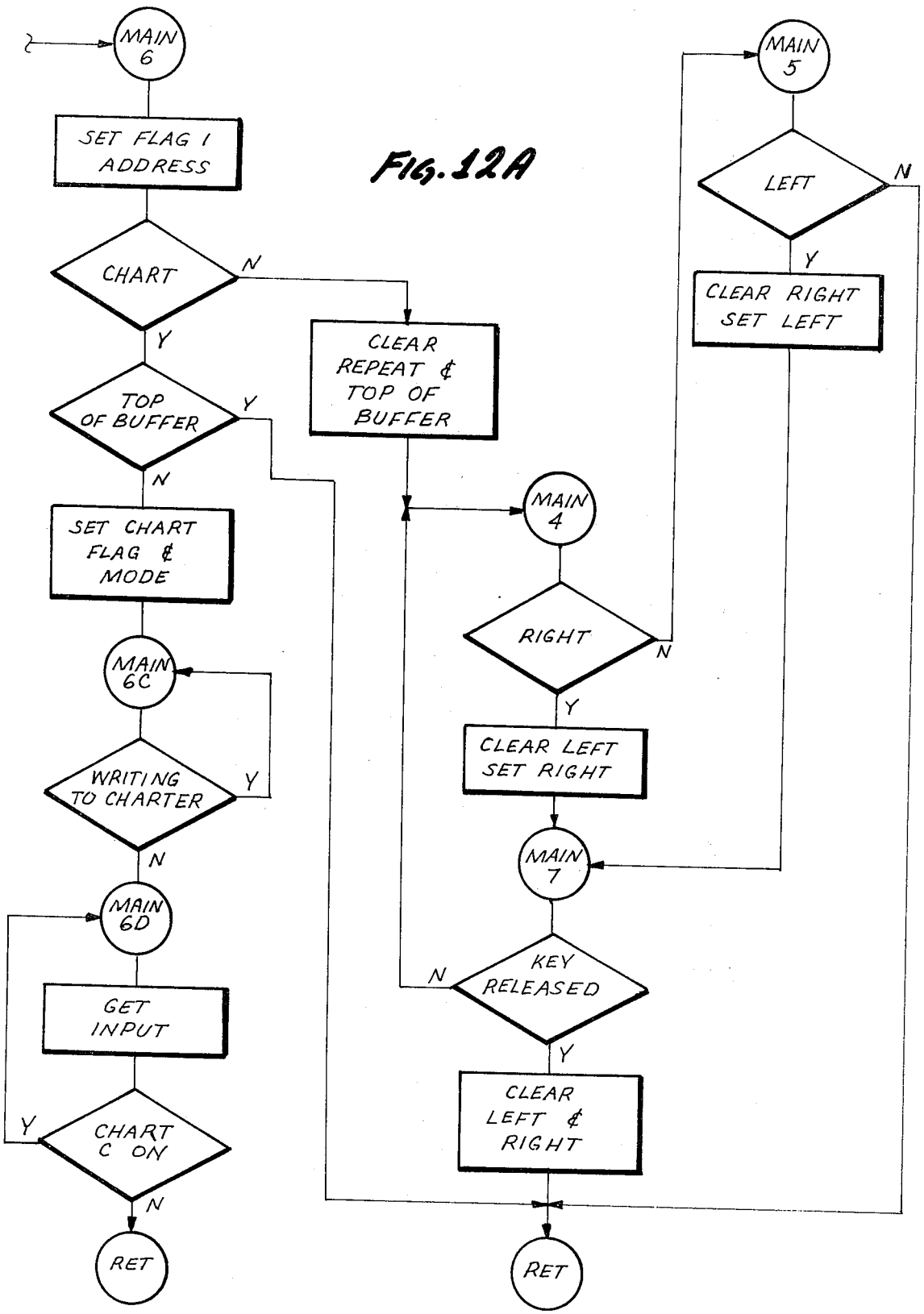
Figure 12B:
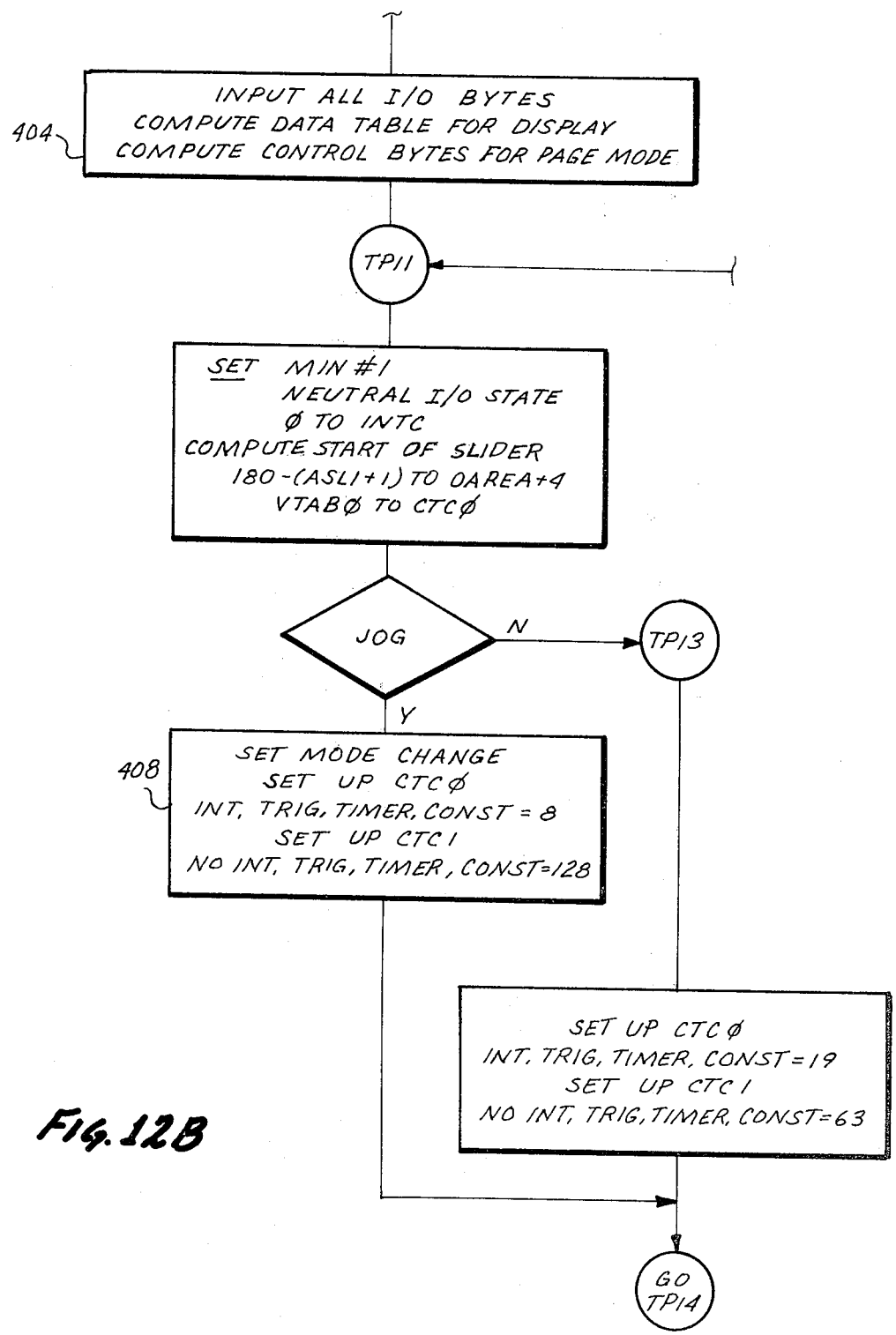
Figure 12C:
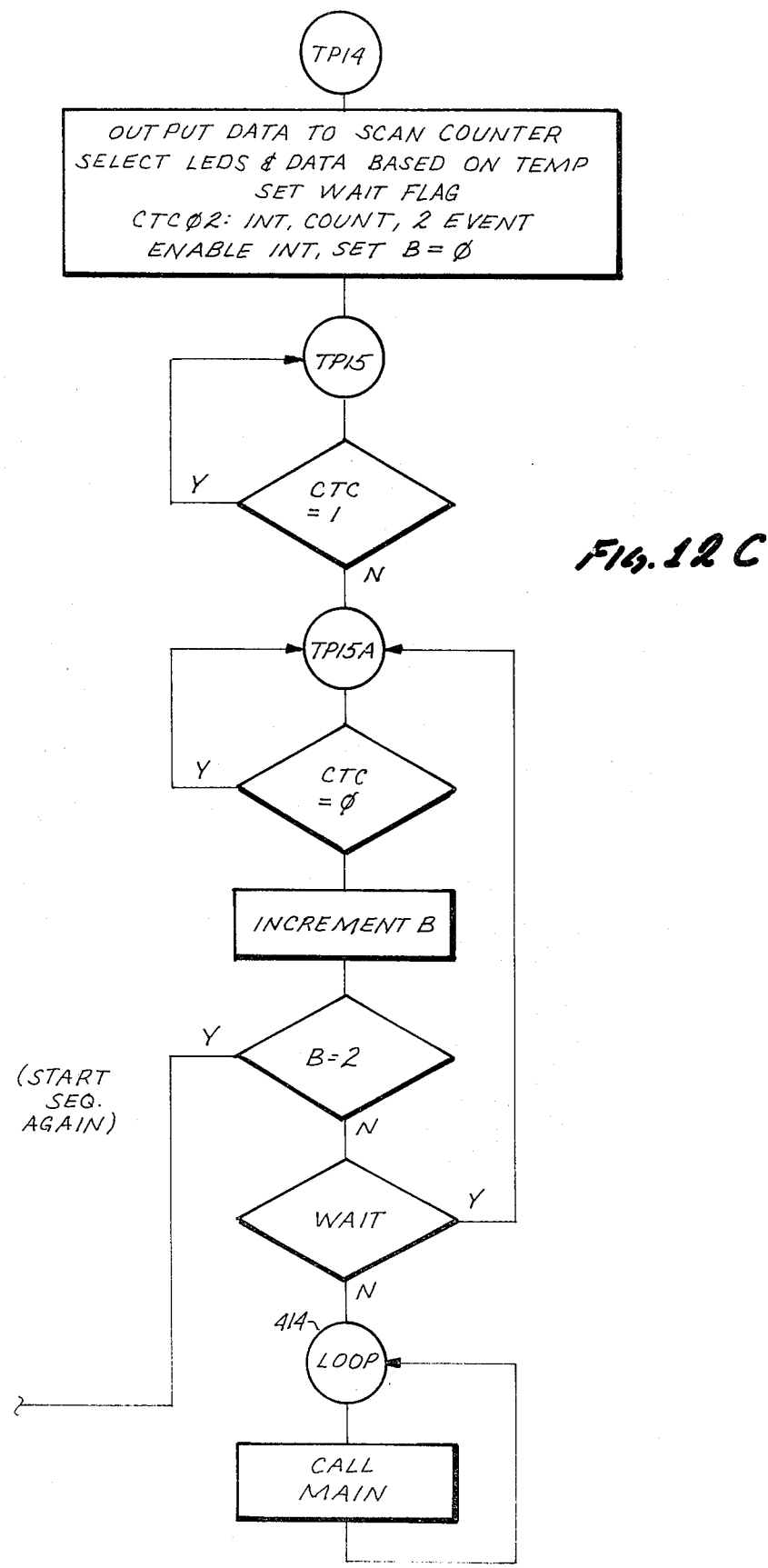
Figure 13:
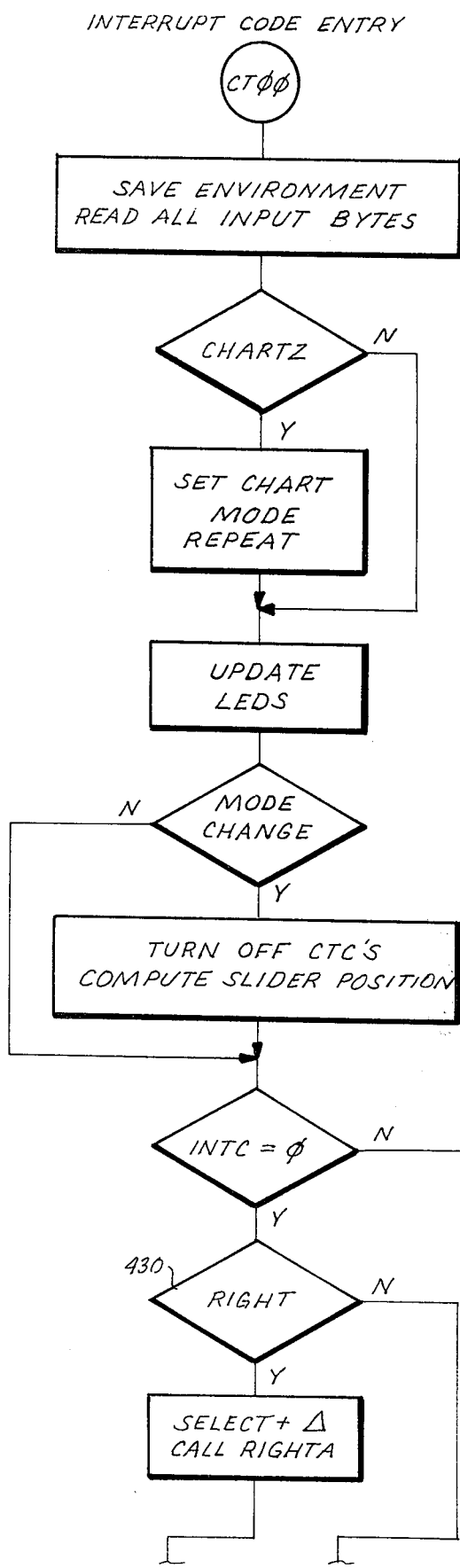
FIG. 13 is a logic flow diagram of the interrupt code used upon stop command signal entry.
Figure 13:
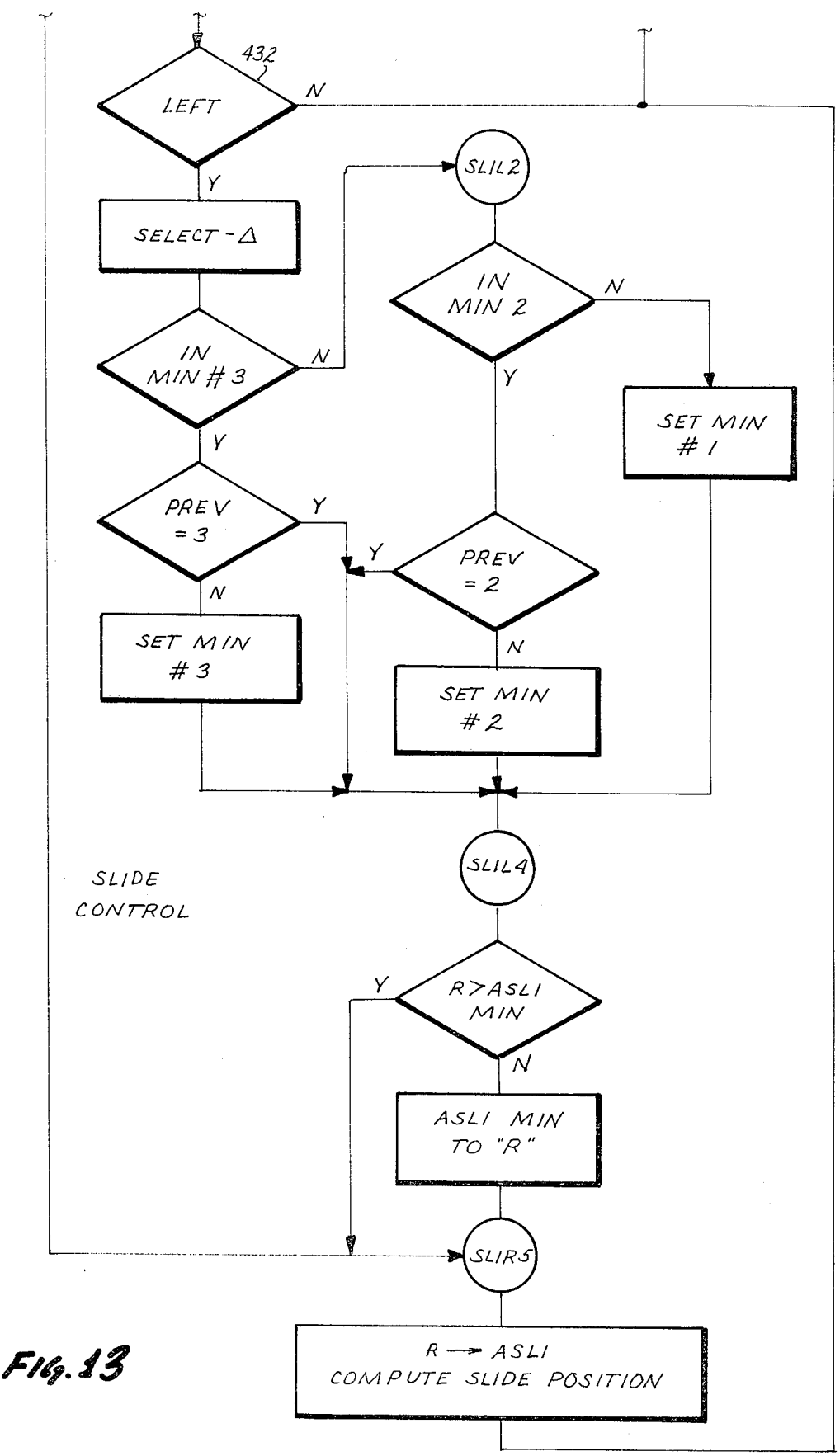
Figure 14:
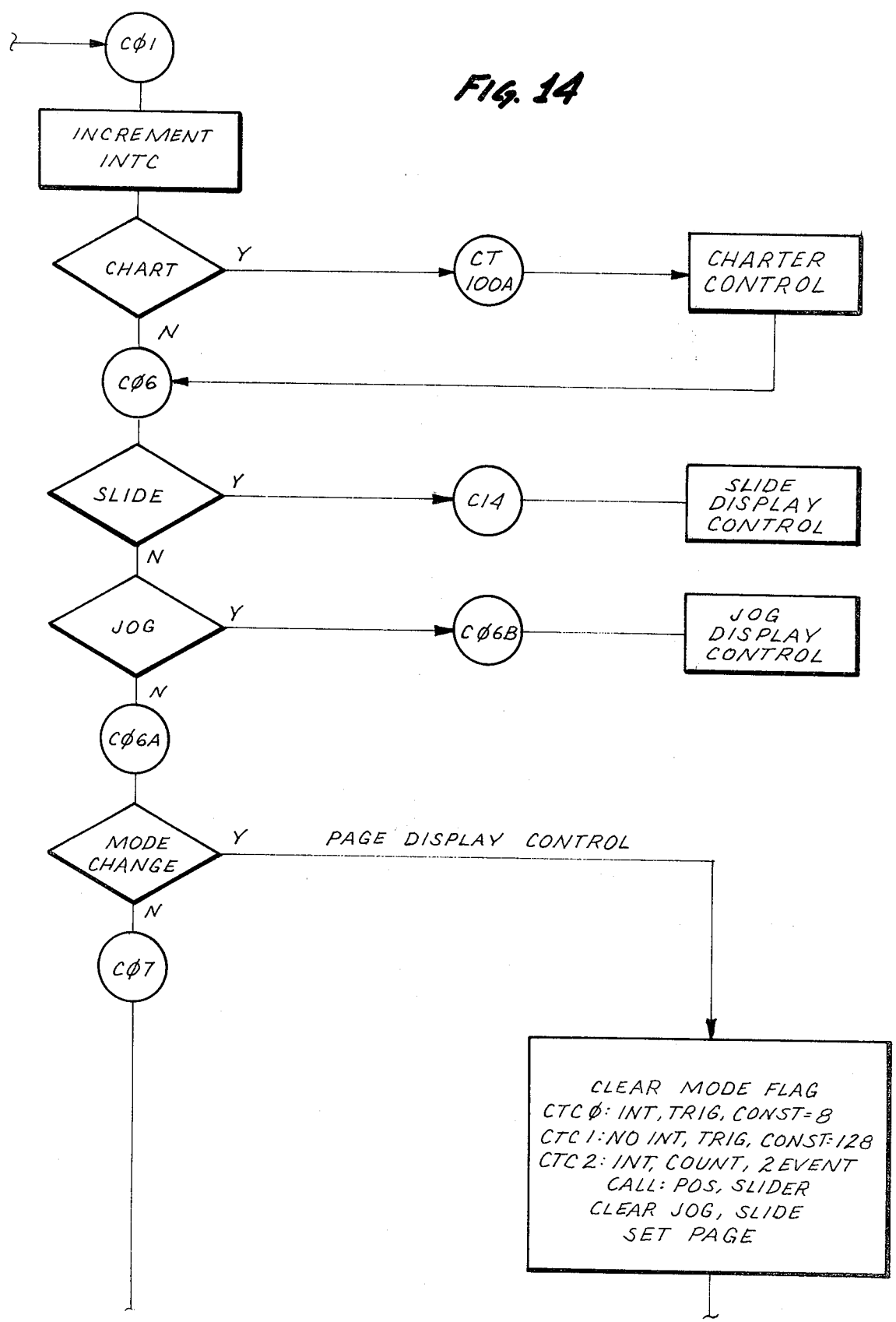
FIG. 14 is a continuation of the interrupt code entry logic flow diagram of FIG. 13 as employed for PAGE display control and also illustrates PAGE interrupt timing.
Figure 14:
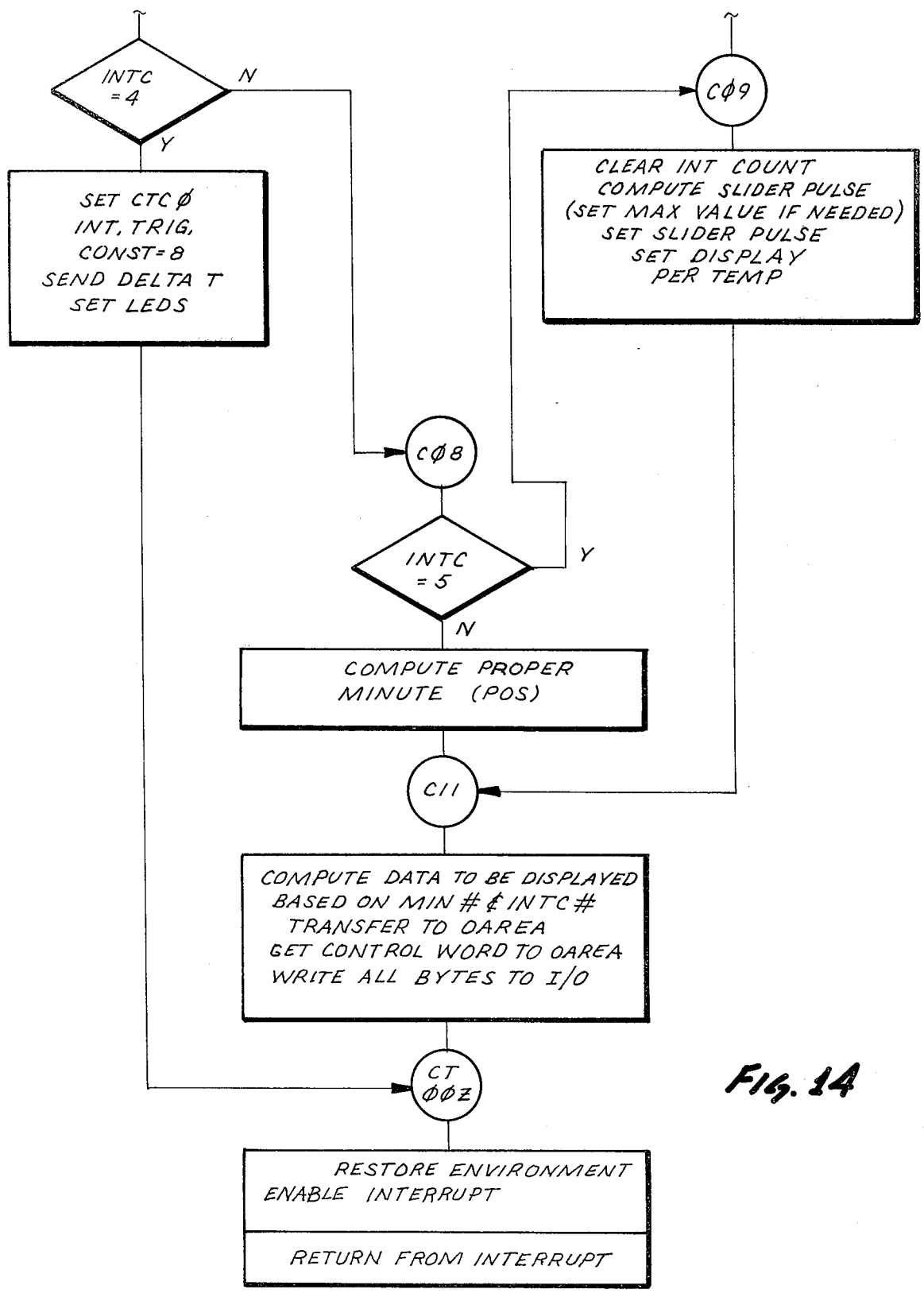
Figure 15:
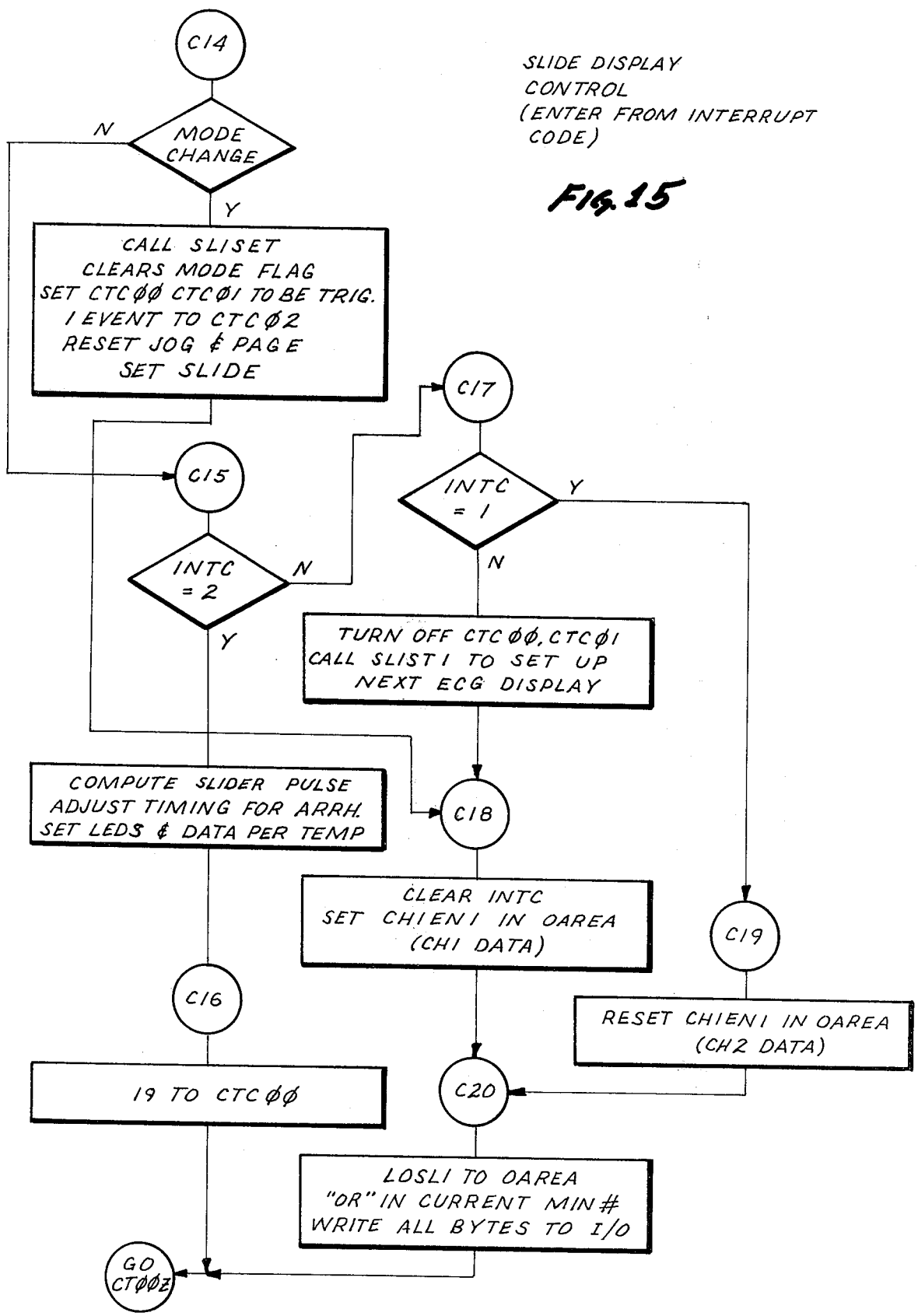
FIG. 15 is a logic flow diagram of a continuation of the interrupt code for SLIDE display control.

Referring now to FIGS. 9 and 10, display timing depends on the display mode and is set up by the CPU in response to keyboard 42 inputs. A complete frame of data is displayed on the CRT screen 60 times each second for JOG and PAGE modes and a slightly higher rate for the SLIDE mode.

After receiving a keyboard command, Channels 0 and 1 of U5 are set up with specific constants for the particular display mode selected. Channel 2 is set up to trigger on external events at U5-21 (SMEM), and 2 events are required before a trigger pulse is issued by Channel 2 at U5-9. The output pulse at Channel 2 starts the timing action of Channels 0 and 1 and a new constant is written into Channel 0 for the next timing cycle. The outputs of Channels 0 and 1 are conditioned by U21 to become the vertical and horizontal sweep sync pulses, and U21-6 also serves as the memory address load pulse. Each time-out of Channel 0 is also an interrupt to the CPU, and it is during the service routine that the next start address of data to be displayed is loaded into U24 and U37. In this fashion, the CPU action is transparent, since the data setup occurs a step ahead of when it is used.

For JOB and PAGE display modes, the trigger is required only once when these modes are entered and then the timing is locked to the system clock; however, in SLIDE mode, each frame of data is triggered by SMEM resulting in a frame rate slightly more than 60 Hz.

Page Timing

Clock input to the CPU and CTC's is at 1.966080 MHz (system clock) and CRT timing is derived from this frequency. At a display rate of 60 Hz, one complete frame of display occurs in 32,768 system clocks (16⅔ msec). The following computations define the required CTC constants for PAGE mode display, which must show 4 traces of 15 seconds each on the screen.

Since the data output rate from memory is at 983.040 KHz, there are two system clocks per data sample. Fifteen (15) seconds of data corresponds to 3840 data samples in memory (15×256=3840), and it will take 7680 system clocks to display this data. Four such time periods are required to display one full minute of data from memory and the remaining time interval of 2048 system clocks forms the blank time between frames. The CTC timing function is prescaled by dividing the system clock by 256, which results in a CTC time constant of 30 (7680/256=30) as the time to display 15 seconds of data in one sweep, and a constant of 8 (2048/256=8) as the time constant required to define the blank interval between frames. This establishes timing for Channels 0 and 1 for the PAGE Mode, as shown, and this timing repeats once it is started by SMEM at a 60 Hz rate. The result is shown in the timing diagram of FIG. 22D.

The decoding of the two channels by U21 results in ECGSYN and ECGHOR, thus it is evident that ECGSYN corresponds to a vertical or frame sync while the positive edge of ECGHOR defines the start of sweep for each of the 4 traces which form the PAGE display and is the line sync.

JOG Timing

Constant computation for the JOG display is similar except that 6 traces are shown with each trace being equivalent to 30 seconds of stored data. See FIG. 22E.

At the transfer rate from memory (983 KHz), it is not possible to display the entire contents of the 3 minute buffer (49152) samples) at a 60 Hz rate. To overcome this, reference to the ECG CPU schematic will show that U1-6 is active in this display mode and has the function of gating in 2 extra clock pulses to the ECG Memory Address Counter which results in a complete scan of the 3 minute memory in the allotted time but produces a lower resolution display due to the time constraints. Thus, the display contains 16384 samples for 3 minutes of data, whereas the same number of samples is shown for only 1 minute in PAGE mode.

Slide Timing

Constant computation for the SLIDE display is similar except that it is necessary to display 11 seconds of data for each of the two channels at a rate slightly higher than 60 Hz in sync with SMEM. See FIG. 20F.

Cursor

The position of the SLIDER (11 seconds of data) in the 3 minute memory is updated and computed in time interval "A" of each frame of data. The computed position is scaled approximately for a specific display mode and then the computed start and stop times are outputted to Channels 0 and 1, respectively, in U12. The intensified region of ECG data, on the screen, is that portion of the 3 minute memory which will be displayed in SLIDE or output to the Charter if either of these is selected.

In PAGE and JOG modes, these two channels (U12) are triggered into operation simultaneously by the positive-going edge of ECGSYN (beginning of data display time). Initially, U13-3 is inactive due to the setup of U1 by end of frame pulse produced at U5-8 (Channel 1 of CTC0). As soon as CTC1 channel 0 times out, a pulse is produced at U12-7 which causes U1-6 to go high and causes U13-3 to become active. Channel 2 (U12-8) times out a short time later and the output causes U1-11 to go low causing the output at U13-3 to become inactive and, thus, terminates the slider intensification pulse. The positive-going edge of this pulse is detected using D Flip-Flops U20 and U26 to produce a reset pulse to CTC1 which terminates further channel activity. Channel reset in hardware is necessary because, once channel activity has been initiated, the channels continue to operate repeatedly with the same time constants and this could produce multiple intensification regions within one frame of data.

The display position of the SLIDER in SLIDE mode is computed and produced in the same manner except that the channels which generate the pulse are triggered into operation by the negative-going edge of ECGSYN. The same edge triggers the start of the Arrhythmia Display and, as a result, the equivalent of 11 of the total 180 seconds of this presentation is intensified rather than a portion of the ECG data. The intensified area also indicates the relative position of the currently displayed ECG data in the 3 minute buffer.

The CPU monitors status and asserts control of the hardware through PIO Ø (U52) and the 74LS 138 multiplexers (U16, U23). At power-up and after a CPU reset, U52 is set up so that Port B is used for data input and Port A for output purposes. Each latch on the input is selected using U16 and the CPU address lines A8, A9, A10. Bits A8 through A10 at U16 form the binary code to select a specific input word, and A11 (together with IORQ), become the chip enable (to U16) which gate out one of the input selects. The specific latch which receives an enable applies its data to the input port (B) of U52 to be read by the CPU in the same memory cycle. IORQ is used as one of the enables at U16 and U23 to eliminate spurious selects being issued in response to the bit patterns on address lines A8 through A11. In this application, A11 is used as a READ/WRITE select. When A11 is low, it enables one of the input latches while the output selects are all disabled, and the reverse is true when A11 is high. In addition, A11 enables ASTB and BSTB at U52 with the required levels for data transfers without the need for synchronizing strobes.

Output transfers are handled in the same fashion, except that A11 must be high to enable one of the latches in an output cycle. In addition, A6 and A7 must be low indicating that this data output is not occurring to one of the CTC's (U5, U15). When either one of the CTC's is enabled for an output cycle, this automatically inhibits selecting an output latch at the same time.

Data input from latches takes place in the sequence which follows:

An address is asserted on the CPU address bus with the positive edge of the system clock in the T1 state (see Mostek Data Book). Multiplexer U16 decodes the address lines, but no select is issued because the chip enable IORQ is not yet active. Enabling the chip output with IORQ produces glitch-free input selects.

IORQ is asserted at the positive edge of the T2 state and enables one of the input latches, which then applies data to the bus connected to Port B of U52.

After data has settled on the bus, it is read into the CPU at the falling edge of T3 (2½ system clock cycles after IORQ was asserted). The falling edge of T3 also causes IORQ to become inactive, which disables the input select and the selected input returns to a high impedance state.

Data output from the CPU takes place in the sequence which follows:

An address is asserted by the CPU exactly as in the preceding Step "a" except that the decoding is done by U23 for an output select.

Data to be output by the CPU is asserted on the data bus at the falling edge of the T1 state.

IORQ is asserted at the positive edge of T2 enabling the output from U23 to select one of the output latches which then receives the data issued by the CPU.

After the data has settled, the falling edge of T3 causes IORQ to go to the inactive state which disables the output select to one of the chips and causes the data on the bus to be latched in the selected output.

Flow Diagram

Reference is now made to FIGS. 11-16 of which shows the power up cycle flow diagram.

When the Power up occurs the CPU initializes an assortment of functions. After power up has gone through its initializing code and the operator has selected either a tape scan or a tape JOG, there will be a branch mode to one of the two points in the program either TP2 or Tape B. This branches to one of the two entry points which will then being processing the tape load, in one case entering through TP2. There is an auxiliary memory clear cycle which occurs and does not occur during JOG entry for the reason that the JOG entry will load an adequate amount of data such that three minutes of data are loaded and it will overwrite all of the data that's in the memory whereas a TP2 entry by SCAN push button may not load a full 3 minutes of data and therefore a clear of the memory is an auxiliary cycle required to establish flat base lines. In either case, the TP2 point is entered where additional tests are made to see if the valid is still active, if it is issued to the output structure of the CPU to initiate the start of loading. The processor then waits at 402 until the tape load has been completed. The tape load in hardware freezes the action at the instant that the valid signal is turned off and then subsequent to that action the processor responds by reading all of the inputs and stores them and then computes the positions of the various data segments that are going to be needed to select portions of data for display purposes.

During this section of time where we're between TP3 and the valid off, the condition of the system is SCAN and during that condition the AVSEP and arrhythmia displays are on. Once a valid off signal either from the arrhythmia computer or from a stop signal initiated by keyboard command, ECG displays will be actuated, 402 designates looping during SCAN.

Step 404 looks at all input command bits to determine what mode is to be initiated in the following steps.

At the end of every tape SCAN the same conditions will apply and minute number 1 is always established so that the slider is in the most recent minute of data which was loaded into memory. The start position of the slider is computed and this is a number which is then computed for the memory and that establishes the minus 28 second before stop time location of the slider that addresses and is extracted every now and then during various displays and rescaled as necessary so that that number then determines the trace intensification area depending again on which display is being used. The scaling will be different. If the left and right PB were operated, then the number will change and the intensified area will move progressively. But initially it has a fixed position, a pre-established position immediately after the tape SCAN has been completed. The immediately following point is a test which is made on an internally stored flag and that flag is one which was set at the entry to Tape B or Tape 2 depending on which branch was used to enter the tape code. Then that same flag is tested and will establish what this play mode is going to presented on the screen at the time the tape code is exited. The reason for that is that the timing is different and, consequently, the CTC which is responsible for the display dync and timing has to be set up with different numbers.

Instructions box 408 and 410 establish the different timing sequence that is required for each of the displays. At PB 14 we continue with some tape related and set-up conditions while the two channels are going to time out. In PB 14, also, an additional CPC channel has some timing initiated in it and then when that particular channel times out then the ones that have been set up in Steps 408 and 410 are triggered into operation so that they are synchronized and operate starting at the same instant. The additional tests of the PB16 are safeties to insure that exits from the tape code are proper and assuming that there was some hardware failure then this code protects against getting trapped in an incident loop at this particular point. Eventually the code would get to a step labelled LOOP 414 and then there would be a call to the main contral loop and the main control loop interrogates the inputs and collects operator input data from keyboard and external inputs monitors. The loop can be exited from—main can be exited and then jumped back into TP2 or Tape B on the same sheet and then responds to a SCAN or a JOG operator action and then begins a new tape load which will require repetition of the same sequence just described.

In 0, in 1, in 2 and In 3 determine the current state of operator responses as needed. That would be how the keyboard primarily functions because unless a new tape SCAN was started In 2 and In 3 would not need to be interrogated since it would only be used for reading the exact address at which memory loading ended. After checking for debounce, then a sequence of tests is made to find out which particular botton has been pressed. If the SCAN button has been pressed, then we would enter into a special sequence and go back to another tape load. If a SCAN has not been pressed, the program proceeds through to Main 1a, where a check for tape motion is made to see if it had been started through a different form (such as JOG). If valid is not active (i.e. no tape response), the procedure skips the branch at Main 1B and continues at Main 2. There the test is made to see if the operator had pressed the page button and if not, one continues with Main 3. If the operator had pressed the page button one falls through and makes the additional checks as needed through the code showing below the page pushbutton. If the operator had not pressed the page button, one makes the next test which would be the slide pushbutton and, assuming that it was pressed, one performs a certain group of functions, whereas if it were not pressed one skips over to Main 6 and make tests on other auxiliary functions. In all regards this is the flow which would be testing for operator input at—let us say at Main 6 we are not in a charting cycle but one ignores that input line and then goes to Main 4 where one tests for the left and right pushbuttons. The left and right pushbutton when they become active a flag is set and the flag indicates in another portion of the control program that an increment is supposed to be added to the current position of the slider and the increment added to the number stored in memory would then have shifted position by a small amount, and therefore, the intensified portion in the diplay would have shifted a small amount either to the left or right depending on the action of the left or right pushbuttons in Main 4 or Main 5. If neither button is pushed this would be the end of the keyboard interrogation sequence. The routine would return and it would return back to the loop which is Block 414, and then the call to Main would repeat, going through the entire interrogation sequence, again all of the input buttons.

At the time that the tape code was exited the Step 408 and 410 set up some interrupt timing, which will then interrupt the operation of the main loop at exactly the uniform and timed intervals and then for each of these interrupt pulses specific action results and an entry is made to the interrupt code which is CTC CT00 code on Sheet 2 of 5 of flow diagrams. It is here that the data set up and the sequence of operations is performed to respond to the data that has been collected by the main loop, the main code. Initially, one enters the CT00 code and make some tests to verify some charting action is to occur. If it is not, LED's are updated. A test is made whether or not there has been a mode change. Each time one of the buttons is pressed, such as a PAGE button, or a SLIDE button, there is a change in the mode of operation in which case the current display mode, whatever it was, has to be terminated. Therefore, the timing, the interrupt timing, which was established at the last instant at the tape load up operation, has to be suspended; and then a new mode established. If there is no mode change, then this block is skipped and the test is made to see whether or not it is interrupt, the interrupt number which has resulted in entry into the interrupt code, is interrupt zero. If it is, then it is at this particular time that the left and the right flag, not pushbuttons—but left and right flag—are interrogated. Assuming that a left or right push button was pressed in the main code, then a flag would have been set and it is this particular flag which is tested in the interrupt code at this interrupt time ... at steps 430 and 432.

Assuming that either the left or right flag was set in the main collecting loop, then in Block 430 or 432 the condition would be responded to and an increment would be added or subtracted from the current position of the slider position address value; and then the new position would then establish, the new number would then establish the exact position in the current display of the intensified trace.

Assuming that neither the left or right button was pushed, a branch would be made of C01 where the interrupt number, whatever it was, would be incremented to the next value. A test is made whether or not a charting is required. A charting would have been another flag set in the main loop indicating that charting is necessary. However, if charting is not necessary, the flag would be cleared and therefore the code would fall to CO6, where the SLIDE flag would be tested and if it was slide mode a branch would occur; whereas if it was JOG, if it was not slide, then a test would be made of the JOG flag; and it if was neither SLIDE nor JOG, by default, it would get through to C06, where the page handling, page display code begins. If the mode change flag had been set, as a result of any button pushes, then the CTCs would then be established. The mode change flag set indicates that the previous display mode was being terminated and a new display mode was required to be set up. Therefore, the mode flag would be cleared in the new block and the CTC channels would be set up for the appropriate timing required by the page display sequence. That timing sequence is diagrammatically represented at the bottom of the page in a 16⅔ millisecond time frame. If there was no mode change, that block would be skipped and a continuation would be made at C07, to then a test of the interrupt number would be made, and if it was 4, then specific events would take place, such as setting the short time interval, which corresponds to the dead time where no data is being displayed. If it wasn't interrupt 4, then a test would be made to see if it was interrupt 5, and this would establish the specific timing constants to be issued to the CTCs which would be involved in display of data. In both cases, C11 would be reached, where data, there has to be some supplementary processing done to determine what the current minute number is, and then select the appropriate set of addresses from the scratch pad area so that they can be presented to the memory address counter at the appropriate times to extract the selected segments for the specified minute and then only that data appears on the screen. The required addresses and bit configuration is written into the I/O structure and then transferred into the counter at the right time so that it can be used by the hardware to present the appropriate segment for display. The exit from the interrupt code restores the previous environment. This is necessary because there if no telling when an interrupt actually must have occurred sometime during the execution of the main loop, but its unpredictable when that would occur. Subsequent interrupts have to be enabled and then the exit is made from the interrupt and a return back to some portion of the main loop would be made until the next interrupt occurred, at which time, entry would again be at CT00, and the new state of the system would be tested in a similar fashion to determine whether or not any new change in operation was necessary, depending on which branches were taken, and that depends directly on which flags are set in response to operator push button pressing.

SLIDE and JOG can now be discussed. Assuming that C06, the predominant display mode was other than SLIDE, and it is now SLIDE mode, we would take a branch to C14. C14 is on sheet 3 of 5, and again, assuming that the prior mode was not SLIDE, the mode flag would be set, and therefore the timing for the SLIDE mode would have to be established and the timing frame is shown immediately below the flow diagram. If the mode flag was not set, indicating that the prior interval was already in the SLIDE display, then a branch would take to C15, where since there are only 3 segments to be accounted for, in the sequencing and control of the SLIDE display, a test would be made to see whether the interrupt count was 2, and if it was, then a time interval for the arrhythmia display would be established, if the interrupt count was not 2, then C17 would be reached, where a test would be made for whether or not the current interrupt count was 1. This sequencing would do no more than establish the appropriate channel display, because at interrupt 1, we have to be displaying channel 1, whereas at interrupt 2, we have to set up the conditions to display channel 2 data; and alternate between the two. In one case a branch would be taken through C18; in the other case, a branch would be taken through C19, alternating between the two would be channel 1, channel 2 data, the processor in this case is only setting up the conditions, and then the hardware actually does the final transfers synchronized to hardware timing pulses, and those are the ones that are generated by the CTCs-CTC0, channels 1 and 2, that produce the sync. They're the ones that are also involved in doing some date transfers and also, toggling logic that then selects between channel 1 and 2 in this display mode. In C20, the slider position value would be issued to the output area. That particular value would also be issued at every interrupt entry and exit between every interrupt entry and exit, and that would then establish the relative position of the slider with respect to the stop time because the slider can assume any position from stop time to 3 minutes before stop time. Regardless of the branches taken, the exit is to CT00Z and that is the same exit point used by the PAGE code, which restores the current environment since this interrupt must have also occurred sometime during the execution of the main loop code, and then after enabling interrupts, a return is made back to whatever point was interrupted in the main loop. In the handling of the JOG code, a similar sequence of operation occurs. The new sequence of timings given for JOG display mode. There are 6 segments of display. In general, the sequences are pretty much identical to page except that slightly different numbers are being tested for because there are 6 segments in the JOG mode, whereas there are only 4 segments in the page mode. But the flow is essentially the same. In any case, if there is a mode change at the entry to the JOG code C06P, there is a test made, and if the prior mode was not jog, then the mode change flag is set and it will then fall through the block which establishes the appropriate timing as shown at the bottom of the page for the JOG mode. If there is no mode change, a test is made whether or not new timing intervals have to be written into the CTCs which control the display sync. and if not, if it is, a branch is made at interrupt 6 to establish a count of 8 in the CTC, whereas if it's not interrupt 6, but a branch is taken to C6B.

Referring to FIG. 18, two channels, channel 1, channel 2 of AVSEP are shown in which data from AVSEP memories have been recalled and superimposed on each other the trigger signal being derived from the R-Wave detector and offset by the amount indicated at 230. As indicated at 232 of the figures, the several complexes are reset by sawtooth signal 234. The present signal is constantly updated and constantly repeated during scan. Complex 236 appears wide in scan channel 1 while the arrhythmia complex 238 (being less frequent) is lighter. The arrythmiagraph signal is shown in bar mode and is also progressively updated during the scan. 236*b* and 238*b* identify the corresponding signal segments for channel 2.

FIG. 19 is a peak mode graph displayed when counter 90 is bypassed through the peak/bar switch. The visual representation is quite different from the bar mode graph even though both display the same data. In peak mode the signal rides the top of the graph or signal, changing by increments at each R-R shift. This AVSEP display has been found entirely satisfactory when compared to previous displays even though based on a completely different data collection and handling procedure using digital signal processing and digital signal storage.

FIG. 20 shows the drive signals from the SLIDE display while FIG. 21 shows the display itself. Channel 1 and channel 2 ECG are scanned in stationary mode while stationary arrhythmiagraph is also given either in bar or peak mode. The display relates the time interval covered by FIGS. 21A and 21B to the arrhythmiagraph which is intensified in the region 260 by a Z axis pulse as shown (FIG. 20C). This is particularly effective as the arrhythmiagraph serves as a kind of note pad or map of the surrounding data field as stored in from which specific R-R interval shifts can be identified. Left or right PB contact causes the progressive memory address change and brings about a movement or sliding effect of the ECG trace across the screen and simultaneous sliding movement of the window 260 along the arrhythmiagraph. The present invention provides exact alignment of the trace with means 264, 266 such as the cursor for identifying and bringing the complex which caused the stop command into unambiguous registry with the cursor 264, 266.

FIG. 22 shows the drive signals for the PAGE display. FIG. 23 shows the display itself in which the cursor now appears as an enhanced Z axis intensified section. A left or right PB demand causes the cursor on the stationary ECG display to move instead of the ECG signal itself as in the slide mode. Repetitive actuation of the PAGE PB on the keyboard will cause the display to transfer all at once to the next adjacent page of memory.

FIG. 24 shows the JOG display and cursor. This is very similar to the PAGE display except that the signal is more compressed and the full 3 minute memory is displayed with the cursor relating the interval of interest back to the AVSEP, SLIDE and PAGE displays. Repetitive actuation of the JOG PB on the keyboard causes the tape to jog to the next adjacent 3 minute segment of tape or memory and to reload data into the ECG memories for the new 3 minute segment. Correlation to the original segment that initiated the stop command is then lost.

We claim:

1. A method in a display system for a high-speed viewing of extended ECG recordings on a CRT, comprising the steps of:

scanning the recording at a predetermined speed, writing a video ECG signal into an addressable memory, detecting the R wave of ECG events and forming a pulse train thereof, writing said R wave pulse train into an addressable memory, generating an R-to-R signal train, storing said R-to-R signal train into an addressable memory, reading and displaying intervals of said ECG video signal stored in said memory from addresses representing a few cycles of ECG signal, triggered by reading the corresponding R pulse train at a set of addresses offset sufficiently from said ECG interval such that each entire ECG complex is displayed in an AVSEP mode, continuously updating said memories as said recording is scanned while simultaneously reading and displaying an arrhythmiagraph corresponding to a larger segment of ECG signals based on said R-R signal memory.

2. The method of claim 1 further including the steps of:

stopping said step of scanning at a particular point of interest, reading and displaying said video ECG signal over an interval encompassing the addresses from a first location to a second location in said memories, triggered by an arbitrary time base reading and simultaneously displaying the arrhythmiagraph, enhancing the arrhythmiagraph display over a portion which corresponds to said interval of the ECG video signal displayed, shifting said interval forward or backward together with the enhanced portion of said arrhythmiagraph, said enhanced portion of said arrhythmiagraph being defined as a cursor window.

3. The method of claim 2 for a SLIDE display further including the step of forming a time stationary display of a larger interval of said ECG video signal and in which said larger interval is enhanced to distinguish it from adjacent intervals.

4. The method of claim 3 in which said step of enhancing comprises intensifying the Z axis of said display.

5. The method of claim 3 further including the step of moving the displayed time segment and corresponding cursor window in time to an interval of interest in said time stationary display.

6. The method of claim 2 or 3 further including the step of printing out as a hard copy ECG trace corresponding to said enhanced portion of said arrhythmiagraph.

7. A method for displaying ECG signals taken from a data recording thereof for detailed analysis by an electrocardiograph operator in which the operator or a arrhythmia analyzer switches the display from a time moving scan mode to a time stationary mode of a display over an interval of scanned ECG signals, comprising the steps of:
   converting the ECG signal to a ECG digital signal,
   storing at least a pre-determined interval of the ECG digital signal in an ECG memory, detecting the R-wave of said ECG signal and converting the same to an R wave digital signal,
   storing the R wave digital signal in an R wave memory for a pre-determined interval of said ECG signal,
   displaying a plurality of siad ECG digital signals seriatiam and superimposed over each other to form a visual portion of AVSEP display,
   forming an arrhythmiagraph from said R wave digital signal,
   displaying said ECG digital signal and said arrhythmiagraph repetitively on a single CRT scope for operator viewing at a rate higher than the flicker frequency,
   continuously updating said ECG, and R wave memories and arrhythmiagraph and displays of said ECG digital signals and arrhythmiagraph,
   switching to said time stationary display upon operator or machine command and displaying an interval of the stored ECG digital signal encompassing said pre-determined interval displayed in said scan mode, so as to encompass the immediately preceding scanned ECG digital signals,
   displaying said arrhythmiagraph encompassing said displayed ECG digital signal,
   enhancing the portion of the arrhythmiagraph to form a cursor window indicating the relation between said interval displayed in said time stationary mode and its corresponding location in said displayed arrhythmiagraph.

8. The method of displaying an ECG signal as in claim 7 further including the step of moving the time segments displayed in said time stationary mode together with the cursor.

9. A display system for high speed viewing of extended ECG recordings, comprising:
   means for scanning the recording at a pre-determined speed and for developing an ECG video signal therefrom,
   ECG memory,
   addrss means for writing said ECG video signal into said ECG memory, an R wave memory for detecting the R wave of ECG events on ECG recording and forming an R wave pulse train therefrom,
   address means for writing said R wave pulse train into said R wave memory,
   means for generating an R-to-R interval signal train for an arrhythmiagraph, each said R-to-R signal having an amplitude proportional to a selected measure of each corresponding ECG video signal,
   address means for writing said R-to-R signal train into an arrhythmiagraph memory,
   address counter means for reading intervals of ECG memory from the addresses representing a few cycles of ECG complexes triggered by recalling the corresponding R wave pulse train at addresses offset from said ECG addresses such that each successive complete ECG complex is displayed in AVSEP mode superimposed on each other,
   means for continuously updating each of said memories as said recording is scanned while simultaneously reading and displaying said arrhythmiagraph covering a larger segment of ECG signals based on said R-to-R signal train in said arrhythmiagraph memory.

10. The display system as in claim 9 further including:
   means for stopping said scan at a particular point of interest,
   means for reading and displaying said video ECG signal over an interval encompassing the addresses from first address to a second address in each of said memories against an arbitrary time base,
   means for reading and displaying the contents of said arrhythmiagraph memory against an arbitrary time base, said means being alternately and continually repeated at a rate to give the impression of a time steady continuous display to the operator,
   means for enhancing the display of said arrhythmiagraph over a portion which corresponds to that displayed in the ECG display,
   means for shifting the enhanced segment forward or backward in said ECG display together with the enhanced portion of said display.

11. The display system as in claim 9 comprising a single CRT having a single gun for displaying portions of the contents of each said ECG and arrhythmiagraph memories during high speed scan.

12. The display system as in claim 9 further including means for displaying a portion of the contents of said ECG memory of about four to twelve cycles in duration as an AVSEP superimposed display of successive ECG complexes.

13. The display system as in claim 9 further including:
   means for providing a SLIDE mode display of non-superimposed continuous ECG signals together with an arrhythmiagraph encompassing the interval of said ECG recording displayed and
   means for enhancing that portion of the arrhythmiagraph display which corresponds to said interval of said ECG recording displayed.

14. A multiple display system for the analysis of ECG signals from a recording thereof, comprising:
   means for scanning said recording at high speed and for generating video signals of successive ECG events therefrom,
   AVSEP memory means for storing an interval of ECG signals,
   R wave signal detector means for generating a sequence of R waves from said ECG signals, R wave memory means for storing said sequence of R wave pulses, means for continually updating said R wave memory and said AVSEP memory as said tape is scanned, read means for periodically reading said memories, said read means generating an address offset for developing a delay between data read from each of said memories, R-R memory means for storing said R-R pulse train, display control means for alternatively and successively displaying from said AVSEP and R-R memories: (i) an AVSEP trace of successive ECG complexes superimposed upon each other associated with an arrhythmiagraph of R-R intervals over a time segment larger than a scan cycle of said AVSEP trace; or (ii) a time stationary display of an interval of ECG signals encompassing the AVSEP display and an arrhythmiagraph of R-R intervals over a time segment larger than said AVSEP trace, and a cursor means for designating that portion of the arrhythmiagraph corresponding to the displayed ECG interval and said AVSEP trace during said time stationary display.

15. An AVSEP display system for ECG signals characterized by having an R wave taken from a recording thereof over a long time period comprising:

means for playing back said recording at a fast scan speed and for developing an ECG video signals, an analog to digital converter for converting said video signal into a digital ECG signal, a digital ECG memory for storing a predetermined interval of video signals, an R wave detector for detecting R waves and for generating a sequence of trigger pulses corresponding to said detected R waves, a trigger pulse memory for storing an interval of the trigger pulses, means for repeatedly replacing an interval of ECG video signals in said ECG memory with new ECG video signals as said recording is scanned, means for repeatedly placing an interval of the trigger pulses in said trigger pulse memory with new trigger pulses as said recording is scanned, means for generating a sawtooth ramp signal for each trigger pulse, said ramp signal to serve as the horizontal drive signal for a display, DAC means for converting the ECG digital signal into an analog ECG signal for display, first address counter means for addressing said ECG memory, second address counter means for addressing said R-wave memory, means for causing one of said first and second address counter means to be offset by a preload count, means for reading out said ECG memory as a Y signal axis and said trigger pulse memory as an X signal axis to create an AVSEP display and for reading out said trigger pulse memory against said sawtooth ramp signal to generate an ARRHYTHMIAGRAPH display signal, and single gun CRT means for displaying said AVSEP and an arrhythmiagraph at different locations above the flicker frequency to provide a continuously appearing simultaneous display thereof.

16. The display system as in claim 15 further including:

means for a time stationary mode of display including and ECG memory for each of one or more ECG channels, and a microcomputer for controlling the output from each memory, means for programming the microcomputer to compute stop and start addresses for each time stationary display corresponding to each ECG channel, for slide presentation, for Z axis intensification, and for printout.

17. The display system as in claim 16 including:

means for recomputing said start and stop addresses to allow a predetermined ECG interval to slide through said ECG memory and trigger pulse memory, means for displaying said arrhythmiagraph and for enhancing the portion of said arrhythmiagraph between said movable start and stop addresses of the interval corresponding to the start and stop times of said displayed ECG signals as the same is moving.

18. A method in a display system for a high-speed viewing of extended ECG recordings on a CRT, comprising the steps of:

scanning the recording at a predetermined speed, writing a video ECG signal into an addressable memory, detecting the R wave of ECG events and forming a pulse train thereof, writing said R wave pulse train into an addressable memory, reading and displaying intervals of said ECG video signal stored in said memory from addresses representing a few cycles of ECG signal, triggered by reading the corresponding R pulse train at a set of addresses offset sufficiently from said ECG interval such that each entire ECG complex is displayed in an AVSEP mode, continuously updating said memories as said recording is scanned.

19. The method of claim 18 further including the steps of:

stopping said step of scanning at a particular point of interest, reading and displaying said video ECG signal over an interval encompassing the addresses from a first location to a second location in said memories, triggered by an arbitrary time base reading.

20. The method of claim 19 for a SLIDE display further including the step of forming a time stationary display of a larger interval of ECG video signal and in which said video said larger interval is enhanced to distinguish it from adjacent intervals.

21. The method of claim 20 further including the step of moving the displayed time segment and corresponding cursor window in time to an interval of interest in said time stationary display.

22. A method for displaying ECG signals taken from a data recording thereof for detailed analysis by an electrocardiograph operator in which the operator or an arrhythmia analyzer switches the display from a time moving scan mode to a time stationary mode of display over an interval of scanned ECG signals, comprising the steps of:

converting the ECG signal to an ECG digital signal, storing at least a pre-determined interval of the ECG digital signal in an ECG memory, detecting the R-wave of said ECG signal and converting the same to an R wave digital signal, storing the R wave digital signal in an R wave memory, for a pre-determined interval of said ECG signal, displaying a plurality of said ECG digital signals seriatiam and superimposed over each other to form a visual portion of AVSEP display, displaying said ECG digital signal repetitively on a single CRT scope for operator viewing at a rate higher than the flicker frequency, continuously updating said ECG, and R wave memories and displays of said ECG digital signals and arrhythmiagraph, switching to said time stationary display upon operator or machine command and displaying an interval of the stored ECG digital signal encompassing said pre-determined interval displayed in said scan mode, so as to encompass the immediately preceding scanned ECG digital signals.

23. A display system for high speed viewing of extended ECG recordings, comprising:

means for scanning the recording at a pre-determined speed and for developing an ECG video signal therefrom, ECG memory, address means for writing said ECG video signal into said ECG memory, an R wave memory for detecting the R wave of ECG events on said ECG recording and forming an R wave pulse train therefrom, address means for writing said R wave pulse train into said R wave memory, address counter means for reading intervals of ECG memory from the addresses representing a few cycles of ECG complexes triggered by recalling the corresponding R wave pulse train at addresses offset from said ECG addresses such that each successive complete ECG complex is displayed in AVSEP mode superimposed on each other, means for continuously updating each of said memories as said recording is scanned.

24. The display system as in claim 23 further including:

means for stopping said scan at a particular point of interest, means for reading and displaying said video ECG signal over an interval encompassing the addresses from first address to a second address in each of said memories against an arbitrary time base, said means being alternately and continually repeated at a rate to give the impression of a time steady continuous display to the operator.

25. The display system as in claim 23 further including means for displaying a portion of the contents of said ECG means of about four to twelve cycles in duration as an AVSEP superimposed display of successive ECG complexes.

26. The display system as in claim 23 further including:

means for providing a SLIDE mode display of non-superimposed continuous ECG signals together with an arrhythmiagraph encompassing the interval of said ECG recording displayed and means for enhancing that portion of the arrhythmiagraph display which corresponds to said interval of said ECG recording displayed.

27. A multiple display system for the analysis of ECG signals from a recording thereof, comprising:

means for scanning said recording at high speed and for generating video signals of successive ECG events therefrom, AVSEP memory means for storing an interval of ECG signals, R wave signal detector means for generating a sequence of R waves from said ECG signals, R wave memory means for storing said sequence of R wave pulses, means for continually updating said R wave memory and said AVSEP memory as said tape is scanned, read means for periodically reading said memories, said read means generating an address offset for developing a delay between data read from each of said memories, R-R display control means for alternatively and successively displaying from said AVSEP and R-wave memory means: (i) an AVSEP trace of successive ECG complexes superimposed upon each other; or (ii) a time stationary display of an interval of ECG signals encompassing the AVSEP display over a time segment larger than said AVSEP trace.

28. An AVSEP display system for ECG signals characterized by having an R wave taken from a recording thereof over a long time period comprising:

means for playing back said recording at a fast scan speed and for developing an ECG video signals, an analog to digital converter for converting said video signal into a digital ECG signal, a digital ECG memory for storing a predetermined interval of video signals, an R wave detector for detecting R waves and for generating a sequence of trigger pulses corresponding to said detected R waves, a trigger pulse memory for storing an interval of the trigger pulses, means for repeatedly replacing an interval of ECG video signals in said ECG memory with new ECG video signals as said recording is scanned, means for repeatedly placing an interval of the trigger pulses in said trigger pulse memory with new trigger pulses as said recording is scanned, DAC means for converting the ECG digital signal into an analog ECG signal for display, first address counter means for addressing said ECG memory, second address counter means for addressing said R-wave memory, means for causing one of said first and second address counter means to be offset by a preload count, means for reading out said ECG memory as a Y signal axis and said trigger pulse memory as an X signal axis to create an AVSEP display and single gun CRT means for displaying said AVSEP above the flicker frequency to provide a continuously appearing simultaneous display thereof.

29. The display system as in claim 28 further including:

means for a time stationary mode of display including an ECG memory for each of one or more ECG channels, and a microcomputer for controlling the output from each memory, means for programming the microcomputer to compute stop and start addresses for each time stationary display corresponding to each ECG channel, slide presentation, for Z axis intensification, and for printout.

30. The display system as in claim 29 including:

means for recomputing said start and stop addresses to allow a predetermined ECG interval to slide through said ECG memory.

* * * * *